US009200330B2

(12) United States Patent
Yamasaki et al.

(10) Patent No.: US 9,200,330 B2

(45) Date of Patent: Dec. 1, 2015

(54) **DETECTION OF BACTERIA BELONGING TO THE GENUS *CAMPYLOBACTER* BY TARGETING CYTOLETHAL DISTENDING TOXIN**

(75) Inventors: Shinji Yamasaki, Sakai (JP); Masahiro Asakura, Osaka (JP)

(73) Assignees: Osaka Prefecture University, Osaka (JP); Fuso Pharmaceutical Industries, Ltd., Osaka (JP)

(*) Notice: Subject to any disclaimer, the term of this patent is extended or adjusted under 35 U.S.C. 154(b) by 839 days.

(21) Appl. No.: 12/711,129

(22) Filed: Feb. 23, 2010

(65) Prior Publication Data

US 2010/0248238 A1 Sep. 30, 2010

Related U.S. Application Data

(63) Continuation-in-part of application No. PCT/JP2008/053215, filed on Feb. 26, 2008.

(30) Foreign Application Priority Data

Aug. 24, 2007 (JP) ................................ 2007-218962
Aug. 25, 2008 (JP) ................................ 2008-215643

(51) Int. Cl.
*C12Q 1/68* (2006.01)
*C07H 21/04* (2006.01)

(52) U.S. Cl.
CPC ..................................... *C12Q 1/689* (2013.01)

(58) Field of Classification Search
None
See application file for complete search history.

(56) References Cited

U.S. PATENT DOCUMENTS

| | | | | |
|---|---|---|---|---|
| 5,447,848 | A | 9/1995 | Barns et al. | |
| 5,691,138 | A | 11/1997 | Guesdon et al. | |
| 5,998,138 | A | 12/1999 | Stonnet et al. | |
| 7,563,594 | B2 | 7/2009 | Yamasaki et al. | |
| 7,595,386 | B2 | 9/2009 | Borrelli | |
| 2008/0261220 | A1* | 10/2008 | Cracauer et al. | 435/6 |
| 2010/0047797 | A1 | 2/2010 | Yamasaki et al. | |
| 2010/0069611 | A1 | 3/2010 | Yamasaki et al. | |

FOREIGN PATENT DOCUMENTS

| | | |
|---|---|---|
| EP | 0350205 B1 | 2/1995 |
| EP | 0711841 | 5/1996 |
| EP | 1 698 698 | 9/2006 |
| EP | 1927664 | 6/2008 |
| JP | 62228096 | 10/1987 |
| JP | 284200 | 3/1990 |
| JP | 2154700 | 6/1990 |
| JP | 3112498 | 5/1991 |
| JP | 5276999 | 10/1993 |
| JP | 690795 | 4/1994 |
| JP | 690796 | 4/1994 |
| JP | 7505535 | 6/1995 |
| JP | 10-508449 | 8/1998 |
| JP | 2000316590 | 11/2000 |
| JP | 2001524825 | 12/2001 |
| JP | 2006-087406 | 4/2006 |
| JP | 2008-154581 | 7/2008 |
| WO | 96/15261 | 5/1996 |
| WO | WO9842842 | 10/1998 |
| WO | 01/77372 | 10/2001 |
| WO | WO 2005/054472 | 6/2005 |

OTHER PUBLICATIONS

Heid et al. Real time quantitative PCR. Genome Research 6:986-994 (1996).*

Asakura, "Development of a rapid method for identifying *Campylobacter jejuni, C. coli*, and *C. fetus* bacterial species using Cytolethal distending toxin (cdt) gene and application thereof" Presentation of doctoral thesis of the Osaka Prefecture University, Graduate School of Agricultural and Life Sciences, Division of Veterinary Science, Feb. 27, 2007.

Asakura, "Development of a rapid method for identifying *Campylobacter jejuni, C. coli*, and *C. fetus* bacterial species using Cytolethal distending toxin (cdt) gene and application thereof" Osaka Prefectur University Graduate School (Veterinary Science) Doctoral Thesis, Jun. 20, 2007.

Asakura et al., "Comparative analysis of cytolethal distending toxin (cdt) genes among *Campylobacter jejuni, C. coli*, and *C. fetus* strains" Microbial Pathogenesis, 42(5-6):174-183 (May-Jun. 2007).

Martinez et al., "Detection of cdtA, cdtB, and cdtC genes in *Campylobacter jejuni* by multiplex PCR" International Journal of Medical Microbiology, 296(1):45-48 (2006).

Shiramaru et al., "Shu Tokuiteki Cytolethal distending toxin Idenshi ni Motozuku nested-multiplex PCR o Mochita *Campylobacter*-zoku Saikin no Jinsoku Kenshutsu" Proceedings of the 143rd meeting of the Japanese Society of Veterinary Science, 143rd:201 (#FP2-195) (Mar. 15, 2007) (International Search Report attached for a concise explanation).

Yamasaki et al., "Cytolethal Distending Toxin (cdt); Genetic Diversity, Structure and Role in Diarrheal Disease" Toxin Reviews, 25(1):61-88 (2006).

(Continued)

*Primary Examiner* — Samuel Woolwine

(74) *Attorney, Agent, or Firm* — Karl Bozicevic; Bozicevic, Field & Francis LLP

(57) ABSTRACT

An objective of the present invention is to provide the cytolethal distending toxin (CDT) of *C. hyointestinalis* and polynucleotides encoding it, and novel methods for detection of *C. hyointestinalis* using the cdt genes. The present inventors focused on the cytolethal distending toxin (CDT) of *Campylobacter* bacteria, and detected the cdt genes of a *Campylobacter*-like bacterium isolated from an enteritis patient in Thailand. The present inventors discovered a bacterial strain whose cdtB gene was amplified by common primers in *C. jejuni, C. coli*, and *C. fetus*, but not by multiplex PCR that can specifically detect the cdtA, cdtB, and cdtC genes of the three bacterial species. The bacterial strain was identified as *C. hyointestinalis* by 16S rRNA gene analysis. Furthermore, the entire nucleotide sequence of the cdt genes was determined by genome walking upstream and downstream of the cdtB gene.

4 Claims, 19 Drawing Sheets

(56) References Cited

OTHER PUBLICATIONS

Database Uniprot [Online] "Cytolethal distending toxin C (dctC) of *Campylobacter jejuni*" XP002646136, accession No. UNIPROT: Q5F1K4 *Amino Acid Sequence* (Mar. 2005).
Stratagene Catalog (1988); cover and page 39.
Unpublished U.S. Appl. No. 13/458,532, filed Apr. 27, 2012 entitled "Cytolethal Distending Toxins and Detection of *Campylobacter* Bacteria Using the Same as a Target" and assigned to Fuso Pharmaceutical Industries, Ltd.
Asakura et al., "Development of a Multiplex PCR Assay for the Detection of the Cytolethal Ditending Toxin Genes in *Campylobacter jejuni, C. coli* and *C. fetus*" Abstracts of the General Meeting of the American Society for Microbiology. May 24, 2004; 104th:209 (#D-091).
Asakura et al., "Cloning of the CDT gene of *Campylobacter fetus* and analysis thereof" Japanese Journal of Bacteriology. 2004:59(1):283(#3093).
Asakura et al., "Molecular epidemiological investigation on CDT-producing *Campylobacter* isolated from domestic animals" Japanese Journal of Bacteriology. 2005:60(1):165(#P2-162).
Bang et al., "PCR detection of seven virulence and toxin genes of *Campylobacter jejuni* and *Campylobacter coli* isolates from Danish pigs and cattle and cytolethal distending toxin production of the isolates" Journal of Applied Microbiology, 94:1003-1014 (2003).
Bang et al., "Prevelence of cytolethal distending toxin (cdt) genes from CDT production in *Campylobacter* spp. isolated from Danish broilers" J. Med. Microbiol., 50L1087-1094 (2001).
Blaser et al., "*Campylobacter* Enteritis: Clinical and Epidemiologic Features" Ann. Intern. Med. (Aug. 1979) 91 (2):179-85.
Cortes-Bratti et al., "The *Haemophilus ducreyi* Cytolethal Distending Toxin Induces Cell Cycle Arrest and Apoptosis via the DNA Damage Checkpoint Pathways" J. Biol. Chem. (Feb. 16, 2001) 276(7):5296-302.
Dassanayake et al., "*Campylobacter hyointestinalis* strain MN-P-80-4577-4 cytolethal distending partial cds" GenBank Accession No. DQ497437: May 17, 2006.
Eyigor et al., "Cytolethal Distending Toxin Genes in *Campylobacter jejuni* and *Campylobacer coli* Isolates: Detection and Analysis by PCR" Journal of Clinical Microbiology, 37(5):1646-1650 (May 1999).
Eyigor et al., "Detection of Cytolethal Distending Toxin Activity and cdt Genes in *Campylobacter* spp. Isolated from Chicken Carcasses" Applied and Environmental Microbiology, 65(4):1501-1505 (Apr. 1999).
Gene Bank accession No. U51121.
Kopecko et al., "*Campylobacter jejuni*-microtubule-dependent invasion" Trends Microbiol. (Aug. 2001) 9(8):389-96.
Kudoh et al., Syouni naika. (1997) 29(9):1219-22.
Lara-Tejero et al., "A Bacterial Toxin That Controls Cell Cycle Progression as a Deoxyribonuclease I-Like Protein" Science (Oct. 13, 2000) 290(5490):354-7.
Lara-Tejero et al., "Cytolethal distending toxin: limited damage as a strategy to modulate cellular functions" Trends Microbiol., (Mar. 2002) 10(3):147-52.
Lastovica et al., "Clinical Significance of *Campylobacter* and Related Species Other Than *Campylobacter jejuni* and *C. coli" Campylobacter* 2000:2nd ed: 89-120.
Mizuno et al., "Characteristics of cytotoxin produced by *Campylobacter jejuni* strains" Microbios. (1994) 78 (317)215-28.
Okuda et al., "Examination of Diarrheagenicity of Cytolethal Distending Toxin: Suckling Mouse Response of the Products of the cdtABC Genes of *Shigella dysenteriae*" Infect Immun. (Feb. 1997) 65(2):428-33.
Oyofo et al., "Specific Detection of *Campylobacter jejuni* and *Campylobacter coli by* Using Polymerse Chain Reaction" J Clin Microbiol. (Oct. 1992) 30(10):2613-9.
Pickett et al., "The cytolethal distending toxin family" Trends Microbiol. (Jul. 1999) 7(7):292-7.
Pickett et al., "Prevalence of Cytolethal Distending Toxin Production in *Campylobacter jejuni* and Relatedness of *Campylobacter* sp. cdtB Genes" Infection and Immunity, 64(6):2070-2078 (Jun. 1996).
Romaniuk et al., "*Campylobacter pylori*, the Spiral Bacterium Associated with Human Gastritis, Is Not a True *Campylobacter* sp." J Bacteriol. (May 1987) 169(5):2137-41.
Samusurunsuku et al., "Molecular characterization of cytolethal distending toxin of *Campylobacter hyointestinalis*" Japanese Journal of Bacteriology. Feb. 25, 2007: 62(1):103(#P-129).
Shane et al., Diseases of Poultry, (2003) 615-30.
Suzuki et al., "Immunological properties and ganglioside recognitions by *Campylobacter jejuni*-enterotoxin and cholera toxin" FEMS Immunol Med Microbiol. (Mar. 1994) 8(3):207-11.
Takahashi et al., Infectious Diseases Weekly Report Japan (2001) 3(6):10-2.
Tauxe, Robert V., "Epidemiology of *Campylobacter jejuni* Infections in the United States and Other Industrialized Nations" *Campylobacter jejuni*: Current Status and Future Trends. 1991:9-19, American Society for Microbiology.
Totten et al., "Prevalence and Characterization of Hippurate-Negative *Campylobacter jejuni* in King County, Washington" J Clin Microbiol. (Sep. 1987) 25(9):1747-52.
Volokhov et al., "Microarray-Based Identification of Thermophilic *Campylobacter jejuni, C. coli, C. lari*, and *C. upsaliensis*" Journal of Clinical Microbiology, 41(9):4071-4080 (Sep. 2003).
U.S. Appl. No. 14/052,434, filed Oct. 11, 2013 entitled "Detection of Bacteria Belonging to the Genus *Campylobacter* by Targeting Cytolethal Distending Toxin".
Elnifro et al., "Multiplex PCR: Optimization and Application in Diagnostic Virology" Clinical Microbiology Reviews (2000) 13(4):559-569.
Integrated Research Program for Functionality and Safety of Food Toward an Establishment of Healthy Diet—Safety—Jul. 2008, No. 445, pp. 196-200.
"Muteki no Biotechnical Series" Revised Edition "Idenshi Kogaku Jikken Note (Last Volume) Idenshi no Kaiseka From Sequence to Microarray" May 15, 2006 2nd Edition, 6th Printing pp. 167-174.
Tu et al., "Campylobacter jejuni response to human mucin MUC2: modulation of colonization and pathogenicity determinants" Journal of Medical Microbiology (2008) 57(7):795-802.
Wolffs et al., "Simultaneous quantification of pathogenic Campylobacter and Salmonella in chicken rinse fluid by a flotation and real-time multiplex PCR procedure" International Journal of Food Microbiology (2007) 117(1):50-54.
Asakura et al., "III-D-6 Analysis of the Conservation of cdt Gene Cluster Retained by Campylobacter Bacteria" Journal of Bacteriology (Feb. 25, 2006) vol. 61, No. 1, p. 130, III-D-6.
"Differentiation of Campylobacter DNA molecules—Cloning and structural analysis of full-length cytolethal distending toxin (CDT) gene operon from Campylobacter lari-" Journal of Azabu University (2007) vol. 15-16, pp. 229-234.

* cited by examiner

LANE 1: MOLECULAR WEIGHT MARKER
LANE 2: C.jejuni Co1-8
LANE 3: C.jejuni Co1-119,
LANE 4: C.jejuni Co1-126
LANE 5: C.coli Co1-192
LANE 6: C.coli Co1-243

LANE 1: MOLECULAR WEIGHT MARKER
LANE 2: *C.jejuni* Co1-8
LANE 3: *C.jejuni* Co1-119
LANE 4: *C.jejuni* Co1-126
LANE 5: *C.coli* Co1-192
LANE 6: *C.coli* Co1-243

LANE 1:MOLECULAR WEIGHT MARKER
LANE 2:*C.jejuni* Co2-037
LANE 3:*C.jejuni* Co2-127
LANE 4:*C.jejuni* Co2-128
LANE 5:*C.jejuni* Co2-130
LANE 6:*C.jejuni* Co2-132
LANE 7:*C.jejuni* Co2-146
LANE 8:*C.jejuni* Co2-150
LANE 9:*C.jejuni* Co2-193
LANE 10:*C.jejuni* Co2-200
LANE 11:*C.jejuni* Co2-214
LANE 12:*C.jejuni* Co2-217
LANE 13:*C.jejuni* Co3-007
LANE 14:*C.jejuni* Co3-008
LANE 15:*C.jejuni* Co3-011
LANE 16:*C.jejuni* Co3-012
LANE 17:*C.jejuni* Co3-024

LANE 1:MOLECULAR WEIGHT MARKER
LANE 2:*C.coli* Co2–215
LANE 3:*C.coli* Co2–218
LANE 4:*C.coli* Co3–134
LANE 5:*C.jejuni* Co1–8
LANE 6:*C.coli* Co1–192
LANE 7:*C.fetus* Co1–187
LANE 8:*E.coli* JM109

LANE 1: MOLECULAR WEIGHT MARKER
LANE 2: *C.jejuni* Co1-8
LANE 3: *C.jejuni* Co1-119
LANE 4: *C.jejuni* Co1-126
LANE 5: *C.coli* Co1-192
LANE 6: *C.coli* Co1-243
LANE 7: *C.fetus* Co1-187
LANE 8: *C.fetus* Co1-99

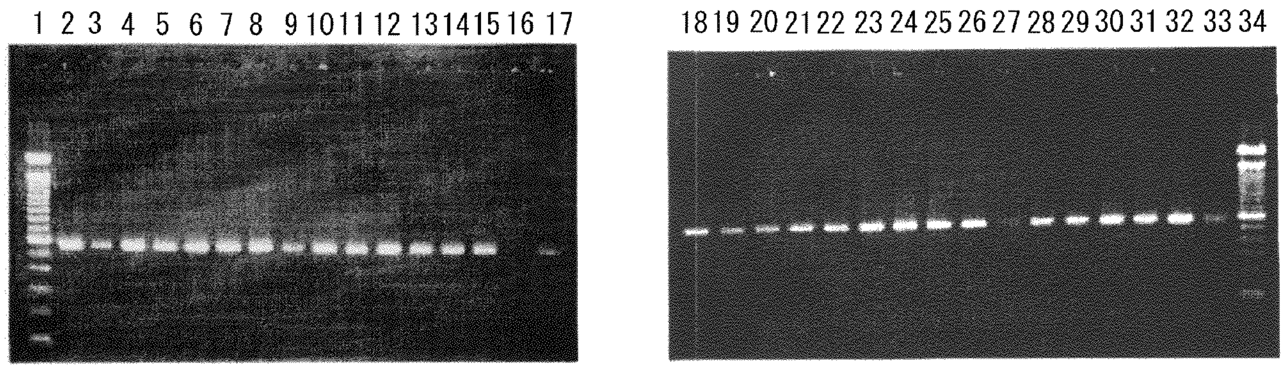

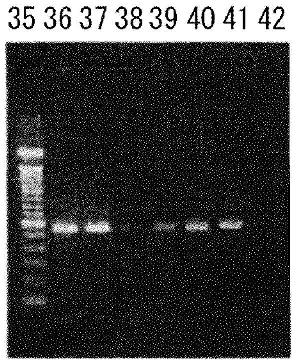

LANES 1,34,35: MOLECULAR WEIGHT MARKER
LANE 2: *C.jejuni* Co2-037
LANE 3: *C.jejuni* Co2-127
LANE 4: *C.jejuni* Co2-128
LANE 5: *C.jejuni* Co2-130
LANE 6: *C.jejuni* Co2-132
LANE 7: *C.jejuni* Co2-146
LANE 8: *C.jejuni* Co2-150
LANE 9: *C.jejuni* Co2-193
LANE 10: *C.jejuni* Co2-200
LANE 11: *C.jejuni* Co2-214
LANE 12: *C.jejuni* Co2-217
LANE 13: *C.jejuni* Co3-007
LANE 14: *C.jejuni* Co3-008
LANE 15: *C.jejuni* Co3-011
LANE 16: *C.jejuni* Co3-012
LANE 17: *C.jejuni* Co3-024
LANE 18: *C.jejuni* Co3-036
LANE 19: *C.jejuni* Co3-072
LANE 20: *C.jejuni* Co3-078
LANE 21: *C.jejuni* Co3-082
LANE 22: *C.coli* Co1-017
LANE 23: *C.coli* Co1-071
LANE 24: *C.coli* Co1-106
LANE 25: *C.coli* Co1-124
LANE 26: *C.coli* Co1-130
LANE 27: *C.coli* Co1-194
LANE 28: *C.coli* Co1-245
LANE 29: *C.coli* Co1-247
LANE 30: *C.coli* Co2-060
LANE 31: *C.coli* Co2-082
LANE 32: *C.coli* Co2-147
LANE 33: *C.coli* Co2-173
LANE 36: *C.coli* Co2-215
LANE 37: *C.coli* Co2-218
LANE 38: *C.coli* Co3-134
LANE 39: *C.jejuni* Col-8
LANE 40: *C.coli* Col-192
LANE 41: *C.fetus* Col-187
LANE 42: *E.coli* JM109

FIG. 12

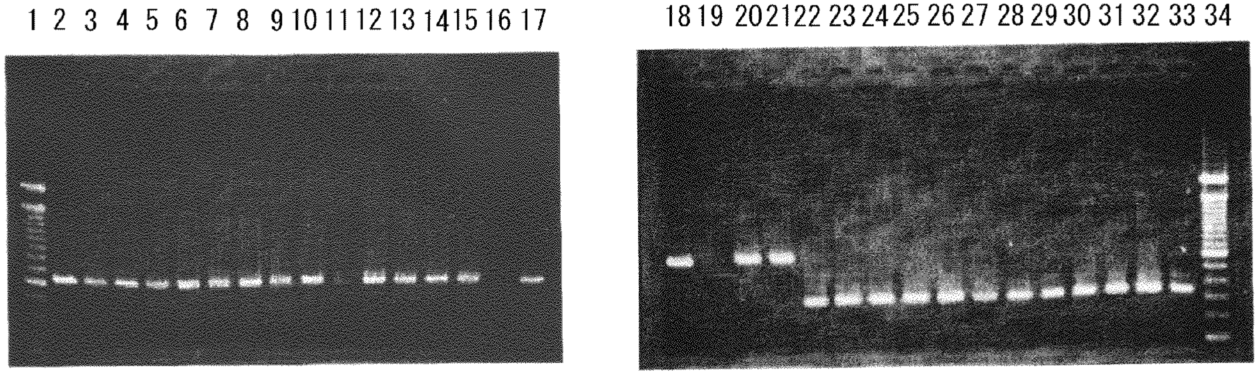

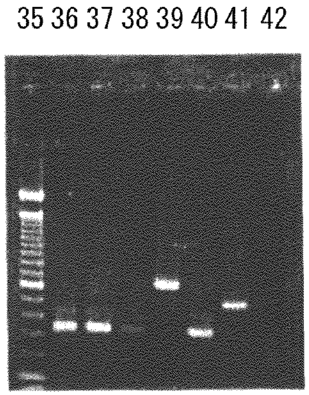

LANES 1,34,35 : MOLECULAR WEIGHT MARKER
LANE 2 : *C.jejuni* Co2-037
LANE 3 : *C.jejuni* Co2-127
LANE 4 : *C.jejuni* Co2-128
LANE 5 : *C.jejuni* Co2-130
LANE 6 : *C.jejuni* Co2-132
LANE 7 : *C.jejuni* Co2-146
LANE 8 : *C.jejuni* Co2-150
LANE 9 : *C.jejuni* Co2-193
LANE 10 : *C.jejuni* Co2-200
LANE 11 : *C.jejuni* Co2-214
LANE 12 : *C.jejuni* Co2-217
LANE 13 : *C.jejuni* Co3-007
LANE 14 : *C.jejuni* Co3-008
LANE 15 : *C.jejuni* Co3-011
LANE 16 : *C.jejuni* Co3-012
LANE 17 : *C.jejuni* Co3-024
LANE 18 : *C.jejuni* Co3-036
LANE 19 : *C.jejuni* Co3-072
LANE 20 : *C.jejuni* Co3-078
LANE 21 : *C.jejuni* Co3-082
LANE 22 : *C.coli* Co1-017
LANE 23 : *C.coli* Co1-071
LANE 24 : *C.coli* Co1-106
LANE 25 : *C.coli* Co1-124
LANE 26 : *C.coli* Co1-130
LANE 27 : *C.coli* Co1-194
LANE 28 : *C.coli* Co1-245
LANE 29 : *C.coli* Co1-247
LANE 30 : *C.coli* Co2-060
LANE 31 : *C.coli* Co2-082
LANE 32 : *C.coli* Co2-147
LANE 33 : *C.coli* Co2-173
LANE 36 : *C.coli* Co2-215
LANE 37 : *C.coli* Co2-218
LANE 38 : *C.coli* Co3-134
LANE 39 : *C.jejuni* Col-8
LANE 40 : *C.coli* Col-192
LANE 41 : *C.fetus* Col-187
LANE 42 : *E.coli* JM109

FIG. 15

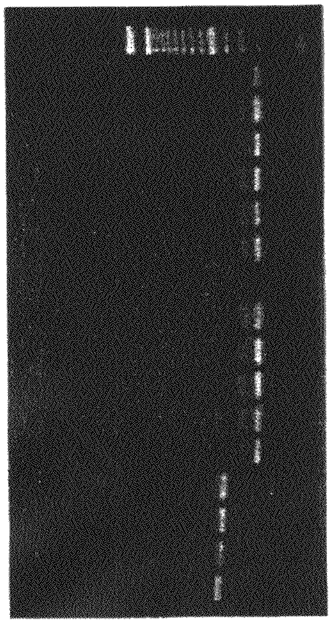

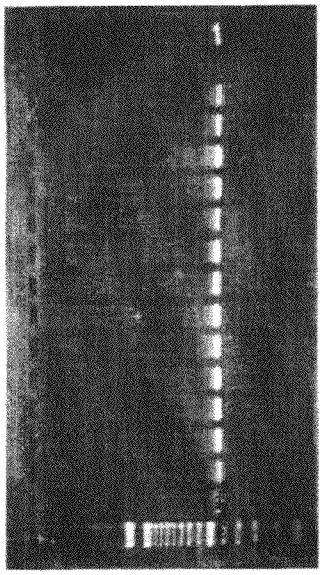

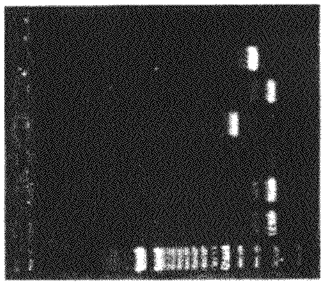

LANES 1,34,35 : MOLECULAR WEIGHT MARKER
LANE 2 : *C.jejuni* Co2-037
LANE 3 : *C.jejuni* Co2-127
LANE 4 : *C.jejuni* Co2-128
LANE 5 : *C.jejuni* Co2-130
LANE 6 : *C.jejuni* Co2-132
LANE 7 : *C.jejuni* Co2-146
LANE 8 : *C.jejuni* Co2-150
LANE 9 : *C.jejuni* Co2-193
LANE 10 : *C.jejuni* Co2-200
LANE 11 : *C.jejuni* Co2-214
LANE 12 : *C.jejuni* Co2-217
LANE 13 : *C.jejuni* Co3-007
LANE 14 : *C.jejuni* Co3-008
LANE 15 : *C.jejuni* Co3-011
LANE 16 : *C.jejuni* Co3-012
LANE 17 : *C.jejuni* Co3-024
LANE 18 : *C.jejuni* Co3-036
LANE 19 : *C.jejuni* Co3-072
LANE 20 : *C.jejuni* Co3-078

LANE 21 : *C.jejuni* Co3-082
LANE 22 : *C.coli* Co1-017
LANE 23 : *C.coli* Co1-071
LANE 24 : *C.coli* Co1-106
LANE 25 : *C.coli* Co1-124
LANE 26 : *C.coli* Co1-130
LANE 27 : *C.coli* Co1-194
LANE 28 : *C.coli* Co1-245
LANE 29 : *C.coli* Co1-247
LANE 30 : *C.coli* Co2-060
LANE 31 : *C.coli* Co2-082
LANE 32 : *C.coli* Co2-147
LANE 33 : *C.coli* Co2-173
LANE 36 : *C.coli* Co2-215
LANE 37 : *C.coli* Co2-218
LANE 38 : *C.coli* Co3-134
LANE 39 : *C.jejuni* Col-8
LANE 40 : *C.coli* Col-192
LANE 41 : *C.fetus* Col-187
LANE 42 : *E.coli* JM109

FIG. 16

C. jejuni cdt ORF

ATGCAAAAAATTATAGTTTTTATTTTATGTTGTTTTATGACTTTTTTTCTTTATGCATGTTCTTCTAAATTTGAAAATGT
AAATCCTTTGGGGCGTTCATTTGGAGAATTT$_{64}$GAAGATACTGATCCTTTAAAACT$_{7}$AGGACTTGAACCTACTTTTC$_{68}$CT
ACCAATCAAGAAATTCCAAGTTTAATTAGCGGTGCTGATTTAGTACCTATTACTCCTATTACCCCACCTTTAACTAGAAC
AAGCAATAGTGCCAACAATAATGCAGCAAATGGGATCAATCCTCGCTTTAAAGACGAAGCTTTTAATGATGTTTTAATTT
TTGAAAATCGCCCTGCGGTTTCTGATTTTTTAACCATTTTAGGCCCTAGCGGAGCAGCTTTAACGGTTTGGGCTTTAGCA
CAAGGAAATTGGATTTGGGGCTATACTTTAATCGATAGCAAAGGATTTGGCGATGCTAGAGTTTGGCAACTTTTGCTTTA
TCCTAATGATTTTGCAATGATTAAAAATGCCAAAACCAATACTTGTCTTAATGCTTATGGTAATGGAATTGTCCATTATC
CTTGTGATGCAAGCAATCACGCACAAATGTGGAAACTTATCCCTATGAGCAATACAGCGGTTCAAATTAAAAATTTAGGA
AATGGAAAA$_{65}$TGCATACAAGCACCTATTACAAATCTTTATGGTGATTTTCACAAGGTTTTTAAAATTTTTACCGTAGAG
TGTGCAAAAAAAGATAATTTTGATCAACAAT$_{69}$GGTTTTTAACTACTCCGCCTTTTACCGCA$_{11}$AAACCTTTATATCGCCA
AGGAGAGGTACGATGAAAAAAATTATATGTTTATTTTTATC$_{17}$TTTTAACCTTGCTTTTGCAAATTTAGAAAATTTTAAT
GTTGGCACTTGGAATTTGCAAGGC$_{9}$TCATCCGCAGCCACAGAAAGCAAATGGA$_{18}$GTGTTAGTGTAAGACAACTTGTAAGT
GGAGCAAACCCCTTAGATATCTTAATGATAC$_{26}$AAGAAGCAGGAACTTTACCAAGAAC$_{29}$AGCCACTCCAACAGGACGCC$_{19}$
ATGTGCAACAAGGTGGAACACC$_{27}$TATTGATGAATATGAGTGGAATTTAGG$_{20}$AACTCTTTCAAGGCCTGATAGGGTTTTT
ATTTATTATTCTCGCGTTGATGTAGGAG$_{48}$CTAATCGTGTAAATTTAGCTATAGTTTCAAGAATGCAAGCTGAA$_{21}$GAAGT
GATTGTTTTACCTCCACCTACTACAGTTTCAAGACCCATTATAGGAATTCGCAATGGAAATGATGCTTTTTTCAATATCC
ATGCTTTAGC$_{49}$TAATGGAGGAACAGATGTAGGAGCAATTATCACAGCTGTAGATGCACA$_{22}$TTTTGCAAATATGCCTCAA
GTTAACTGGATGATAGCAGGGGATTTTAA$_{50}$CCGTGATCCTTCTACTATAACAAGT$_{23}$ACAGTGGATAGAGAATTAGCAAA
TAGAATTAGAGTGGTTTTTCCAACTAGCGCAACTCAAGCAAGCGGAGGGACTCTTGATTATGCAATTACAGGAAATTCAA
ATA$_{24}$GACAACAAACCTATACTC$_{12}$CACCGCTTTTAGCTGCGATTTTAATGCTTGCAAGTTTAAGATCTCATAT$_{25}$AGTTTC
AGATCATTTTCCAGTAAATTTTAGA$_{10}$AAATTTTAGGACATTTAATATGAAAAAAATTATTACTTTGTTTTTTATGTTTA
TAACTTTAGCCTTTGCAACTCCTA$_{74}$CTGGAGATTTGAAAGATTTTACCGAAATGGTTTCTATAAGAAGCTTAGAAACGG
GAATTTTTTTAAGCGCCTTTAGGGATACCTCAAAA$_{66}$GATCCTATTGATCAAAATTGGAATATTAAAGAAATTGTTTTAA
GCGATGAGTTAAAACAAAAAGATAAATTAGCTGATGAACTTCCTTTTGGTTATGTGCAATTTACAAATCCAAAAGAAAGC
GATCTTTGTTTAGCCATCTTAGAAGATGGAACCTTTGGAGCAAAATCTTGTCAAGATGATCTAAAAGATGGTAAATTAGA
AACTGTATTTTCTATAATGCCAACAACAACTTCAGCTGTGCAAATTCGTTCTTTAGTTTTGGAATCTGATGAATGTATAG
TAACTTTTTTTAATCCAAATATTCCTATACAAAAACGCTTTGGAA$_{8}$TAGC$_{67}$CCCTTGCACCCTAGATCCTATTTTTTTT
GCTGAAGTAAATGAACTAATGATTATAACCCCACCTTTAACAGCTGCTACCCCTT$_{75}$TAGAATAA

FIG. 17

C. coli cdt ORF

ATGCAAAAAATAAAATTAAGCCTAATGTTTTTGATTGTAACAATCATTTTTTTAGCTTGTTCTTCAAAAGAACAACAAAT
CAATCCTTTAGGAAGATCTTACGGTAAATTT$_{64}$AACGATAACGATCCTTTAAAACT$_{7}$TGGTTCAAAACCTACACCCCCTG
TCAAACAAAAAACACCAAGCTTGGTAGAAGGTAAAAAATTTCCCGCCATACCACTTGTCCCACCTGTAATCACTCCTAAT
ACCTTTAAAGGAGATAATGCCGTCAAAGGCCCATTGCCAAGGCTAAAATCTC$_{70}$CAAACGAATTTGCTTCAAATGCTTTA
TACGAAAACACAGGTATGGTAAGTGATTTTGTCACTATTATGAATCCTAATGGAGCATCTTTAACAATCTGGGCTTTAAA
TCCTGGCAATTGGATATGGGGATATAGTTTATTTGCTAGTAGACCTTTTGGAGATGCAAGAGCTTGGCAGCTTATTGAAT
TTCCAAACAATACAGTAATGATTAAAAATGCAAAAACATTTACTTGCTTAAACGCCTATAGAAATGGCATCGTTCATTAT
CCTTGTGATCAAACAAATTTTGCGCAGTTTTGGAGACTTTATC$_{71}$CGATGACTAATGGAGCTTATCAAATTCAAAATTTT
GCCACCCAACA$_{65}$ATGTATACAAACACCTGTTTCAAATGTAATGGAAGAATTTAATTTGAGCTTTTATAATATTTATTTA
ACCGATTGTTTGAAAGAAAAAGAAAAGAATTTGGATAGACAGTGGTATATAGGCGCTCCTATTTAATTTTTTCGCTATGA
AAGGAAGATAATGAAAAAAATAGTATTTTTGATTTTAAGTTTTAATGTATTATTTGCCGC$_{13}$TTTAGAAAATTACAACAC
CGGAACTTGGAATTTGCAAGGC$_{9}$TCATCAGCTGCAACTGAAAGCAAATGGAATGTTAGTATAAGACAACTCATAACCGGT
GCAAATCCTATGGATGTTTTAGCTGTTCAAGAAGCGGGGGTTTTACCTAGTACAGCTATGATGACTCCTAGACAGGTACA
ACCCGTGGGCGTGGGTATTCCTATACATGAATACATATGGAATTTAGGCTCTGTATCAAGACCTAGCTCTG$_{30}$TTTATAT
ATATTATTCTAGAGTGGATGTAGGAGCAAATCGTGTGAATTTAGCTATCGTTAGCAGAGTGCAAGCGGATGAAGTTTTTG
TTTTACCCCCTCCAACAGTTGCTTCAAGACCTATTATAGG$_{31}$CATACGCATAGGCAATGA$_{14}$TGCTTTTTTCAATATACAC
GCTCTAGCAAGTGGGGGAAATGACGCAGGAGCCATTGTCGCTGCT$_{32}$GTGGATATGTTTTTTAGAAATAGACCTGATATT
AATTGGATGATTTTAGGCGATTTTAATAGAGAATCAGGCGCCTTAGTAACCTTGCTAGATCCTGACTTAAGAGCACGCAC
TCG$_{33}$CGTAGTTGTTCCGCCTTCTT$_{36}$CTACGCAAACAAGTGGAAGAACGATTGATTATGCTATCACTGGAAATTCCAACA
CTGCAGCTTTATACAACCCACCACCGATAGTT$_{28}$GCGATTTTAGCTTTAGAAGGATTAAGAACCTTTTTGG$_{34}$CTTCAGAT
CATTTTCCTGTAAATTTTAGA$_{10}$AGACCTTAGGAGCTTAATATG$_{35}$AAAAAATTTTTTATTTTATTTTTTGCCCTTTTGAG
CTTTTTGAAAGCAGAGCCTAGCTTGGATGAATTAGCAGACTTTACTCCTATGTTTGCTATAAGATCTTTAGAAACAGGAA
TTTCTTTAAGTCCTTTTAGAAAAACTTCAAAA$_{66}$AGGTTAGAAGATCAAAATTGGTTTTTAAAAGAGATTGTAGCAAATG
ATGAGCTAAAAGCTAGGGATATGCACGCAAAAGA$_{76}$TTTGCCTTTTGGCTATGTTCAGTTTATAAGCCCTAGGGGCGATG
ATATATGCCTAGCTGTTTTAAGTGAAAAAAGTTTTGGCACCAAATCTTGCAAACAAGATTTGCAAGATGGAACAATGCAG
ACTATTTTTTCTATCATACCAATGACAAATGGTTCTATACAAATTAGATCTTTAACCAATGGTGGCAATCAATGCATGAG
CACTTTTCCTGACTCTAGTATCGCCATAGAAAATCGCTT$_{8}$TGGTTTAGG$_{67}$AGAATGCCTTTTGGATCGTTCTATCGTAA
CTGTATTAAGC$_{77}$AAACTTTTCTTTTTCTCCCCTGCTATAATCGAAGCAAGCGCAATTTACTAA

FIG. 18

C. fetus cdt ORF

ATGACTAAAATTATTTTCAAGCATATTAAAAATAGTCTTATTTTACTATTTTGTATCGCTCTTTTTAGTGCTTGCTCATC
AAAAACGACAAATGTAAGCACTC$_{72}$AAAAAATAAATCCATTAGGAAGCATTTTTGGCAAAACG$_{64}$GATGATCCAGATCCAC
TAAATTTAGGCGATTTTCCAACTCTTCTAACATCAAATTTTACAAATCCTATGCCGACTAGAACGCCATCGCCACTTAA
AAAAGTGGATTTGCCTGTAATGAACTCATTAACACATGGTCCGATGTTTTCAAGTGCTTTTAGTAAACCGGACTTGAATT
TCAAACAACCTACTATCAGTCTACAAGGTATCCCGCCTGATCTATTTGATAGAACAAGCGATTTTATGGTGATAATGGGT
GCAAACGGCGTTGTGATCACTATTTGGTACACATCTCCTGGAAACTGGTTATGGGGCTACTCGCTCTATGAAAGCGGCAA
TTTAGGAGGATATCGTGTTTGGCGTCTAATTTTACTACCAAATAATGAAGTCATGATAGTAAATTTCAACACTCGCACGA
CTTGCATAAATA$_{73}$CTTATAAAAACGGAGTAATTCACTCACCTTGCAATAAAGATAATCCTTTTCAGAAATTTACGTTTC
GTCCAATGACAAACGGAGCCGTACAAATTTATAACAAAGCTACTAATTGCG$_{65}$TGCTTGCAAACGCCTGTTAATAATCTA
TTCGGTTTTGACGTTTTTGGGGCGATAAATCTTACGACAAAATGCACTGATACTATCGATCAACAATGGTATTTGCTCCC
GCCGCCGCAAGTTGGAAGACTAT$_{15}$TTTATTAGGAGTAAAAATGCGAAATGTTATTATGATTATATTTATAGCAACTTTA
GGC$_{38}$TTTGCAAAACCAGAAGATTATAAAATTGCTACTTGGAATTTGCAAGGC$_{9}$AGTTCGGCTATAACCGAAAGCAAATGG
A$_{47}$ATATAAGCGTACGTCAAATAATTAGCGGTGAAAATCCAGCAGATATATTAGCCGTTCAAGAAGCAGGAAATTTACCT
CAAACCGCTCTTC$_{39}$CTACAGGTAGAAGCATAAATCAAGGCGGCACGATC$_{40}$GTAACTGAGCATTTATGGCAGCTAGGCAG
TATATCTAGACCGTTCCAA$_{41}$GTCTATATATATTATGCTCAAATCGACACAGGGGCAAATAGAGTAAATTTAGCAATCGT
TTCACGCATAAAAGCTGATGAAATCATCATCTTGCCGCCTCCT$_{42}$ACGGTAGCTTCTCGTCCGCTCATAGGTATAAGAAT
AGGAAACGACGTATTTTTCAACATACACGCTCTAGCAAATGGCGGAGTCGATGCTCCGGCGATAATAAA$_{16}$TTCAATATT
TGACAGATTTAGAAATATGCCAAATATCACTTGGATGATTTTAGGCGATTTTAACCGCTCACCTGAGAGTTTAAGA$_{43}$GG
AACTCTTGGATTAGAAACTC$_{44}$GCGTCAGAGTAACGTTTTTAACA$_{37}$CCTCCGGCGCCTACTCAAAGAAGCGGCGGAACGC
TTGACTGGGCTATAGTTGGAAACTCAGCCGGCGATCTTGTCCGAAC$_{45}$TACGCTTGTAGCAGTATTGATGCTAGCAAACC
TGCGGACTCACCTA$_{46}$GTTTCGGACCATTTTCCGGTAAATTTTAGA$_{10}$AAATTTGGAGATAACTAATGAAAGCTTTAGCAA
TAATATTTTTATTTGTAAGCATAAGTTTTGCAAACG$_{78}$AAAACATAACCGACGCTTTTCAAATACGCAATGCAAACACCG
GAATTCCTATAAATATAAAGCGATTTTCAGGG$_{66}$CAGTTTAATTACCAAAACTGGTTTTTAAATGATTTAGGAGTAGATC
CTAAGATAAAAAAAGTAGATAAATTTTCAAATTCTTTTCCTTTTGGATACGTGCAATTTCAAGTAGCAGCCGACGTAAAA
ATGTGCCTTCAGATCGCTCCTAGCGGATTTTTAGCACTAAAAAACTGCAAGCAAGACTACGATAGCGGAGAGTTTGAGAC
TATTTTTCAGATCATCCCTACAAGTAGTGGAGCTATGCAGCTACGATCACTAGTTCTAAAAACAAACGAGTGCTTAGGAA
CATTTGAAAATCCAAAC$_{79}$GTGCCGATCGAAGATAGAGTAGGACTAGT$_{67}$ACGCTGCGTTTTAGAATTTTTTGTCGACATA
GAGCCTAAACAACTTTTTGTATTTTCACCGCCGCTTAGTGAAGCTAAGGTAATTAGATAA

FIG. 19

DETECTION OF BACTERIA BELONGING TO THE GENUS *CAMPYLOBACTER* BY TARGETING CYTOLETHAL DISTENDING TOXIN

TECHNICAL FIELD

The present invention relates to methods for detecting the presence or absence of *Campylobacter* bacteria in test samples by targeting the cytolethal distending toxin of *Campylobacter* bacteria.

The present invention also relates to the cytolethal distending toxin of *Campylobacter hyointestinalis* and polynucleotides encoding it, as well as methods for detecting the presence or absence of *Campylobacter hyointestinalis* in test samples by targeting the cytolethal distending toxin of *Campylobacter hyointestinalis.*

BACKGROUND ART

Seventeen bacterial species of *Campylobacter* have been identified to date. Cultivation test is commonly used to identify *Campylobacter* bacterial species. However, the test requires complex and substantial effort because some bacterial species are difficult to identify based on their biochemical properties alone. Also, the bacteria are microaerophilic and depending on the bacterial species, some need to be cultured at different temperatures. Furthermore, the cultivation test for *Campylobacter* bacteria including isolation and identification usually takes a long time (seven to ten days).

More simple and rapid methods for identifying various species of *Campylobacter* bacteria are expected to be developed, because there is an increasing trend in both the *Campylobacter* infection rate and number of patients ("Food poisoning outbreak for each causative agent", the Ministry of Health, Labor and Welfare of the Japan).

It is difficult to rapidly identify *Campylobacter* bacterial species based on their biochemical properties, and some of *Campylobacter* species often cannot be distinguished based on their biochemical properties because of their close resemblance. For example, *Campylobacter jejuni* (hereinafter referred to as "*C. jejuni*") and *Campylobacter coli* (hereinafter referred to as "*C. coli*") are problematic because they are distinguished based on the presence of hippuricase activity, and when the enzyme activity is low, *C. jejuni* is falsely identified as *C. coli*. For this reason, PCR methods for detecting the presence of the hippuricase gene have been used in actual tests. In recent years, 16S rRNA gene analysis is frequently used as a method for identifying bacterial species at the gene level. However, *C. jejuni* and *C. coli* are highly homologous to each other, and thus often cannot be distinguished from each other by the 16S rRNA gene analysis.

To date, *C. jejuni* and *C. coli* account for about 94% and 4% of *Campylobacter* bacteria isolated from diarrhea patients, respectively. That is, the two bacterial species comprise the majority of *Campylobacter* bacteria. Thus, in most cases, test for *Campylobacter* bacteria in clinical practice only covers *C. jejuni* and *C. coli* which are specified as food poisoning bacteria. Furthermore, selection media commonly used in the test have been developed for mainly *C. jejuni* and *C. coli*, and the culture is generally carried out at 42° C. On the other hand, this bacterial isolation method is not suitable for bacterial species other than *C. jejuni* and *C. coli* because isolation of other bacterial species is less frequent. Specifically, depending on the selection medium or culture conditions used, sometimes bacterial species other than *C. jejuni* and *C. coli* cannot be isolated due to differences in the antibiotic sensitivity or optimal culture temperature among bacterial species belonging to the genus *Campylobacter*. That is, it is hard to say that the test covers *Campylobacter fetus* (hereinafter abbreviated as "*C. fetus*") which has different temperature-sensitive property, or other *Campylobacter* bacteria.

Meanwhile, bacterial species other than *C. jejuni* and *C. coli* are also distributed in the gastrointestinal tract of pets, domestic and wild animals or such, and thus the chance of human infection is thought to be high as with *C. jejuni* and *C. coli*. A mass outbreak of food poisoning caused by *C. fetus* occurred in Osaka in 2005. Infection with *C. fetus* causes not only gastroenteritis such as diarrhea but also other severe symptoms such as sepsis and meningitis in human. Furthermore, infection with *C. fetus* can result in infertility, miscarriage, or the like in animals such as cattle. In addition to *C. jejuni, C. coli*, and *C. fetus*, the three bacterial species, *Campylobacter lari* (hereinafter abbreviated as "*C. lari*"), *Campylobacter upsaliensis* (hereinafter abbreviated as "*C. upsaliensis*"), and *Campylobacter hyointestinalis* (hereinafter abbreviated as *C. hyointestinalis*"), are zoonotic bacteria that cause enteritis, sepsis, or such in human. Thus, it is important to improve the system for testing *Campylobacter* bacteria other than *C. jejuni, C. coli*, and *C. fetus.*

The present inventors cultured, isolated, and identified *Campylobacter* bacteria according to the Cape Town protocol without using antibiotics. The result showed that about 1.3% of patients with diarrhea caused by *Campylobacter* bacteria were infected with *C. hyointestinalis* (Non-patent Document 1).

*C. hyointestinalis* was isolated as a causative bacterium of porcine proliferative enteritis. Furthermore, *C. hyointestinalis* has been occasionally isolated from human enteritis patients, suggesting its involvement in human pathology. Nevertheless, there is no established rapid diagnosis method for *C. hyointestinalis.*

Thus, although the chance of potentially infecting human is highly suspected, there is no appropriate isolation/culture test method for *Campylobacter* bacteria other than *C. jejuni* and *C. coli.*

To solve the above-described problems, the present inventors focused and conducted their academic research on the cytolethal distending toxin (CDT) of *Campylobacter* bacteria (Non-patent Documents 2 and 3), and developed a method for detecting *Campylobacter* bacteria using the cytolethal distending toxin genes (cdtA, cdtB, and cdtC) (Patent Document 1). However, this detection method only targets *C. jejuni, C. coli*, and/or *C. fetus*, and no appropriate method has been developed for detecting other *Campylobacter* bacteria including *C. hyointestinalis.*

Prior art documents related to the present invention described herein are shown below.

[Patent Document 1] WO 2005/054472

Non-patent Document 1] Lastovica A J. et al., *Campylobacter*, 2nd ed, 89-120 (2000)

[Non-patent Document 2] Asakura M. et al., Microbial Pathogenesis 42 (2007) 174-183

[Non-patent Document 3] Yamasaki S. et al., Toxin Reviews, 25: 61-88, 2006

DISCLOSURE OF THE INVENTION

Problems to be Solved by the Invention

The present invention was achieved in view of the circumstances described above. An objective of the present invention is to provide the cytolethal distending toxin (CDT) of *Campylobacter hyointestinalis* and polynucleotides encoding it.

Another objective of the present invention is to provide novel methods for detecting *Campylobacter hyointestinalis* using the cdt genes.

As described above, there is a need for rapid diagnosis of infection by *Campylobacter* bacteria species other than *C. jejuni* and *C. coli*, despite the fact that the pathogenic factors of *Campylobacter* bacteria have not been fully elucidated. Conventionally, PCR primers for identifying bacterial species based on the serotype thereof, common primers for testing CDT production, and such have been used (J. Applied Microbiol., 94: 1003-1014 (2003)). However, such methods require the step of an enrichment culture, making the rapid detection of *Campylobacter* bacteria impossible.

*C. hyointestinalis* was isolated as a causative bacterium of porcine proliferative enteritis. Furthermore, *C. hyointestinalis* has been occasionally isolated from human enteritis patients, suggesting its involvement in human pathology. Although the cytotoxin-like activity of a possible *C. hyointestinalis* pathogenic factor has been reported, the details remain to be clarified. Meanwhile, Johnson and Lior discovered a novel toxin called CDT in *E. coli* (Johnson W M, Lior H. 1988. Microbial Pathogen 4, 115-126.), and reported that *C. jejuni* also produces CDT. Subsequently, Pickett et al. determined the entire nucleotide sequence of the *C. jejuni* cdt genes (Pickett C L, et al., 1996. Infect Immun, 64, 2070-2078.), thereby revealing the exact identity of CDT. Furthermore, Pickett et al. reported that *C. hyointestinalis* also produces a toxin with CDT activity, and a PCR product corresponding to the cdtB gene can be amplified from *C. hyointestinalis* using degenerative primers. However, the bacterial DNA from *C. hyointestinalis* did not react with probes for the *C. jejuni* cdtB gene, and thus the exact identity of CDT produced by *C. hyointestinalis* remains unrevealed.

Therefore, an objective of the present invention is to provide the CDT (whose nucleotide sequence has not been elucidated) of *Campylobacter hyointestinalis* belonging to the genus *Campylobacter* and polynucleotides encoding the CDT, in order to enable rapid detection of *Campylobacter* bacteria by gene amplification. Another objective of the present invention is to provide novel methods for detecting *Campylobacter hyointestinalis* using the cdt genes.

Furthermore, the present invention provides primers for simultaneous detection of *Campylobacter* bacteria including *C. hyointestinalis.*

Means for Solving the Problems

The present inventors focused on the cytolethal distending toxin (CDT), which is recently thought to be a pathogenic factor produced by *Campylobacter* bacteria, and developed simple and rapid methods for detecting *Campylobacter hyointestinalis* in a species specific manner by targeting the cdt genes. CDT is a holotoxin consisting of the three subunits, CdtA, CdtB, and CdtC. The CdtA and CdtC subunits are involved in cell binding, while the CdtB subunit has DNase activity and is the main unit of toxin that exerts toxicity. The present inventors aimed to identify the species of *Campylobacter*-like bacteria isolated from an enteritis patient in Thailand by detection of the cdt genes, and developed and utilized a multiplex PCR method that can specifically detect *C. jejuni, C. coli*, and *C. fetus* by targeting the cdtA, cdtB, and cdtC genes, and a PCR method that uses common primers to simultaneously detect the cdtB gene of the three bacterial species. As a result, the present inventors found a bacterial strain whose cdt genes were not amplified by the multiplex PCR method specific to the three bacterial species, but whose cdtB gene was amplified by the common primers. This bacterial strain was identified as *C. hyointestinalis* by 16S rRNA gene analysis.

Then, the entire nucleotide sequence of the *C. hyointestinalis* cdt genes was determined by genome walking upstream and downstream of the cdtB gene. The sequence of an unidentified gene adjacent to a known gene is generally determined by inverse PCR. However, in the present invention, the entire nucleotide sequence of the cdt genes was determined for the first time by a method in which random primer extension and genome amplification are carried out and the amplified templates are sequenced.

Furthermore, the determined nucleotide sequence and deduced amino acid sequence were compared to the sequences previously reported for CdtA, CdtB, and CdtC of *C. jejuni, C. coli*, and *C. fetus*. The result showed that the cdtA and cdtC genes of *C. hyointestinalis* are most homologous to those of *C. jejuni* and the homologies are 51.7% and 52.5%, respectively. The cdtB gene of *C. hyointestinalis* is most homologous to that of *C. coli* and the homology is 64.1%. Thus, the homology is not very high.

Meanwhile, the homology of the deduced amino acid sequences of CdtA, CdtB, and CdtC was determined. The result showed that the three Cdt subunits of *C. hyointestinalis* exhibited the highest homology to those of *C. coli*. However, high homology was not obtained, and the respective amino acid sequence homologies were 35.7%, 60.5%, and 28.9%.

The present invention relates to methods for detecting *Campylobacter* bacteria by amplifying the *Campylobacter hyointestinalis* cdt genes. Specifically, the present invention provides the following:

[1] a polynucleotide encoding a cytolethal distending toxin, which is any one of (a) to (h) below:

(a) a polynucleotide encoding a polypeptide comprising the amino acid sequence of any one of SEQ ID NOs: 2 to 4;

(b) a polynucleotide comprising any one of the nucleotide sequences of positions 962 to 1600, 1601 to 2425, and 2425 to 3177 in the nucleotide sequence of SEQ ID NO: 1;

(c) a polynucleotide encoding a polypeptide comprising an amino acid sequence with one or more amino acid substitutions, deletions, additions, and/or insertions in any one of the amino acid sequences of SEQ ID NOs: 2 to 4;

(d) a polynucleotide that hybridizes under stringent conditions to a DNA comprising any one of the nucleotide sequences of positions 962 to 1600, 1601 to 2425, and 2425 to 3177 in the nucleotide sequence of SEQ ID NO: 1;

(e) a polynucleotide encoding a polypeptide comprising the amino acid sequence of any one of SEQ ID NOs: 6 to 8;

(f) a polynucleotide comprising any one of the nucleotide sequences of positions 1059 to 1835, 1853 to 2656, and 2666 to 3202 in the nucleotide sequence of SEQ ID NO: 5;

(g) a polynucleotide encoding a polypeptide comprising an amino acid sequence with one or more amino acid substitutions, deletions, additions, and/or insertions in the amino acid sequence of any one of SEQ ID NOs: 6 to 8; and (h) a polynucleotide that hybridizes under stringent conditions to a DNA comprising any one of the nucleotide sequences of positions 1059 to 1835, 1853 to 2656, and 2666 to 3202 in the nucleotide sequence of SEQ ID NO: 5;

[2] a vector comprising the polynucleotide of [1];

[3] a host cell comprising the polynucleotide of [1] or the vector of [2];

[4] a polypeptide encoded by the polynucleotide of [1];

[5] a method for producing the polypeptide of [4], which comprises the step of culturing the host cell of [3], and collecting the produced polypeptide from the host cell or the culture supernatant;

[6] an antibody that binds to the polypeptide of [4];

[7] the antibody of [6], wherein the antibody has an activity of neutralizing a cytolethal distending toxin;

[8] a method for simultaneously detecting the presence of one or more *Campylobacter* bacteria in a test sample, which comprises the steps of:

(a) conducting a nucleic acid amplification reaction on the test sample using a mixture of primer pair(s) specific to a genomic DNA encoding a cytolethal distending toxin of a *Campylobacter* bacterium; and (b) determining the presence of *Campylobacter* bacteria based on the presence or molecular weight of an fragment amplified from the genomic DNA encoding the cytolethal distending toxin of the *Campylobacter* bacterium;

[9] the method of [8], in which any one or more of the primer pairs of (i) to (iv) below are used as primer pair(s):

(i) the primer pair of SEQ ID NOs: 24 and 25 for amplifying the genomic DNA encoding a cytolethal distending toxin of *Campylobacter hyointestinalis*, or a primer pair capable of amplifying the same genomic DNA region amplified by the primer pair of SEQ ID NOs: 24 and 25;

(ii) the primer pair of SEQ ID NOs: 18 and 19 for amplifying the genomic DNA encoding a cytolethal distending toxin of *Campylobacter hyointestinalis*, or a primer pair capable of amplifying the same genomic DNA region amplified by the primer pair of SEQ ID NOs: 18 and 19;

(iii) the primer pair of SEQ ID NOs: 32 and 33 for amplifying the genomic DNA encoding a cytolethal distending toxin of *Campylobacter* upsaliensis, or a primer pair capable of amplifying the same genomic DNA region amplified by the primer pair of SEQ ID NOs: 32 and 33; and (iv) the primer pair of SEQ ID NOs: 34 and 35 for amplifying the genomic DNA encoding a cytolethal distending toxin of *Campylobacter lari*, or a primer pair capable of amplifying the same genomic DNA region amplified by the primer pair of SEQ ID NOs: 34 and 35.

[10] the method of [9], in which the primer pairs of (v) to (vii) below are additionally used as primer pair(s):

(v) the primer pair of SEQ ID NOs: 26 and 27 for amplifying the genomic DNA encoding a cytolethal distending toxin of *Campylobacter jejuni*, or a primer pair capable of amplifying the same genomic DNA region amplified by the primer pair of SEQ ID NOs: 26 and 27;

(vi) the primer pair of SEQ ID NOs: 28 and 29 for amplifying the genomic DNA encoding a cytolethal distending toxin of *Campylobacter coli*, or a primer pair capable of amplifying the same genomic DNA region amplified by the primer pair of SEQ ID NOs: 28 and 29;

(vii) the primer pair of SEQ ID NOs: 30 and 31 for amplifying the genomic DNA encoding a cytolethal distending toxin of *Campylobacter fetus*, or a primer pair capable of amplifying the same genomic DNA region amplified by the primer pair of SEQ ID NOs: 30 and 31;

[11] a kit for use in the method of [8], which comprises a manual and a mixture of one or more primer pairs specific to the genomic DNA encoding a cytolethal distending toxin of a *Campylobacter* bacterium;

[12] the kit of [11], which comprises any one or more of the primer pairs of (i) to (iv) below as primer pairs:

(i) the primer pair of SEQ ID NOs: 24 and 25 for amplifying the genomic DNA encoding a cytolethal distending toxin of *Campylobacter hyointestinalis*, or a primer pair capable of amplifying the same genomic DNA region amplified by the primer pair of SEQ ID NOs: 24 and 25;

(ii) the primer pair of SEQ ID NOs: 18 and 19 for amplifying the genomic DNA encoding a cytolethal distending toxin of *Campylobacter hyointestinalis*, or a primer pair capable of amplifying the same genomic DNA region amplified by the primer pair of SEQ ID NOs: 18 and 19;

(iii) the primer pair of SEQ ID NOs: 32 and 33 for amplifying the genomic DNA encoding a cytolethal distending toxin of *Campylobacter* upsaliensis, or a primer pair capable of amplifying the same genomic DNA region amplified by the primer pair of SEQ ID NOs: 32 and 33; and (iv) the primer pair of SEQ ID NOs: 34 and 35 for amplifying the genomic DNA encoding a cytolethal distending toxin of *Campylobacter lari*, or a primer pair capable of amplifying the same genomic DNA region amplified by the primer pair of SEQ ID NOs: 34 and 35;

[13] the kit of [12], which further comprises the primer pairs of (v) to (vii) below as primer pairs:

(v) the primer pair of SEQ ID NOs: 26 and 27 for amplifying the genomic DNA encoding a cytolethal distending toxin of *Campylobacter jejuni*, or a primer pair capable of amplifying the same genomic DNA region amplified by the primer pair of SEQ ID NOs: 26 and 27;

(vi) the primer pair of SEQ ID NOs: 28 and 29 for amplifying the genomic DNA encoding a cytolethal distending toxin of *Campylobacter coli*, or a primer pair capable of amplifying the same genomic DNA region amplified by the primer pair of SEQ ID NOs: 28 and 29;

(vii) the primer pair of SEQ ID NOs: 30 and 31 for amplifying the genomic DNA encoding a cytolethal distending toxin of *Campylobacter fetus*, or a primer pair capable of amplifying the same genomic DNA region amplified by the primer pair of SEQ ID NOs: 30 and 31;

[14] a method for detecting the presence of *Campylobacter hyointestinalis* in a test sample, which comprises the steps of:

(a) contacting a test sample with the antibody of [6];

(b) measuring the binding between the test sample and the antibody of [6]; and (c) determining that *Campylobacter hyointestinalis* is present if the binding is detected in (b);

[15] a kit for use in the method of [14], which comprises a manual and the antibody of [6].

BRIEF DESCRIPTION OF THE DRAWINGS

FIG. 4A presents a photograph showing detection of Ch-CdtB by SDS-PAGE. FIG. 4B presents a photograph showing detection of Ch-CdtB by Western blotting. Lane 1, molecular weight marker; lane 2, 25 ng of Ch-rCdtB; lane 3, 10 μl of a crude toxin solution from *C. hyointestinalis* (Ch022). FIG. 4C presents a photograph showing the specificity of the Ch-rCdtB antiserum in gel double diffusion. rCjB, 1 μg of *C. jejuni* rCdtB; α-Cj, 10 μl of rCjB antiserum; rChB, 1 μg of *C. hyointestinalis* rCdtB; α-Ch, 10 μl of rChB antiserum.

FIG. 5A presents a diagram showing positions of the cdt genes and degeneration primers. FIG. 5B presents a photograph showing PCR results.

FIG. 7A to C present photographs showing Giemsa staining and microscopic observation (×100) of HeLa cells 48 hours after addition of a crude toxin solution and the anti-Ch-rCdtB serum. FIGS. 7D to F show measurement of the DNA content in HeLa cells after 48 hours by a flow cytometer. A and D, PBS; B and E, crude toxin solution (four times greater than CD50); F and G, crude toxin solution (four times greater than CD50) and anti-Ch-rCdtB serum.

FIG. 12 presents a photograph showing PCR results of using specific primers for detection of the *C. hyointestinalis* Thai-type cdtB gene.

FIG. 15 presents a photograph showing the result of multiplex PCR based on the cdt genes of *C. jejuni, C. coli, C. fetus*, and *C. hyointestinalis.*

FIG. 16 presents a photograph showing the result of multiplex PCR based on the cdt genes of *C. jejuni, C. coli, C. fetus, C. hyointestinalis, C. lari*, and *C. upsaliensis.*

FIG. 17 presents a diagram showing an alignment of the cdtB gene of the *C. hyointestinalis* Thai-derived Ch022 (SEQ ID NO: 5) and ATCC (SEQ ID NO: 1) strains, and positions of the primers.

MODE FOR CARRYING OUT THE INVENTION

Figure 1:
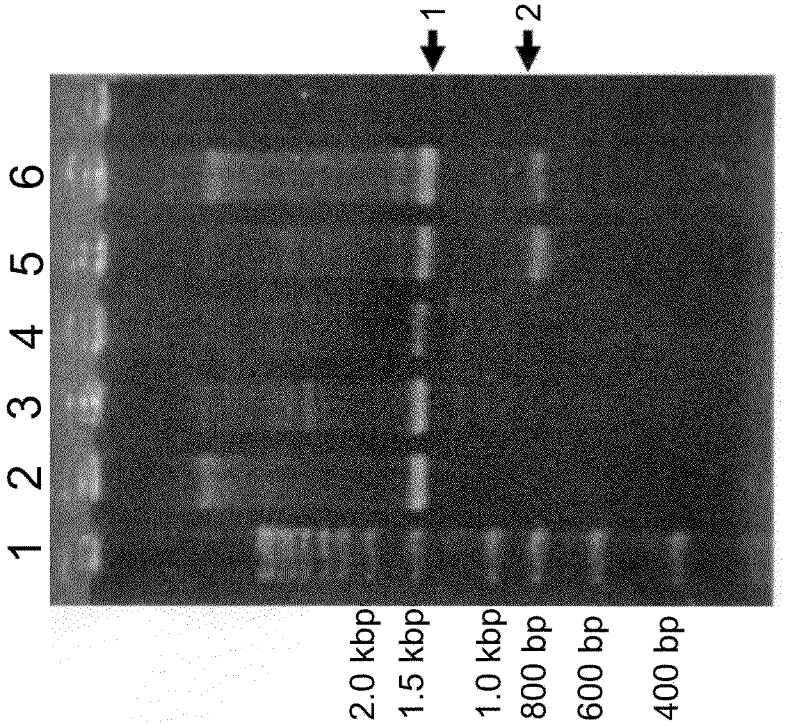
FIG. 1 presents a photograph showing PCR results for the Thai-derived *C. hyointestinalis* Ch022 strain and other *Campylobacter* bacteria using common primers that can amplify the cdtB gene of *C. jejuni, C. coli*, and *C. fetus.*

Herein, the phrase "cytolethal distending toxins" (CDTs or CLDTs) refers to toxic factors belonging to the group of proteinaceous type A-B holotoxins. The cytolethal distending toxin has a subunit structure consisting of three subunits A, B, and C. It is believed that subunit B is the active site unit of the toxin and subunits A and B are involved in cell adhesion. When the toxin acts on cells, it causes cell deformation such as cell swelling, and finally leads to cell death. Cell deformation such as cell swelling is also observed when heat-labile enterotoxin (LT), which is produced by toxigenic *E. coli*, or the like is experimentally allowed to act on cells. When the toxin is removed, however, the cells recover and survive. In contrast, cells do not recover but instead are killed, even when CDT is removed.

The term "polynucleotide" as used herein refers to a polymer made up of a number of bases or base pairs consisting of ribonucleotides or deoxyribonucleotides. Polynucleotides include single-stranded DNAs and double-stranded DNAs. Polynucleotides herein may include both unmodified, naturally-occurring polynucleotides and modified polynucleotides. Tritylated bases and special bases, such as inosine, are examples of modified bases.

The term "polypeptide" as used herein refers to a polymer made up of a number of amino acids. Therefore, oligopeptides and proteins are also included within the concept of polypeptides. Polypeptides include both unmodified, naturally-occurring polypeptides and modified polypeptides. Examples of polypeptide modifications include acetylation; acylation; ADP-ribosylation; amidation; covalent binding with flavin; covalent binding with heme moieties; covalent binding with nucleotides or nucleotide derivatives; covalent binding with lipids or lipid derivatives; covalent binding with phosphatidylinositols; cross-linkage; cyclization; disulfide bond formation; demethylation; covalent cross linkage formation; cystine formation pyroglutamate formation; formylation; g-carboxylation; glycosylation; GPI-anchor formation; hydroxylation; iodination; methylation; myristoylation; oxidation; proteolytic treatment; phosphorylation; prenylation; racemization; selenoylation; sulfation; transfer RNA-mediated amino acid addition to a protein such as arginylation; ubiquitination; and the like. The term "isolate" as used herein refers to a substance (for example, a polynucleotide or polypeptide) removed from its original environment (for example, the natural environment for a naturally-occurring substance) and "artificially" changed from its natural state. "Isolated" compounds refer to compounds including those present in samples that are substantially abundant with a subject compound, and/or those present in samples wherein the subject compound is partly or substantially purified. Herein, the term "substantially purified" refers to compounds (for example, polynucleotides or polypeptides) that are isolated from the natural environment and in which at least 60%, preferably 75%, and most preferably 90% of the other components associated with the compound in nature are absent.

The term "mutation" as used herein refers to changes to the amino acids of an amino acid sequence, or changes to the bases in a nucleotide sequence (that is, substitution, deletion, addition, or insertion of one or more amino acids or nucleotides). Therefore, the term "mutant" as used herein refers to amino acid sequences wherein one or more amino acids are changed, or nucleotide sequences wherein one or more nucleotides are changed. Nucleotide sequence changes in the mutant may change the amino acid sequence of the polypeptide encoded by the standard polynucleotide, or not. The mutant may be one that exists in nature, such as an allelic mutant, or one not yet identified in nature. The mutant may be conservatively altered, wherein substituted amino acids retain structural or chemical characteristics similar to those of the original amino acid. Rarely, mutants may be substituted non-conservatively. Computer programs known in the art, such as DNA STAR software, can be used to decide which or how many amino acid residues to substitute, insert, or delete without inhibiting biological or immunological activity.

"Deletion" is a change to either an amino acid sequence or nucleotide sequence, wherein one or more amino acid residues or nucleotide residues are missing as compared with the amino acid sequence of a naturally occurring cytolethal distending toxin polypeptide, or a nucleotide sequence encoding the same.

"Insertion" or "addition" is a change to either an amino acid sequence or nucleotide sequence, wherein one or more amino acid residues or nucleotide residues are added as compared with the amino acid sequence of a naturally-occurring cytolethal distending toxin polypeptide, or a nucleotide sequence encoding the same.

"Substitution" is a change to either an amino acid sequence or nucleotide sequence, wherein one or more amino acid residues or nucleotide residues are changed to different amino acid residues or nucleotide residues, as compared to the amino acid sequence of a naturally-occurring cytolethal distending toxin polypeptide, or a nucleotide sequence encoding the same.

The term "hybridize" as used herein refers to a process wherein a nucleic acid chain binds to its complementary chain through the formation of base pairs.

Herein, the term "detection" means both qualitative and quantitative measurements. "Quantitation" also refers to semiquantitative measurement.

<Polynucleotides>

The present invention provides polynucleotides encoding the cytolethal distending toxin of *Campylobacter hyointestinalis*. The present inventors identified the nucleotide sequence of a polynucleotide encoding the cytolethal distending toxin of the *Campylobacter hyointestinalis* strain from American Type Culture Collection (ATCC), and the polynucleotide is included in the present invention designated as SEQ ID NO: 1. The amino acid sequences of the three polypeptides encoded by the polynucleotide are shown in SEQ ID NOs: 2 to 4. The sequences of SEQ ID NOs: 2, 3, and 4 are the amino acid sequences of CdtA, CdtB, and CdtC, respectively.

Furthermore, the present inventors identified the nucleotide sequence of a polynucleotide encoding the cytolethal distending toxin of a clinically isolated *Campylobacter hyointestinalis* stain as shown in SEQ ID NO: 5. The amino acid sequences of the three polypeptides encoded by the polynucleotide are shown in SEQ ID NOs: 6 to 8. The sequences of SEQ ID NOs: 6, 7, and 8 are the amino acid sequences of CdtA, CdtB, and CdtC, respectively.

The polynucleotides of the present invention include polynucleotides encoding polypeptides comprising the amino acid sequences of SEQ ID NOs: 2 to 4; polynucleotides comprising any one of the coding regions of the nucleotide sequence of SEQ ID NO: 1, specifically any one of the nucleotide sequences of positions 962 to 1600, positions 1601 to 2425, and positions 2425 to 3177 in the nucleotide sequence of SEQ ID NO: 1; and polynucleotides that comprise a nucleotide sequence different from the nucleotide sequence of SEQ ID NO: 1 but encode polypeptides comprising the amino acid sequences of SEQ ID NOs: 2 to 4 due to genetic code degeneracy.

The polynucleotides of the present invention also include polynucleotides encoding polypeptides comprising the amino acid sequences of SEQ ID NOs: 6 to 8; polynucleotides comprising any one of the coding regions of the nucleotide sequence of SEQ ID NO: 5, specifically any one of the nucleotide sequences of positions 1059 to 1835, positions 1853 to 2656, and positions 2666 to 3202 in the nucleotide sequence of SEQ ID NO: 5; and polynucleotides that comprise a nucleotide sequence different from the nucleotide sequence of SEQ ID NO: 5 but encode polypeptides comprising the amino acid sequences of SEQ ID NOs: 6 to 8 due to genetic code degeneracy.

The polynucleotides of the present invention further include polynucleotides that encode polypeptides functionally equivalent to polypeptides encoded by the above polynucleotides and have a nucleotide sequence with an identity of at least 40% or higher, preferably 60% or higher, more preferably 80% or higher, even more preferably 90% or higher, still more preferably 95% or higher, yet more preferably 97% or higher (for example, 98 to 99%) to the entire sequence of the polynucleotide. The nucleotide sequence identity can be determined, for example, using the algorithm BLAST by Karlin and Altschul (Proc. Natl. Acad. Sci. USA 87:2264-2268, 1990; Proc. Natl. Acad. Sci. USA 90:5873-5877, 1993). A program called BLASTN has been developed based on this algorithm (Altschul et al. J. Mol. Biol. 215:403-410, 1990). When nucleotide sequences are analyzed by BLASTN, the parameters are set, for example, as follows: score=100; wordlength=12. When BLAST and Gapped BLAST programs are used, default parameters are used for each program. The specific techniques for these analytical methods are known (http://www.ncbi.nlm.nih.gov.). The polynucleotides of the present invention include polynucleotides having nucleotide sequences complementary to the above polynucleotide sequences.

The polynucleotides of the present invention can be obtained through standard cloning and screening methods from natural sources, such as genomic DNA in bacterial cells. Alternatively, the polynucleotides can be obtained from cDNA libraries derived from mRNA in bacterial cells. The polynucleotides can also be synthesized using known techniques that are commercially available.

Polynucleotides having nucleotide sequences with significant homology to the polynucleotide sequences identified by the present inventors (e.g., SEQ ID NOs: 1 and 5) can be prepared, for example, using hybridization techniques (Current Protocols in Molecular Biology edit. Ausubel et al. (1987) Publish. John Wiley & Sons Section 6.3-6.4) and gene amplification techniques (PCR) (Current protocols in Molecular Biology edit. Ausubel et al. (1987) Publish. John Wiley & Sons Section 6.1-6.4). Specifically, based on the polynucleotide sequences identified by the present inventors (e.g., SEQ ID NOs: 1 and 5) or portions thereof, DNA highly homologous to the sequences can be isolated using known hybridization techniques. Alternatively, polynucleotides highly homologous to the polynucleotide sequences can be isolated by gene amplification techniques, using primers designed based on portions of the polynucleotide sequences identified by the present inventors (e.g., SEQ ID NOs: 1 and 5). Thus, the present invention includes polynucleotides that hybridize to the polynucleotide having the nucleotide sequence of SEQ ID NO: 1 or 5 under stringent conditions. Those skilled in the art can select suitable stringent hybridization conditions. For example, hybridization can be carried out by overnight prehybridization at 42° C. in a hybridization solution containing 25% formamide (or 50% formamide for more stringent conditions), 4×SSC, 50 mM Hepes (pH 7.0), 10×Denhardt's solution, and 20 μg/ml denatured salmon sperm DNA; followed by addition of a labeled probe and hybridization by overnight incubation at 42° C. Post-hybridization wash may be carried out under the washing solution and temperature conditions of "1×SSC, 0.1% SDS, 37° C." or such, "0.5×SSC, 0.1% SDS, 42° C." or such for more stringent conditions, or "0.2×SSC, 0.1% SDS, 65° C." for yet more stringent conditions. As the stringency of the hybridization washing condition increases as described above, isolation of DNAs having higher homology to the probe sequence is expected. However, the above combinations of SSC, SDS, and temperature condition are only exemplary. Those skilled in the art can achieve the same stringency described above by appropriately combining the above or other factors that determine the degree of hybridization stringency, for example, probe concentration and length, and reaction time for hybridization.

Polynucleotides including nucleotide sequences with significant homology to the polynucleotide sequences identified by the present inventors can also be prepared by methods for introducing mutations into the nucleotide sequences of SEQ ID NOs: 1 and 5 (for example, site directed mutagenesis (Current Protocols in Molecular Biology edit. Ausubel et al. (1987) Publish. John Wiley & Sons Section 8.1-8.5)). Such polynucleotides may also be generated by naturally-occurring mutations. The present invention includes polynucleotides encoding the polypeptides having an amino acid sequence wherein one or more amino acids is substituted, deleted, inserted and/or added in the amino acid sequences of SEQ ID NOs: 2 to 4 or 6 to 8 due to such nucleotide sequence mutations.

When the polynucleotides of the present invention are used to produce the polypeptides of the present invention, the polynucleotides include coding sequences for the mature polypeptides or fragments thereof alone, or coding sequences for the mature polypeptides or fragments thereof which are located in the same reading frame as other coding sequences (for example, leader or secretory sequence, pre-, pro-, or prepro-protein sequence, or sequences encoding other fusion peptide portions). For example, marker sequences that facilitate purification of fusion polypeptides may be encoded. In this embodiment of the present invention, preferred examples of marker sequences include, for example, hexa-histidine peptide or Myc tag which is provided by pcDNA3.1/Myc-His vector (Invitrogen) and described in Gentz et al., Proc. Natl. Acad. Sci. USA (1989) 86:821-824. The polynucleotide may also include 5' and 3' non-coding sequences, for example, transcribed but untranslated sequences, splicing and polyadenylation signals, ribosome-binding site, and mRNA-stabilizing sequence.

<Polypeptide>

The present invention provides polypeptides of the cytolethal distending toxin of *Campylobacter hyointestinalis* identified by the present inventors. The present invention also provides polypeptides functionally equivalent to the polypeptides identified by the present inventors. Herein, "functionally equivalent" means that a polypeptide of interest has equivalent characteristics of cytolethal distending toxin to those of the polypeptides identified by the present inventors.

Introducing mutations into the amino acid sequence of proteins is one means for preparing polypeptides functionally equivalent to the polypeptides identified by the present inventors. Such methods include, for example, site-directed mutagenesis (Current Protocols in Molecular Biology, edit. Ausubel et al. (1987) Publish. John Wiley & Sons Section 8.1-8.5). Amino acid mutation in polypeptides may also occur in nature. The present invention includes mutant proteins, regardless of whether artificially or naturally produced, that include the amino acid sequence identified by the present inventors (e.g., SEQ ID NOs: 2 to 4 and 6 to 8), wherein one or more amino acid residues are altered by substitution, deletion, insertion, and/or addition, yet which are functionally equivalent to the polypeptides identified by the present inventors.

From the viewpoint of conserving the protein's functions, an amino acid residue used for substitution preferably has properties similar to the substituted amino acid residue (conservative substitution). For example, Ala, Val, Leu, Ile, Pro, Met, Phe, and Trp are all classified as non-polar amino acids, and are considered to have similar properties. Further, examples of uncharged amino acids are Gly, Ser, Thr, Cys, Tyr, Asn, and Gln. Moreover, examples of acidic amino acids are Asp and Glu, and those of basic amino acids are Lys, Arg, and His.

There are no limitations as to the number and site of the amino acid mutations of these polypeptides, as long as the mutated polypeptides retain a function of the original polypeptide. The number of mutations may be typically less than 10%, preferably less than 5%, and more preferably less than 1% of the total amino acid residues.

Other means for preparing polypeptides functionally equivalent to the polypeptides identified by the present inventors include methods that utilize hybridization techniques or gene amplification techniques. More specifically, those skilled in the art can obtain polypeptides functionally equivalent to the polypeptides determined by the present inventors by isolating highly homologous DNAs from DNA samples derived from organisms of the same or different species using hybridization techniques (Current Protocols in Molecular Biology, edit. Ausubel et al. (1987) Publish. John Wiley & Sons Section 6.3-6.4) based on the DNA sequence encoding the polypeptides identified by the present inventors (SEQ ID NO: 1 and 5). Thus, such polypeptides encoded by DNAs hybridizing to the DNAs encoding the polypeptides identified by the present inventors, which are functionally equivalent to the polypeptides identified by the present inventors, are also included in the polypeptides of this invention.

Those skilled in the art can select suitable stringent hybridization conditions for isolation of a DNA encoding a polypeptide functionally equivalent to the polypeptides identified by the present inventors. For example, hybridization can be carried out by overnight prehybridization at 42° C. in a hybridization solution containing 25% formamide (or 50% formamide for more stringent conditions), 4×SSC, 50 mM Hepes (pH 7.0), 10×Denhardt's solution, and 20 μg/ml denatured salmon sperm DNA; followed by addition of a labeled probe and hybridization by overnight incubation at 42° C. Post-hybridization wash may be carried out under the washing solution and temperature conditions of "1×SSC, 0.1% SDS, 37° C." or such, "0.5×SSC, 0.1% SDS, 42° C." or such for more stringent conditions, or "0.2×SSC, 0.1% SDS, 65° C." for yet more stringent conditions. As the stringency of the hybridization washing condition increases as described above, isolation of DNAs having higher homology to the probe sequence is expected. However, the above-mentioned combinations of SSC, SDS, and temperature conditions are only examples, and those skilled in the art can achieve the same stringencies as described above by appropriately combining the above-mentioned factors or other parameters that determine hybridization stringency (for example, probe concentration, probe length, reaction time of hybridization, etc.).

The polypeptides encoded by DNAs isolated using such hybridization techniques normally have amino acid sequences highly homologous to the polypeptides identified by the present inventors. Herein, high homology indicates sequence identity of at least 40% or more, preferably 60% or more, more preferably 80% or more, still more preferably 90% or more, further still more preferably at least 95% or more, and yet more preferably at least 97% or more (for example, 98% to 99%). Homology of amino acid sequences can be determined, for example, using the algorithm BLAST of Karlin and Altschul (Proc. Natl. Acad. Sci. USA 87: 2264-2268 (1990); Proc. Natl. Acad. Sci. USA 90: 5873-5877 (1993)). Based on this algorithm, a program referred to as BLASTX has been developed (Altschul et al., J. Mol. Biol. 215: 403-410 (1990)). When amino acid sequences are analyzed using BLASTX, parameters are set, for example, at score=50 and word length=3. When using BLAST and Gapped BLAST programs, default parameters of each program are used. Specific techniques for these analytical methods are well known in the art.

Gene amplification techniques (PCR) (Current Protocols in Molecular Biology, edit. Ausubel et al. (1987) Publish. John Wiley & Sons Section 6.1-6.4) can be utilized to obtain polypeptides functionally equivalent to the polypeptides isolated by the present inventors, based on DNA fragments isolated as DNAs highly homologous to the DNA sequences encoding the polypeptides isolated by the present inventors. This can be achieved by designing primers based on a part of the DNA sequence encoding the polypeptides identified by the present inventors (SEQ ID NOs: 1 and 5).

<Polypeptide Fragments>

The present invention also provides fragments of the polypeptides of this invention. These fragments are polypeptides having amino acid sequences that are partly, but not entirely, identical to the above polypeptides of this invention. The polypeptide fragments of this invention usually include eight amino acid residues or more, and preferably twelve amino acid residues or more (for example, 15 amino acid residues or more). Examples of preferred fragments include truncated polypeptides, such as amino acid sequences that lack a series of amino acid residues including either the amino terminus or carboxyl terminus, or two series of amino acid residues, one including the amino terminus and the other including the carboxyl terminus. Furthermore, fragments featuring structural or functional characteristics are also preferable, and include those having α-helix and .α-helix forming regions, β-sheet and β-sheet forming regions, turn and turn-forming regions, coil and coil-forming regions, hydrophilic regions, hydrophobic regions, α-amphipathic regions, β-amphipathic regions, variable regions, surface forming regions, substrate-binding regions, and high antigenicity index regions. Biologically active fragments are also preferred. Biologically active fragments mediate the activities of the polypeptides of this invention, and include those that have a similar or improved activity, or a reduced undesirable activity. For example, fragments that are antigenic or immunogenic in animals, especially humans, are included. These polypeptide fragments preferably retain a biological activity, such as antigenicity, of the polypeptides of this invention. Mutants of specific sequences or fragments also constitute an aspect of this invention. Preferred mutants are those that differ from the subject polypeptide due to replacement with conservative amino acids, namely, those in which a residue is substituted with another residue of similar properties. Typical substitutions are those between Ala, Val, Leu, and Ile; Ser and Thr; acidic residues Asp and Glu, Asn, and Gln; basic residues Lys and Arg; or aromatic residues Phe and Tyr.

<Production of Polypeptides>

Polypeptides of this invention may be produced by any appropriate method. Such polypeptides include isolated naturally-occurring polypeptides, and polypeptides which are produced by gene recombination, synthesis, or by a combination thereof. Procedures for producing these polypeptides are well known in the art. Recombinant polypeptides may be prepared, for example, by transferring a vector, inserted with a polynucleotide of the present invention, into an appropriate host cell, and purifying the polypeptide expressed within the resulting transformant. On the other hand, naturally occurring polypeptides can be prepared, for example, using affinity columns wherein antibodies against a polypeptide of this invention (described below) are immobilized (Current Protocols in Molecular Biology, edit. Ausubel et al. (1987) Publish. John Wiley & Sons, Section 16.1-16.19). Antibodies for affinity purification may be either polyclonal or monoclonal antibodies. The polypeptides of this invention may be also prepared by in vitro translation methods (for example, see "On the fidelity of mRNA translation in the nuclease-treated rabbit reticulocyte lysate system." Dasso, M. C. and Jackson, R. J. (1989) NAR 17: 3129-3144), and such. The polypeptide fragments of this invention can be produced, for example, by cleaving the polypeptides of the present invention with appropriate peptidases.

<Probes and Primers>

The present invention provides polynucleotides with a chain length of at least 15 nucleotides or 20 nucleotides, for example, polynucleotides with a chain length of 15 to 100 nucleotides, 20 to 100 nucleotides, 15 to 35 nucleotides, or 20 to 35 nucleotides, which are complementary to a polynucleotide identified by the present inventors (e.g., a polynucleotide having the nucleotide sequence of SEQ ID NO: 1 or a complementary strand thereof, and a polynucleotide having the nucleotide sequence of SEQ ID NO: 5 or a complementary strand thereof). Herein, the term "complementary strand" is defined as the other strand of a double-stranded nucleic acid composed of A:T (A:U in case of RNA) and G:C base pairs. In addition, the term "complementary" encompasses not only complete matching within a continuous region of at least 15 sequential nucleotides, but also homology of at least 70%, preferably at least 80%, more preferably 90%, and most preferably 95% or higher within that region. Homology may be determined using an algorithm described herein. Probes and primers for detection or amplification of the polynucleotides of the present invention are included in these polynucleotides. Typical polynucleotides used as primers are 15 to 100 nucleotides long, and preferably 15 to 35 nucleotides long. Alternatively, polynucleotides used as probes are nucleotides at least 15 nucleotides in length, and preferably at least 30 nucleotides. They include at least a portion or an entire sequence of a DNA of the present invention. When using the nucleotides of the present invention as primers, the nucleic acid amplification reaction is not particularly limited, as long as a desired amplification product can be obtained. For example, the reaction may be selected from DNA amplification reactions such as polymerase chain reaction (PCR), ICAN, LAMP, SDA, and LCR, and RNA amplification reactions such as NASBA. A preferred method is PCR.

In one embodiment, such nucleotides are those specific to a DNA encoding a polypeptide of the present invention. The term "specific" refers to hybridizing under normal hybridization conditions, preferably stringent conditions, with DNA encoding a certain polypeptide, but not with DNAs encoding other polypeptides.

Specific examples of primers for amplifying a portion of the polynucleotides identified by the present inventors include the primers of (i) and (ii) below, which are described in the Examples herein.

(i) the primer pair of SEQ ID NOs: 24 and 25 for amplifying the genomic DNA encoding a cytolethal distending toxin of *Campylobacter hyointestinalis*, or a primer pair capable of amplifying the same genomic DNA region amplified by the primer pair of SEQ ID NOs: 24 and 25; and (ii) the primer pair of SEQ ID NOs: 18 and 19 for amplifying the genomic DNA encoding a cytolethal distending toxin of *Campylobacter hyointestinalis*, or a primer pair capable of amplifying the same genomic DNA region amplified by the primer pair of SEQ ID NOs: 18 and 19.

As described above, the nucleic acid amplification reaction applicable to the primers of the present invention is not particularly limited, as long as it yields desired amplification products. For example, the reaction can be selected from DNA amplification reactions such as PCR (polymerase chain reaction), ICAN, LAMP, SDA, and LCR, and RNA amplification reactions such as NASBA. A preferred method is PCR. Based on the above primers, those skilled in the art can design mutant primers suitable for nucleic acid amplification methods to be performed. Such mutant primers can be synthetically prepared. It can be readily assessed whether mutant primers can amplify the same genomic DNA region as amplified with the original primers, by conducting a nucleic acid amplification reaction using the mutant primers and analyzing the amplification products.

These primers can be preferably used to detect the presence of *Campylobacter hyointestinalis* in test samples.

<Production of Vectors, Host Cells, and Polypeptides>

The present invention also provides methods for producing vectors carrying polynucleotides of the present invention, host cells retaining the polynucleotides or said vectors of the present invention, and polypeptides of the present invention utilizing said host cells.

The vectors of the present invention are not limited, as long as the DNAs inserted in the vectors are stably retained. For example, pBluescript vector (Stratagene) is a preferable cloning vector when using *E. coli* as a host. When using vectors to produce the polypeptides of the present invention, expression vectors are particularly useful. These expression vectors are not specifically limited, as long as they express polypeptides in vitro, in *E. coli*, in cultured cells, or in vivo. However, preferred examples include the pBEST vector (ProMega) for in vitro expression, the pET vector (Invitrogen) for expression in *E. coli*, the pME18S-FL3 vector (GenBank Accession No. AB009864) for expression in cultured cells, and the pME18S vector (Mol. Cell Biol. 8:466-472(1988)) for in vitro expression, and such. A DNA of the present invention can be inserted into a vector by conventional methods, for example, by a ligase reaction using restriction enzyme sites (Current Protocols in Molecular Biology, edit. Ausubel, et al., (1987) Publish. John Wiley & Sons, Section 11.4-11.11).

Host cells into which the vectors of the present invention are introduced are not specifically limited, and various host cells can be used according to the objectives of the present invention. For example, bacterial cells (e.g. *Streptococcus, Staphylococcus, E. coli, Streptomyces, Bacillus subtilis*), fungal cells (e.g. yeast, *Aspergillus*), insect cells (e.g. *Drosophila* S2, *Spodoptera* SF9), animal cells (e.g. CHO, COS, HeLa, C127, 3T3, BHK, HEK293, Bowes melanoma cell), and plant cells are examples of cells for expressing polypeptides. The transfection of a vector into a host cell can be carried out by conventional methods, such as calcium phosphate precipitation methods, electroporation methods (Current protocols in Molecular Biology, edit., Ausubel et al., (1987) Publish. John Wiley & Sons, Section 9.1-9.9), Lipofectamine methods (GIBCO-BRL), microinjection methods, and such.

In host cells, appropriate secretion signals can be incorporated into a polypeptide of interest in order to facilitate the secretion of an expressed polypeptide into the lumen of the endoplasmic reticulum, into the cavity around a cell, or into the extracellular environment. These signals may be endogenous signals or signals from a species different from the target polypeptide.

When a polypeptide of the present invention is secreted into culture medium, this culture medium is collected to collect the polypeptide of the present invention. When a polypeptide of the present invention is produced intracellularly, the cells are first lysed, and the polypeptide is then collected.

In order to collect and purify a polypeptide of the present invention from a recombinant cell culture, methods known in the art can be used, including ammonium sulfate or ethanol precipitation, acid extraction, anionic or cationic exchange chromatography, phosphocellulose chromatography, hydrophobic interaction chromatography, affinity chromatography, hydroxylapatite chromatography, and lectin chromatography.

<Antibodies>

The present invention provides antibodies that bind to a polypeptide of the present invention. Herein, the term "antibodies" refers to polyclonal antibodies, monoclonal antibodies, chimeric antibodies, single-stranded antibodies, humanized antibodies, and Fab fragments including Fab or other products of an immunoglobulin expression library.

A polypeptide of the present invention, fragments and derivatives thereof, and cells expressing them can be used as an immunogen for producing antibodies that bind to the polypeptide of the present invention. Such antibodies are preferably immunospecific to the polypeptide of the present invention. "Immunospecific" means that the antibody has substantially higher affinity to the polypeptide of the present invention than to other polypeptides. Furthermore, more preferably, antibodies of the present invention include antibodies having an activity of neutralizing the cytolethal distending toxin of *C. hyointestinalis.*

The antibodies binding to a polypeptide of the present invention can be prepared by methods known to those skilled in the art. For example, a polyclonal antibody can be obtained by administering a polypeptide of the present invention or a GST-fusion protein thereof to small animals such as rabbits to obtain serum. Polyclonal antibodies are prepared by purifying the serum by ammonium sulfate precipitation; a protein A or protein G column; DEAE ion exchange chromatography; an affinity column in which the polypeptide of the present invention is coupled; and such. On the other hand, monoclonal antibodies, for example, can be prepared by administering a polypeptide of the present invention to small animals such as mice, and their spleens are subsequently extirpated and ground down to separate the cells. The cells are then fused with mouse myeloma cells using reagents such as polyethylene glycol, and clones that produce antibodies binding to the polypeptide of the present invention are selected from these fused cells (hybridomas). The obtained hybridomas are then transplanted into mice peritoneal cavities, and ascites are collected from the mice. The monoclonal antibodies can be prepared by purifying the ascites using, for example, ammonium sulfate precipitation; a protein A or protein G column; DEAE ion exchange chromatography; an affinity column in which the polypeptides of the present invention are coupled; and such.

The antibodies of the present invention can also be used to detect and purify the polypeptides of the present invention in test samples.

<Detection of the Presence of *Campylobacter* Bacteria in Test Samples>

The present invention provides methods for detecting *Campylobacter* bacteria in test samples. Detection of the presence of *Campylobacter* bacteria in test samples is useful for various purposes such as diagnosis of *Campylobacter* infection, rapid test of food contaminated with *Campylobacter hyointestinalis*, validation in each step of food processing, and identification of bacteria responsible for food poisoning outbreak.

In one embodiment, the detection method of the present invention is a method for detecting the presence of one or more *Campylobacter* bacteria in a test sample, which comprises the steps of: (a) conducting a nucleic acid amplification reaction on the test sample using a mixture of primer pair(s) specific to a genomic DNA encoding a cytolethal distending toxin of a *Campylobacter* bacterium; and (b) determining the presence of *Campylobacter* bacteria based on the presence or molecular weight of an fragment amplified from the genomic DNA encoding the cytolethal distending toxin of the *Campylobacter* bacterium.

In the present invention, the "primers specific to the genomic DNA" are not limited to primers specific to a genomic DNA region encoding the cytolethal distending toxin of a *Campylobacter* bacterium, but also include primers specific to an mRNA region corresponding to the genomic DNA region.

Oligonucleotide primers that specifically hybridize with the genomic DNA encoding the cytolethal distending toxin of a *Campylobacter* bacterium can be prepared by the methods described above. The primer binding sequence segment is not particularly limited; however, it may be designed to have appropriate restriction sites that allow restriction enzyme cleavage of the primer segment after PCR amplification. There is no particular limitation on the length of the primer binding sequence segment, and the length is about 20 to 50 nucleotides, preferably about 20 to 30 nucleotides. Furthermore, the primers may be labeled at the 5' end with radiolabels, fluorescent labels, or the like, so that the single-stranded DNAs can be isolated by electrophoresis or such after PCR amplification. Alternatively, to prepare RNA molecules, the 5'-end primers may be designed to have an appropriate promoter, for example, a T7 promoter sequence, in order to allow transcription of the DNA molecule into an RNA molecule.

The methods of the present invention may further comprise the step of identifying *Campylobacter* bacterial species by the PCR-restriction fragment length polymorphism (PCR-RFLP) method. In the PCR-RFLP method, PCR-amplified DNAs are digested with various restriction enzymes and then polymorphism is detected based on the length of the resulting fragments. The cdt gene sequences of *Campylobacter* bacteria, which are to be detected in the present invention, vary depending on the bacterial species. Thus, the PCR-RFLP method can be used to identify bacterial species.

In this step, sites that have different sequences depending on the bacterial species (polymorphic sites) are first determined by sequence comparison, and then restriction enzymes that recognize the polymorphic sites in any of the bacterial species are selected. If such restriction enzymes already exist, whether bacterial species that have the polymorphic sites are present in a sample containing multiple *Campylobacter* bacteria species can be determined by carrying out PCR that targets the cdt genes, digesting the resulting PCR products with the restriction enzymes, and comparing the length of the fragments by electrophoresis. Those skilled in the art can identify sites with different sequences by comparing known *Campylobacter* bacterial cdt genes with the *C. hyointestinalis* cdt genes provided by the present invention, and select appropriate restriction enzymes that recognize the sites.

The present invention also provides primers that are preferably used in methods for polymorphism detection based on the length of fragments obtained from digesting DNAs amplified by nucleic acid amplification methods with various restriction enzymes, including PCR-RFLP.

An example of applying the PCR-RFLP method in the present invention is amplifying fragments by the pair of primers comprising the sequences of SEQ ID NOs: 18 and 19 (primers used in the Examples herein: cdtB commonU and cdtB commonR), and digesting the fragments with restriction enzyme EcoRI, XbaI, HindIII, or Sau3AI alone or a combination thereof; and bacterial species can be identified by electrophoresis.

More specifically, the detection methods of the present invention include, for example, methods for simultaneously detecting the presence of one or more *Campylobacter* bacterial species in a test sample, which comprise the step of performing nucleic acid amplification reaction on the test sample using any one or more of the primer pairs below which are specific to genomic DNA encoding a *Campylobacter* cytolethal distending toxin: "(i) the primer pair of SEQ ID NOs: 24 and 25 for amplifying the genomic DNA encoding a cytolethal distending toxin of *Campylobacter hyointestinalis*, or a primer pair capable of amplifying the same genomic DNA region amplified by the primer pair of SEQ ID NOs: 24 and 25", "(ii) the primer pair of SEQ ID NOs: 18 and 19 for amplifying the genomic DNA encoding a cytolethal distending toxin of *Campylobacter hyointestinalis*, or a primer pair capable of amplifying the same genomic DNA region amplified by the primer pair of SEQ ID NOs: 18 and 19", "(iii) the primer pair of SEQ ID NOs: 32 and 33 for amplifying the genomic DNA encoding a cytolethal distending toxin of *Campylobacter* upsaliensis, or a primer pair capable of amplifying the same genomic DNA region amplified by the primer pair of SEQ ID NOs: 32 and 33; and "(iv) the primer pair of SEQ ID NOs: 34 and 35 for amplifying the genomic DNA encoding a cytolethal distending toxin of *Campylobacter lari*, or a primer pair capable of amplifying the same genomic DNA region amplified by the primer pair of SEQ ID NOs: 34 and 35.

The above-described methods are methods that detect bacteria by amplifying regions specific to the genomic DNA or mRNA of *C. hyointestinalis, C. upsaliensis*, and *C. lari* cdtB.

Primers used in the above-described methods include, for example, the "primer pair comprising the sequences of SEQ ID NOs: 24 and 25 (primers used in the Examples herein: ChspBU7 and ChspBR7)" and the "primer pair comprising the sequences of SEQ ID NOs: 18 and 19 (primers used in the Examples herein: cdtB commonU and cdtB commonR)" for *C. hyointestinalis*, without being limited thereto. Any other sequences may be used as long as they are primer pairs comprising two polynucleotides that can specifically bind to the genomic DNA or mRNA of *C. hyointestinalis* cdtB, and amplify the region amplified using the genomic DNA of *C. hyointestinalis* cdtB as template and the "primer pair comprising the sequences of SEQ ID NOs: 24 and 25" or the "primer pair comprising the sequences of SEQ ID NOs: 18 and 19", or the corresponding mRNA region. Herein, "specifically binds" means excluding incidental or non-specific binding from the "binding".

FIG. 17 shows sites in the cdtB gene to which the above-described primers for detecting *C. hyointestinalis* bind.

Alternatively, as for *C. upsaliensis*, the primers representatively include the "primer pair comprising the sequences of SEQ ID NOs: 32 and 33 (primers used in the Examples herein: CupspBU3 and CupspBR4)", but are not limited to these sequences. Any other sequences may be used as long as they are primer pairs that can amplify the region amplified using the genomic DNA of *C. fetus* cdtB as template and the "primer pair comprising the sequences of SEQ ID NOs: 32 and 33", or the corresponding mRNA region.

Furthermore, as for *C. fetus*, the primers representatively include the "primer pair comprising the sequences of SEQ ID NOs: 34 and 35 (primers used in the Examples herein: ClaspBU4 and ClaspBR4)", but are not limited to these sequences. Any other sequences may be used as long as they are primer pairs that can amplify the region amplified using the genomic DNA of *C. fetus* cdtB as template and the "primer pair comprising the sequences of SEQ ID NOs: 34 and 35", or the corresponding mRNA region.

In the methods of the present invention, the primer pairs of (i) to (iv) above may be used separately. Alternatively, multiple primer pairs can be used simultaneously in a single nucleic acid amplification reaction. The PCR method in which multiple PCR primers are used in a single reaction such as in the Examples herein is called "multiplex PCR". Thus, different bacterial species can be identified by electrophoresing the PCR products and determining the band size. The present invention provides methods for detecting *Campylobacter* bacteria by nucleic acid amplification, representatively including the above-described multiplex PCR, using primers and combinations thereof preferably used for amplifying different nucleic acid regions. In the present invention, there is no limitation on the type of nucleic acid amplification method, as long as it yields amplification products of interest. It is possible to select any type of known nucleic acid amplification reaction, for example, the polymerase chain reaction (PCR) method (including RT-PCR method), ICAN method, LAMP method, SDA method, LCR method, and NASBA method. The PCR method is a specific example of nucleic acid amplification method preferably used in the present invention. The methods of the present invention may be implemented as a quantitation method by real-time PCR or such.

In the methods of the present invention, a single nucleic acid amplification reaction can be performed using the primer pairs of (i) to (iv) above in combination with: "(v) the primer pair of SEQ ID NOs: 26 and 27 for amplifying the genomic DNA encoding a cytolethal distending toxin of *Campylobacter jejuni* (primers used in the Examples herein: Cj-CdtBU5 and Cj-CdtBR6), or a primer pair capable of amplifying the same genomic DNA region amplified by the primer pair of SEQ ID NOs: 26 and 27", "(vi) the primer pair of SEQ ID NOs: 28 and 29 for amplifying the genomic DNA encoding a cytolethal distending toxin of *Campylobacter coli* (primers used in the Examples herein: Cc-CdtBU5 and Cc-CdtBR5), or a primer pair capable of amplifying the same genomic DNA region amplified by the primer pair of SEQ ID NOs: 28 and 29, and "(vii) the primer pair of SEQ ID NOs: 30 and 31 for amplifying the genomic DNA encoding a cytolethal distending toxin of *Campylobacter fetus* (primers used in the Examples herein: Cf-CdtBU6 and Cf-CdtBR3), or a primer pair capable of amplifying the same genomic DNA region amplified by the primer pair of SEQ ID NOs: 30 and 31". Specifically, the present invention provides methods that can simultaneously detect the six *Campylobacter* bacterial species, *C. hyointestinalis, C. upsaliensis, C. lari, C. jejuni, C. fetus*, and *C. coli*, in a test sample. The present inventors demonstrated that the above-described six *Campylobacter* bacterial species can be simultaneously detected by nucleic acid amplification reaction that uses the above-described primers in combination. As demonstrated in the Examples herein, the methods of the present invention have very high specificity because they can detect *Campylobacter* bacteria of interest without erroneous detection of other *Campylobacter* bacterial species.

The methods of the present invention comprise, subsequent to the above-described step of nucleic acid amplification reaction using primers specific to the six *Campylobacter* bacterial species, the "step of determining the presence of *Campylobacter* bacteria based on the presence or molecular weight of fragments amplified from the genomic DNA or mRNA of *Campylobacter* bacterial cdt" or the "step of quantifying the amount of fragments amplified from the genomic DNA or mRNA of *Campylobacter* bacterial cdt".

The present invention provides kits to be used in the detection methods of the present invention. The kits comprise manuals in addition to the primer pairs. The kits may further comprise other materials, for example, fluorescent probes, intercalators, agents for preparing polynucleotides, and positive or negative primer pairs.

The first embodiment of the kits of the present invention includes kits comprising at least one of the following primer pairs:

"(i) the primer pair of SEQ ID NOs: 24 and 25 for amplifying the genomic DNA encoding a cytolethal distending toxin of *Campylobacter hyointestinalis*, or a primer pair capable of amplifying the same genomic DNA region amplified by the primer pair of SEQ ID NOs: 24 and 25", "(ii) the primer pair of SEQ ID NOs: 18 and 19 for amplifying the genomic DNA encoding a cytolethal distending toxin of *Campylobacter hyointestinalis*, or a primer pair capable of amplifying the same genomic DNA region amplified by the primer pair of SEQ ID NOs: 18 and 19", "(iii) the primer pair of SEQ ID NOs: 32 and 33 for amplifying the genomic DNA encoding a cytolethal distending toxin of *Campylobacter* upsaliensis, or a primer pair capable of amplifying the same genomic DNA region amplified by the primer pair of SEQ ID NOs: 32 and 33; and "(iv) the primer pair of SEQ ID NOs: 34 and 35 for amplifying the genomic DNA encoding a cytolethal distending toxin of *Campylobacter lari*, or a primer pair capable of amplifying the same genomic DNA region amplified by the primer pair of SEQ ID NOs: 34 and 35.

Alternatively, the above-described kits may further comprise: "(v) the primer pair of SEQ ID NOs: 26 and 27 for amplifying the genomic DNA encoding a cytolethal distending toxin of *Campylobacter jejuni* (primers used in the Examples herein: Cj-CdtBU5 and Cj-CdtBR6), or a primer pair capable of amplifying the same genomic DNA region amplified by the primer pair of SEQ ID NOs: 26 and 27", "(vi) the primer pair of SEQ ID NOs: 28 and 29 for amplifying the genomic DNA encoding a cytolethal distending toxin of *Campylobacter coli* (primers used in the Examples herein: Cc-CdtBU5 and Cc-CdtBR5), or a primer pair capable of amplifying the same genomic DNA region amplified by the primer pair of SEQ ID NOs: 28 and 29, and "(vii) the primer pair of SEQ ID NOs: 30 and 31 for amplifying the genomic DNA encoding a cytolethal distending toxin of *Campylobacter fetus* (primers used in the Examples herein: Cf-CdtBU6 and Cf-CdtBR3), or a primer pair capable of amplifying the same genomic DNA region amplified by the primer pair of SEQ ID NOs: 30 and 31". Thus, primers that are individually specific to each of the six species, *C. hyointestinalis, C. upsaliensis, C. lari, C. jejuni, C. fetus*, and *C. coli*, are all comprised in the kits of the present invention, allowing simultaneous detection of mixed infection with the above-described *Campylobacter* bacteria by multiplex PCR or the like.

Another embodiment of the detection methods of the present invention includes methods for detecting the presence of *Campylobacter hyointestinalis* in a test sample, which comprise the steps of:

(a) contacting a test sample with an antibody that binds to a polypeptide of the present invention;

(b) measuring the binding between the test sample and the antibody that binds to the polypeptide of the present invention; and (c) determining that *Campylobacter hyointestinalis* is present if the binding is detected in (b).

The detection methods may use antibodies prepared by the above-described methods. Methods for measuring the binding between a test sample and an antibody that binds to a polypeptide of the present invention include the methods of Western blotting, dot blotting, immunoprecipitation, enzyme-linked immunosorbent assay (ELISA), and immunofluorescence. The presence of *Campylobacter hyointestinalis* in a test sample can be tested by detecting the cytolethal distending toxin of *Campylobacter hyointestinalis* in the test sample using these methods.

Furthermore, the above-described antibodies can be combined with other materials into kits to be used in the detection methods of the present invention. Such kits may comprise distilled water, salts, buffers, protein stabilizers, preservatives, and the like, in addition to the above-described antibodies and detection reagents. Alternatively, to prepare ELISA reagents, the antibodies can be combined with chromogenic substrates for detecting enzyme labels and wash solutions for washing the solid phase. Furthermore, manuals describing the assay procedures can be appended to the kits.

All prior art documents cited herein are incorporated into this specification by reference.

EXAMPLES

Hereinbelow, the present invention is specifically described with reference to the Examples; however, it should not be construed as being limited thereto.

Example 1

Sequencing of the Cdt Genes of the Thai-Derived *C. hyointestinalis* Ch022 Strain The genomic gene was isolated from the Ch022 strain by a conventional method. P 100 ng of the isolated Ch022 genomic gene was subjected to PCR using an Ex Taq PCR kit (TaKaRa) and common primers capable of amplifying the cdtB gene of *C. jejuni, C. coli*, and *C. fetus* (FIG. 1). The concentration of each primer was 0.5 μM. The primers were mixed with 5 μl of 10× Ex Taq buffer, 4 μl of dNTPs, and 1.25 U of Ex Taq. The volume was adjusted to 50 μl with sterile water. The PCR mixture was subjected to PCR with a program consisting of 30 cycles of 94° C. for 30 seconds, 50° C. for 30 seconds, and 72° C. for 30 seconds. The resulting PCR product was electrophoresed on a 2% agarose gel, and it was stained with ethidium bromide. After destaining, the amplification bands were observed under UV light (FIG. 1).

The obtained 720-bp band specifically amplified was purified by a conventional method, and sequenced using the common primers. The sequencing was performed using the BigDye terminator kit ver. 1.1 (Applied Biosystems) according to the manual.

Genome walking primers were designed based on the determined sequence. The full-length gene sequence of 4,069 bp covering the cdt gene (SEQ ID NO: 5) was determined by multiple rounds of upstream and downstream genome walking. Furthermore, ORFs of the cdtA, cdtB, and cdtC gene of the *C. hyointestinalis* Ch022 strain were found to be 798 bp (266 aa; SEQ ID NO: 6), 804 bp (268 aa; SEQ ID NO: 7), and 537 bp (178 aa; SEQ ID NO: 8) in length, respectively. These sequences were compared to the nucleotide sequences of the cdtA, cdtB, and cdtC genes of *C. jejuni, C. coli*, and *C. fetus*. The cdtA and cdtC genes of *C. hyointestinalis* exhibited the highest homology to those of *C. jejuni*, while the cdtB gene of *C. hyointestinalis* showed the highest homology to that of *C. coli* (Table 1). Meanwhile, homology comparison of the deduced amino acid sequences of CdtA, CdtB, and CdtC revealed that the three subunits of *C. hyointestinalis* showed the highest homology to the Cdt subunits of *C. coli*. The homology was 35.7%, 60.5%, and 28.9% for CdtA, CdtB, and CdtC, respectively (Table 1).

TABLE 1

| | Nucleotide (%) | | | Amino acid (%) | | |
|---|---|---|---|---|---|---|
| | cdtA | cdtB | cdtC | CdtA | CdtB | CdtC |
| *C. jejuni* | 51.7 | 63.8 | 52.5 | 35.7 | 60.5 | 28.9 |
| *C. coli* | 51.0 | 64.1 | 42.6 | 40.9 | 61.6 | 29.8 |
| *C. fetus* | 46.1 | 59.7 | 43.0 | 30.2 | 56.2 | 26.2 |

Figure 2:
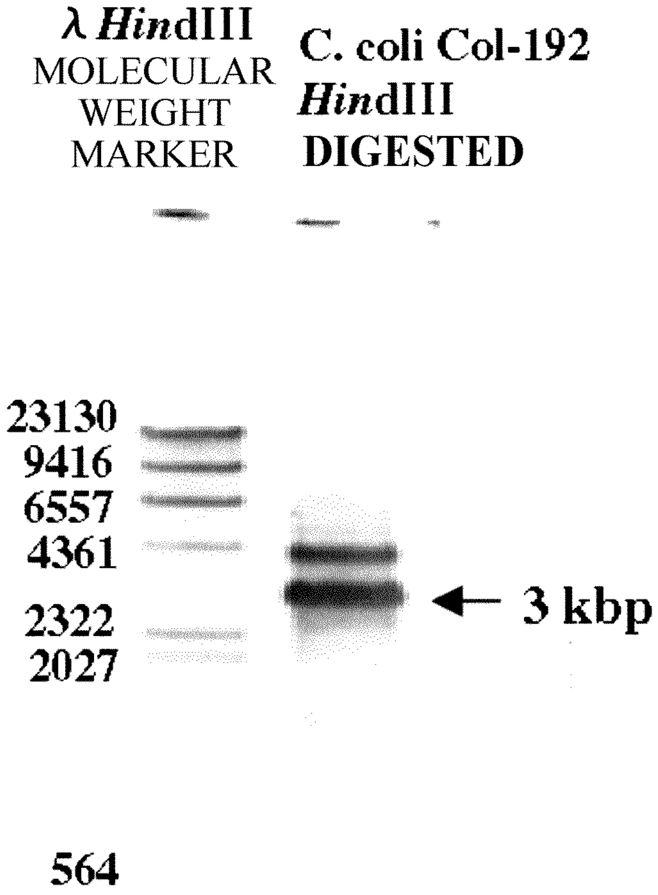
FIG. 2 presents a diagram showing a comparison of deduced CdtB amino acid sequences of *Campylobacter* bacteria. The boxed amino acid residues are thought to be essential for the DNase activity. "C. hyo$^{\#}$" means *C. hyointestinalis.*

The insertion position of the cdt genes of *C. hyointestinalis* was different from that of *C. jejuni, C. coli*, and *C. fetus*. An ORF that has a homology of 53.6% (128 aa/239 aa) to *Helicobacter* glycosyl transferase was found upstream of the cdtA gene. Meanwhile, an ORF that has a homology of 56.0% (155 aa/277 aa) to *T. denitrificans* sugar transferase was found downstream of the cdtC gene. Furthermore, the deduced amino acid sequence of *C. hyointestinalis* CdtB has conserved amino acid residues that are reported to be essential for the DNase activity of CdtB produced by other bacterial species (Yamasaki S, et al., 2006. Toxin Rev, 25, 61-88.) (FIG. 2).

Example 2

Preparation of Recombinant CdtB Protein (Ch-rCdtB) of the Thai-Derived *C. hyointestinalis* Ch022 Strain The cdtB gene of the Thai-derived *C. hyointestinalis* Ch022 strain, in which amino acids 1-17 of CdtB which is predicted to be the CdtB signal sequence was removed, was amplified by PCR and cloned into the pET-28(a) plasmid vector to obtain pWSY-2, a recombinant clone of the cdtB gene of the Thai-derived *C. hyointestinalis* Ch022 strain.

Figure 3:
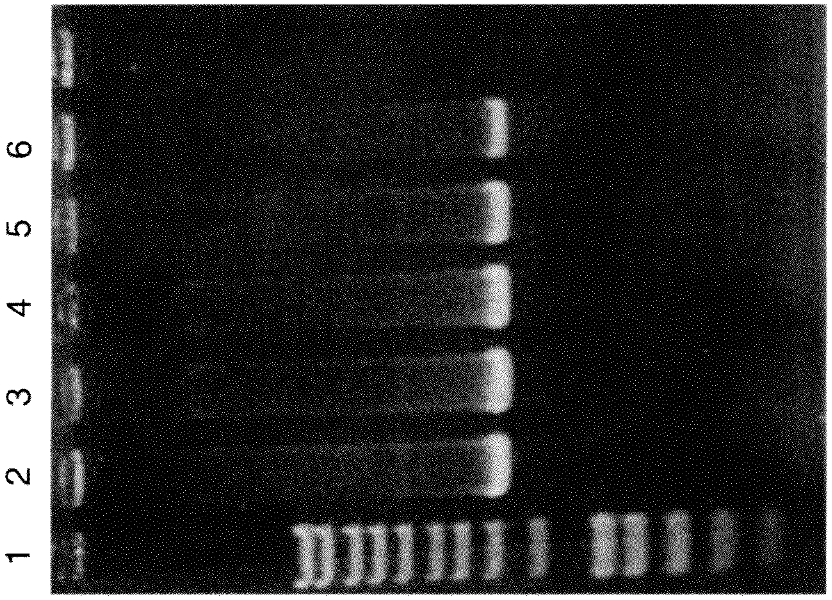
FIG. 3 presents a diagram and a photograph showing preparation of recombinant *C. hyointestinalis* CdtB and an antiserum.

BL-21(DE3) which is an *E. coli* for recombinant protein expression (Novagen) was transformed with pWSY-2. The resulting clone was cultured on a large scale in 600 ml of LB broth containing 20 μg/ml kanamycin, and then expression of the recombinant protein (Ch-rCdtB) was induced with 0.5 mM IPTG at 37° C. for three hours. The Ch-rCdtB-expressing *E. coli* was disintegrated by ultrasonication. The protein was affinity-purified with Ni-Chelating Sepharose (GE Healthcare), and further purified by gel filtration with Superdex 75 (GE Healthcare) (FIG. 3).

Example 3

Figure 4:
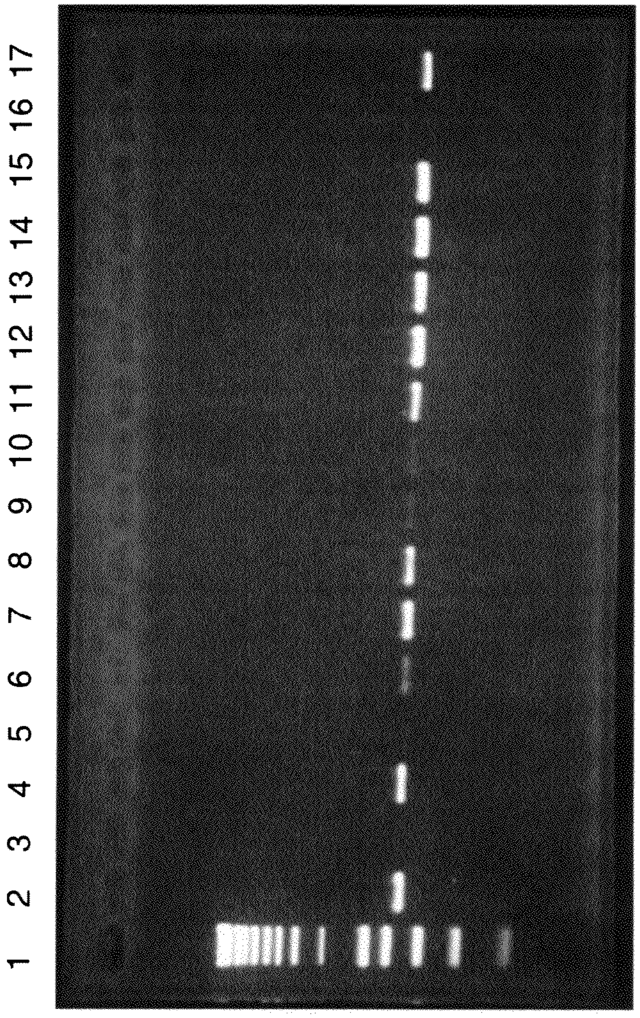
FIG. 4 presents photographs showing the specificity of the anti-HisCdtB antiserum.

Preparation of an Antibody Against CdtB of the Thai-Derived *C. hyointestinalis* Ch022 Strain 250 μg of purified Ch-rCdtB was combined with an equal volume of Freund's complete adjuvant. The resulting emersion was administered subcutaneously and intramuscularly to rabbits (kbs: NZW). Then, starting four weeks after the first administration, the rabbits were immunized five times in total with an emersion containing 250 μg of purified Ch-rCdtB and an equal volume of incomplete Freund's adjuvant at two-week intervals for about eight weeks. An antiserum was thus prepared, and then tested for its titer and specificity by the gel double diffusion method and Western blotting (FIG. 4).

The titer of the anti-Ch-rCdtB antiserum was estimated to be 1:64 by the gel double diffusion method. Meanwhile, there was no precipitate line between the antibody and *C. jejuni* rCdtB. Thus, it was revealed that *C. hyointestinalis* CdtB was immunologically distinct from *C. jejuni* CdtB (FIG. 4C). Western blotting was carried out using purified Ch-rCdtB and a crude toxin solution from the *C. hyointestinalis* Ch022 strain. The antibody reacted specifically with bands corresponding to purified Ch-rCdtB (molecular weight of about 30 kD) and CdtB in the crude toxin solution from the *C. hyointestinalis* Ch022 strain. Thus, it suggests that the specificity of the prepared antibody to Ch-rCdtB was very high (FIG. 4B).

Example 4

Sequencing of the Cdt Genes of *C. hyointestinalis* ATCC 35217

The genomic gene was isolated from the *C. hyointestinalis* ATCC 35217 strain by a conventional method.

Figure 5:
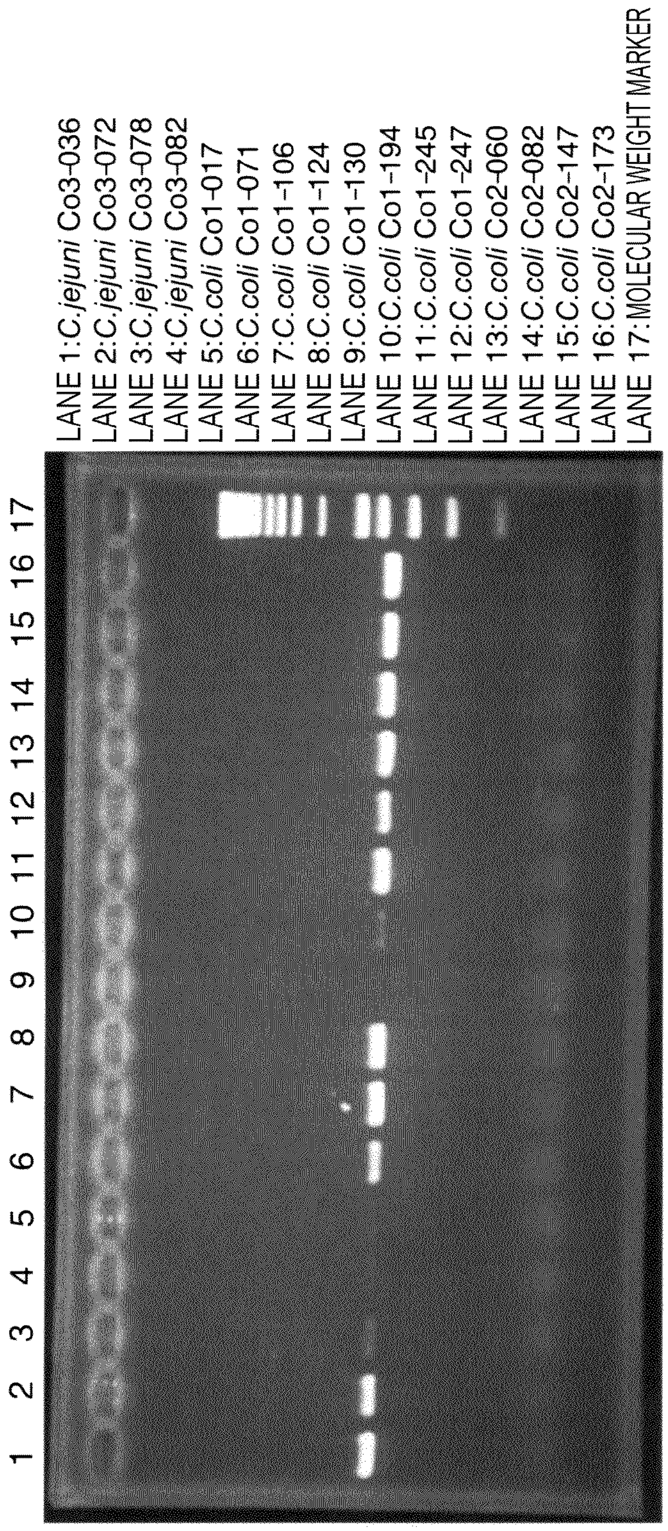
FIG. 5 presents a diagram and a photograph showing amplification of the cdt genes of the *C. hyointestinalis* ATCC strain using degeneration primers.

100 ng of the isolated genomic gene of *C. hyointestinalis* ATCC 35217 was subjected to PCR using the degeneration primers (GNW and WMI) and an Ex Taq PCR kit (TaKaRa) (FIG. 5). The concentration of each primer was 0.5 μM. The primers were mixed with 5 μl of 10× Ex Taq buffer, 4 μl of dNTPs, and 1.25 U of Ex Taq. The volume was adjusted to 50 μl with sterile water. The PCR mixture was subjected to PCR with a program consisting of 30 cycles of 94° C. for 30 seconds, 42° C. for 30 seconds, and 72° C. for 60 seconds. The resulting PCR product was electrophoresed on a 1.5% agarose gel, and it was stained with ethidium bromide. After destaining, the amplification bands were observed under UV light (FIG. 5).

The specifically amplified 960-bp band obtained was purified by a conventional method, and cloned into the pT7Blue plasmid vector (Novagen) to obtain pChATcdtA-B4. The resulting pChATcdtA-B4 plasmid was sequenced using M13 primers, which hybridize with the plasmid. Sequencing was performed using the BigDye terminator kit ver. 1.1 (Applied Biosystems) according to the manual.

The determined sequence was subjected to homology search by BLAST. It was shown that the sequence has homology to portions of the cdtA and cdtB genes.

Genome walking primers were designed based on the determined sequence. The full-length gene sequence of 3,399 bp covering the cdt genes (SEQ ID NO: 1) was determined by multiple rounds of upstream and downstream genome walking. Furthermore, the ORFs of CdtA, CdtB, and CdtC were identified. The amino acid sequences of CdtA, CdtB, and CdtC are shown in SEQ ID NOs: 2, 3, and 4, respectively.

Example 5

CTD Activity Assay Using HeLa Cells (Common to the Thai and ATCC Strains)

Figure 6:
FIG. 6 presents photographs showing the result of assaying the toxic activity of a crude toxin solution from *C. hyointestinalis* towards HeLa cells after 48, 72, and 120 hours.
Figure 7:
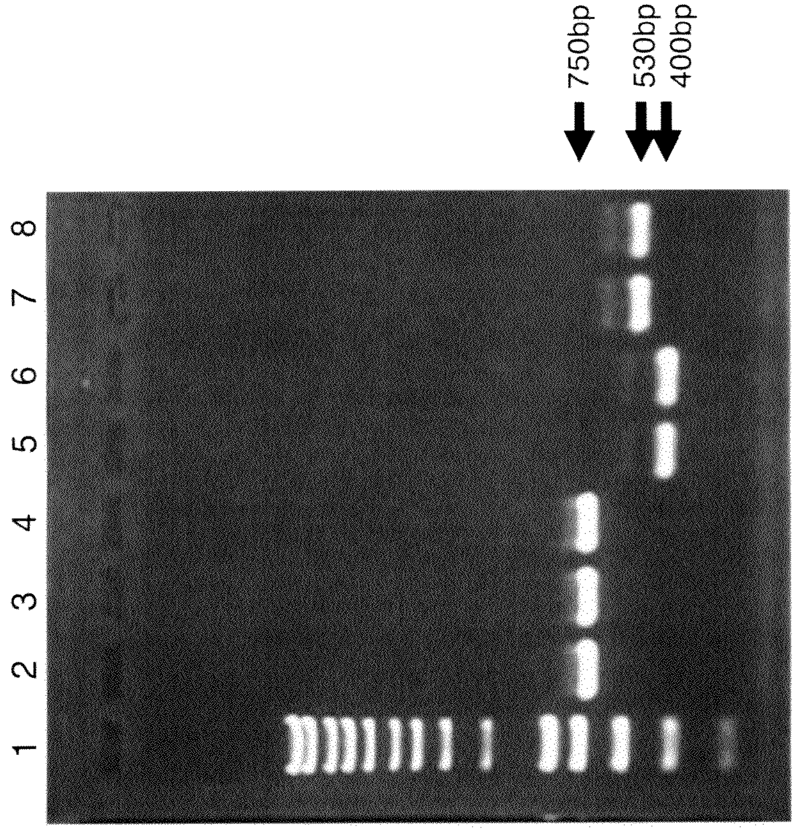
FIG. 7 presents photographs and diagrams showing the result of assaying the toxic activity of a crude toxin solution from *C. hyointestinalis* towards HeLa cells.

The *C. hyointestinalis* Ch022 and ATCC 35217 strains were cultured on horse blood agar media under microaerophilic conditions (5% $CO_2$, 10% $O_2$, and 85% $N_2$) at 37° C. for 48 hours. The resulting bacterial cells were suspended in MEM at an $OD_{600}$ of 1.0, and disintegrated by ultrasonication. After centrifugation, the supernatants were sterilized by filtration using membrane filters (pore size 0.22 μm). The prepared crude toxin solution samples were serially diluted, and added to HeLa cells. Changes in cell morphology were observed after 48 and 120 hours (FIG. 6). For the Thai strain, the specificity of the CDT activity was assessed by simultaneously adding an anti-Ch-rCdtB antiserum to the strain. Furthermore, after 48 hours, the cellular DNA content was quantified using a flow cytometer (FIG. 7). The titer of the toxin was defined as the maximum dilution factor of the crude toxin solution that provides distention of 50% or more cells.

The crude toxin solution from *C. hyointestinalis* was added to HeLa cells, and exhibited cell distending activity after 48 hours and cytolethal activity after 120 hours up to 16× dilution (FIG. 6). These activities were neutralized by the anti-Ch-rCdtB serum. Furthermore, the cellular DNA content was quantified 48 hours after addition of the crude toxin solution using a flow cytometer. The result clearly showed that the cells were arrested in G2/M phase. In the negative control which does not have added crude toxin solution, or when both the crude toxin solution and the anti-Ch-rCdtB serum were added to the cells, a high peak corresponding to G0/G1 but not the G2/M phase arrest was observed (FIG. 7).

The results described above demonstrated that *C. hyointestinalis* produces CDT which has toxin activity. The toxin activity was attributed to the CDT, since it was neutralized by the anti-Ch-rCdtB antiserum.

Example 6

Media, Culture Conditions and Reagents for *Campylobacter* Bacteria

*Campylobacter* bacteria were cultured using horse blood agar media containing CM271 BLOOD AGAR BASE No. 2 (OXOID; Basingstoke, UK) [7.5 g of Proteose Peptone, 1.25 g of liver digest, 2.5 g of yeast extract, 2.5 g of sodium chloride, 6.0 g of agar/500 ml of DW, pH 7.4±0.2 at 25° C.] supplemented with 5% sterile defibrinated horse blood (Nippon Bio-Supp. Center, Tokyo). For *Campylobacter concisus* (hereinafter abbreviated as "*C. concisus*"), 0.25 ml of a solution containing 6% sodium formate and 6% fumaric acid was further applied to each plate. *Campylobacter* bacteria were cultured at 37° C. for two to four days under microaerophilic conditions (10% $CO_2$, 5% $O_2$, and 85% $N_2$) using a LOW TEMPERATURE $O_2$/$CO_2$ INCUBATOR MODEL-9200 (WAKENYAKU, CO., LTD.). *C. concisus* was cultured under the anaerobic conditions of 10% $CO_2$, 10% $H_2$, and 80% $N_2$ for three to seven days.

*E. coli* was cultured at 37° C. for 16 to 20 hours in liquid LB-Lenox medium (5.0 g of Bacto tryptone, 2.5 g of Bacto yeast extract, 2.5 g of NaCl/500 ml of DW; Difco Laboratories, USA) or LB-Lenox agar medium (5.0 g of Bacto tryptone, 2.5 g of Bacto yeast extract, 2.5 g of NaCl, 7.5 g of agar/500 ml of DW; Difco Laboratories).

All other reagents were purchased from Nacalai Tesque, Wako Pure Chemical Industries, or Sigma Chemical Co. (St. Louis, Mo., USA). Restriction enzymes, Takara Ex Taq, and Multiplex PCR assay Kit were purchased from Takara Bio. Seakem GTG agarose, an agarose for electrophoresis, was purchased from Takara Bio. Molecular weight markers were purchased from New England Biolabs (USA).

Example 7

PCR and Preparation of PCR Template DNAs

Colonies were scraped off plates, and added to 200 μl of a TE solution. The suspension was heated for ten minutes. After the heat treatment, the suspension was centrifuged at 12,800×g for ten minutes. The resulting supernatant was collected and used as a template DNA. The *E. coli* C600 strain was used as a negative control.

All PCR experiments were carried out using GeneAmp PCR System 2400 (PerkinElmer) or GeneAmp PCR System 9700 (PerkinElmer). Agarose gel electrophoresis was carried out using a MUPID (ADVANCE) at 100 V in 1× TAE Buffer [40 mM Tris-acetate (pH 8.5), 1 mM EDTA]. After electrophoresis, the gel was stained with 1.0 μg/ml ethidium bromide (Sigma) for 15 minutes. After destaining with DW, the PCR products were analyzed and photographed under ultraviolet light (260 nm) using a gel documentation system, Gel Doc 2000 (Bio-Rad).

Example 8

Figure 8:
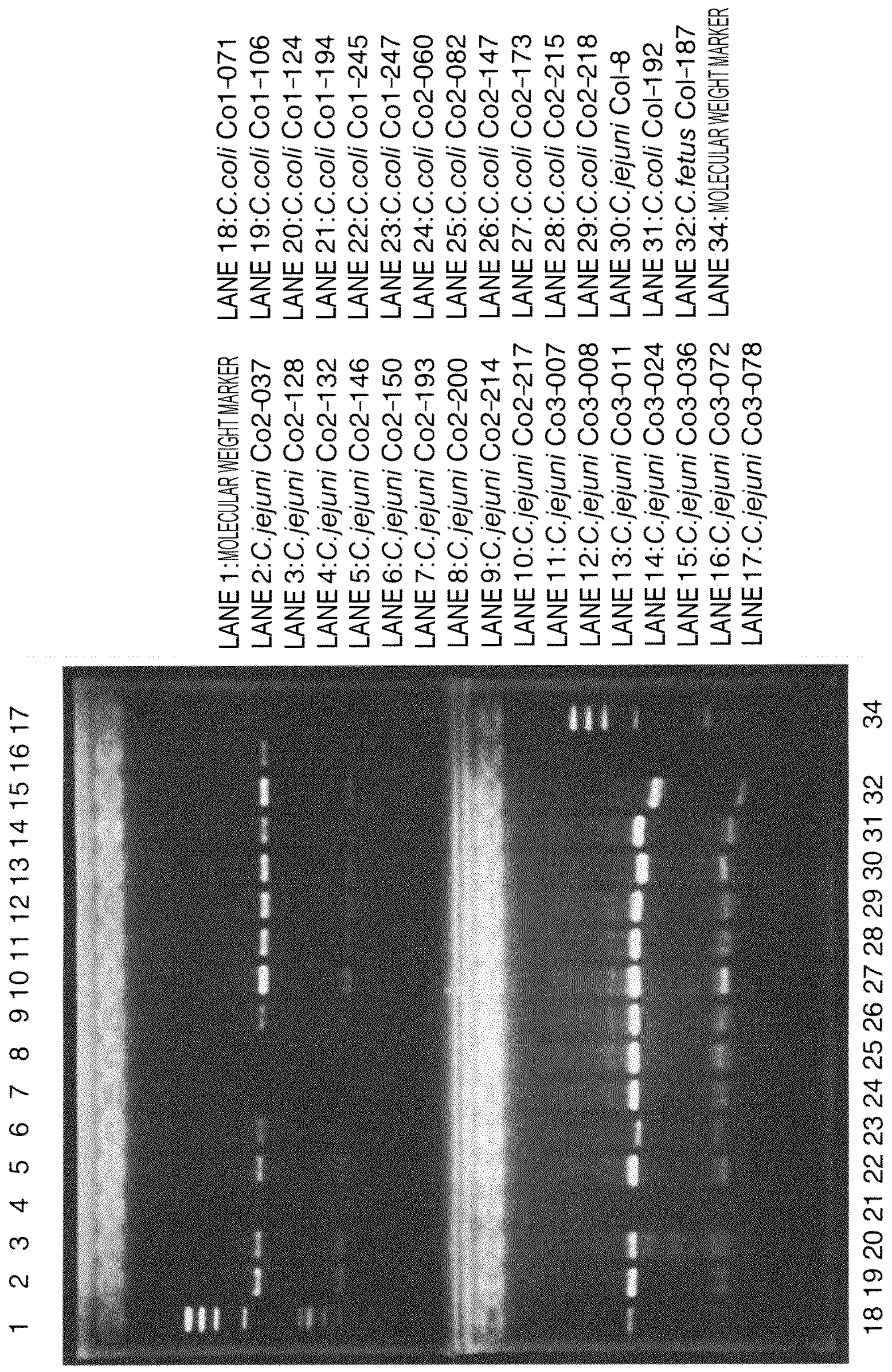
FIG. 8 presents a diagram showing sites of common primers for the cdtB gene of *Campylobacter* bacteria.

PCR for the cdtB Gene of the *C. hyointestinalis* ATCC and Thai-Derived Ch022 Strains Using Common cdtB Gene Primers for *C. jejuni, C. Coli*, and *C. fetus*, or cdtB Gene Primers for the ATCC Strain The cdt genes of *C. hyointestinalis* were sequenced and compared to the cdt gene sequences of other *Campylobacter* bacterial species. The result showed that there were several mutations (marked red) in the binding sites of the common primers for the cdtB gene of *C. jejuni, C. coli*, and *C. fetus* (FIG. 8). When the common primers for the cdtB gene of *C. jejuni, C. coli*, and *C. fetus* were used, PCR yielded a weaker amplified band or no band from the *C. hyointestinalis* ATCC strain as compared to other bacterial species. The 3'-end region homology is particularly important for PCR primers. However, several mutations were found in the 3'-end regions of the primer binding sites in the cdtB gene of the *C. hyointestinalis* ATCC strain (FIG. 8). Mutations in the primer binding sites, in particular the 3'-end region, are thought to be responsible for the inconstant PCR amplification of the cdtB gene of the *C. hyointestinalis* ATCC strain. Thus, common cdtB gene primers were designed for the *C. hyointestinalis* ATCC strain, and compared with the conventional common primers by PCR Bacterial Strains:

*C. hyointestinalis* ATCC35217 strain

*C. hyointestinalis* Ch022 strain

Common Primers:

ComBU: 5'-ACTTGGAATTTGCAAGGC-3'(SEQ ID NO: 14)

ComBR: 5'-TCTAAAATTTACHGGAAAATG-3' (SEQ ID NO: 15)

Primers for the ATCC Strain:

ChATcomBU: 5'-ACTTGGAATATGCAAGGA-3' (SEQ ID NO: 16)

ChATcomBR: 5'-CCAAATGTTATAGGAAAGTG-3' (SEQ ID NO: 17)

PCR:

1 μl of PCR template prepared from each bacterial strain by the boil method was mixed with the primers (final concentration: 1 μM), TaKaRa Ex taq (0.25 U), dNTPs (200 μM each), and 10× Ex Taq Buffer. PCR was carried out at a total volume of 40 μl. The PCR conditions were as follows: 94° C. for three minutes, and 30 cycles of 94° C. for 30 seconds, 50° C. for 30 seconds, and 72° C. for 30 seconds, followed by 72° C. for five minutes.

Figure 9:
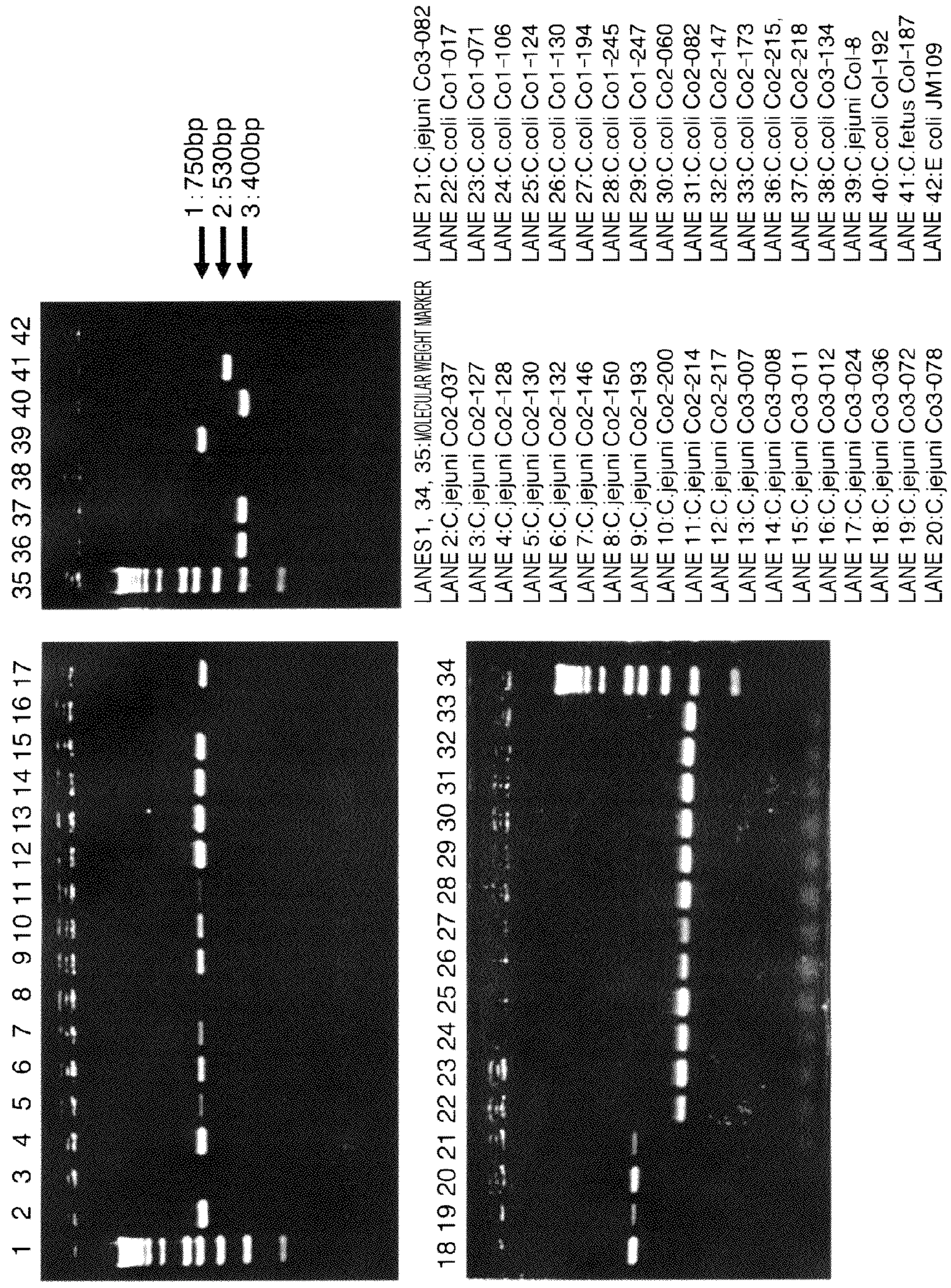
FIG. 9 presents a photograph showing PCR results for the cdtB gene of the *C. hyointestinalis* ATCC and Thai-derived Ch022 strains.

Results:

The common cdtB gene primers for *C. jejuni, C. coli*, and *C. fetus* allowed amplification in the Thai-derived *C. hyointestinalis* Ch022 strain but not the *C. hyointestinalis* ATCC35217 strain. Meanwhile, the primers for the ATCC strain allowed amplification in both the *C. hyointestinalis* Thai-derived Ch022 and ATCC35217 strains (FIG. 9).

Example 9

PCR for Detection of a Broad Range of *Campylobacter* Bacteria Including the *C. hyointestinalis* ATCC and Thai-Derived Ch022 Strains The common cdtB gene primers for *C. jejuni, C. coli*, and *C. fetus* provided only a weakly amplified band in previous experiments, and no detectable band in the experiment described herein for the *C. hyointestinalis* ATCC35217 strain. Thus, PCR was carried out using newly designed common primers for a more stable amplification of the *C. hyointestinalis* cdtB gene.

Primers:

cdtB CommonU: 5'-ACTTGGAATWTGCAAGGM-3' (SEQ ID NO: 18)

cdtB CommonR: 5'-CYAAAWKTTAYHGGAAARTG-3' (SEQ ID NO: 19)

(W: A or T; M: A or C; Y: C or T; K:G or T; H: A, C, or T; R: A or G)

Bacterial Strains:

*C. jejuni* 81-176 strain

*C. coli* Col-243 strain

*C. fetus* Col-187 strain

*C. lari* ATCC43675 strain

*C. upsaliensis* ATCC43954 strain

*C. hyointestinalis* ATCC35217 strain

*C. hyointestinalis* Ch022 strain

*C. helveticus* ATCC51209 strain

*E. coli* C600 strain

PCR:

1 μl of PCR template prepared from each bacterial strain by the boil method was mixed with the primers (final concentration: 1 μM), TaKaRa Ex taq (0.25 U), dNTPs (200 μM each), and 10× Ex Tag Buffer. PCR was carried out at a total volume of 40 μl. The PCR conditions were as follows: 94° C. for three minutes, and 30 cycles of 94° C. for 30 seconds, 50° C. for 30 seconds, and 72° C. for 30 seconds, followed by 72° C. for five minutes.

Figure 10:
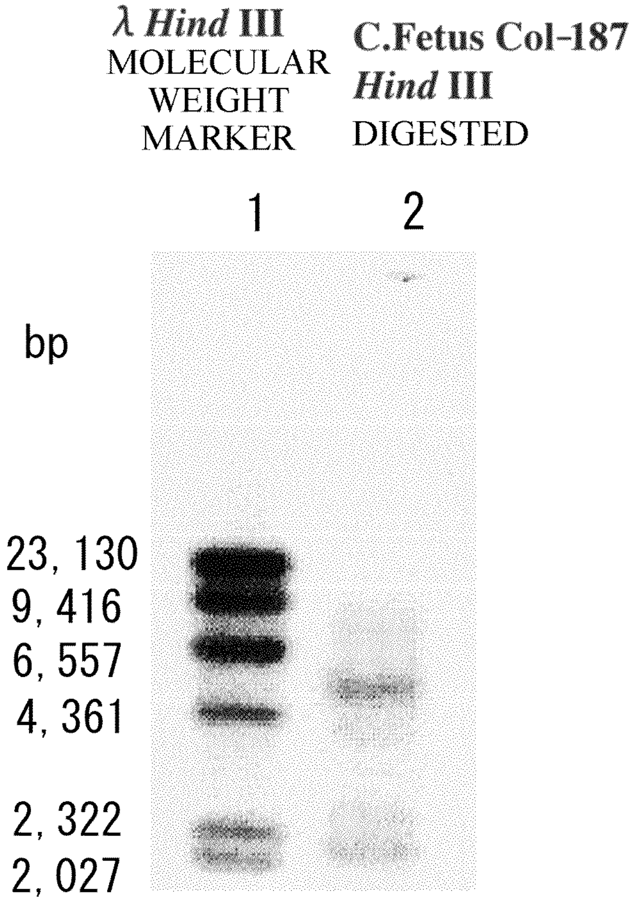
FIG. 10 presents a photograph showing PCR results of using common primers for the cdtB gene.

Results:

Efficient PCR amplification of the bands was observed for all the bacterial strains used (FIG. 10).

Example 10

Estimation of the cdtB Gene Copy Number of the *C. hyointestinalis* ATCC and Thai-Derived Ch022 Strains by Southern Hybridization Both of the conventional common primers and the newly designed primers for the *C. hyointestinalis* ATCC35217 strain allowed amplification in the *C. hyointestinalis* Ch022 strain. This suggested that the *C. hyointestinalis* Ch022 strain has two copies of the cdtB gene. Thus, the cdtB gene copy number of the *C. hyointestinalis* ATCC and Thai-derived Ch022 strains was assessed by Southern hybridization using probes that are specific to each strain.

Bacterial Strains:

*C. jejuni* 81-176 strain

*C. hyointestinalis* ATCC35217 strain

*C. hyointestinalis* Ch022 strain

Primers:

cdtB probes for the *C. hyointestinalis* Ch022 strain

ComBU: 5'-ACTTGGAATTTGCAAGGC-3' (SEQ ID NO: 14)

ComBR: 5'-TCTAAAATTTACHGGAAAATG-3' (SEQ ID NO: 15)

cdtB probes for the *C. hyointestinalis* ATCC strain

ChATcomBU: 5'-ACTTGGAATATGCAAGGA-3' (SEQ ID NO: 22)

ChATcomBR: 5'-CCAAATGTTATAGGAAAGTG-3' (SEQ ID NO: 23)

Probe Preparation:

PCR templates were prepared from the bacterial strains by the boil method. 1 μl of each template was mixed with the primers for the bacterial strain (final concentration: 0.5 μM), TaKaRa Ex taq (0.25 U), digoxigenin-labeled dNTPs (Roche Diagnositics) (200 μM each), and 10× Ex Taq Buffer. PCR was carried out at a total volume of 40 μl. The PCR conditions were as follows: 94° C. for three minutes, and 30 cycles of 94° C. for 30 seconds, 50° C. for 30 seconds, and 72° C. for 30 seconds, followed by 72° C. for five minutes.

The resulting PCR products were electrophoresed on a 1.5% agarose gel, and it was stained with ethidium bromide. After destaining, the detected bands were excised and purified using a Qiagen PCR purification kit (Qiagen), and this was used as a probe.

Preparation and Restriction Enzyme Digestion of Chromosomal Genomic DNA:

The chromosomal genomic DNA was purified using an ISOPLANT Kit (NIPPON GENE). Bacterial cells were scraped off plates, and about 30 mg of the cells were suspended in 150 μl of extraction buffer, and lysed by adding 300 μl of lysis buffer. After 15 minutes of incubation at 50° C., 150 μl of sodium acetate buffer (pH 5.2) was added, and this was allowed to stand on ice for 15 minutes. The aqueous layer was subjected to ethanol precipitation. The precipitate was dissolved in TE [10 mM Tris-HCl (pH 8.0), 1 mM EDTA], and this was used as a DNA solution.

The DNAs were quantified using a spectrophotometer. 1 μg of each genomic DNA was digested with EcoRV or DraI (20 U) at a final volume of 50 μl at 37° C. for five hours.

Southern Hybridization:

The enzyme-digested bacterial genomes were electrophoresed on a 1.5% agarose gel, and then it was stained with ethidium bromide. After destaining, the genomic DNAs were confirmed to be digested with the restriction enzymes. Next, the gel was treated with 0.25 N HCl for 15 minutes. After washing twice with DW, the gel was treated with 0.5 N NaOH for 30 minutes. The DNAs were transferred from the gel onto a nylon membrane using 10×SSC in a Vacuum Blotter for 90 minutes. 2 ml of prehybridization buffer [50% formamide, 5×SSC, 0.01% SDS, 1 mM EDTA, Denhardt's solution, 0.02% BSA, 100 μg/ml heat-denatured herring sperm DNA] was added to each nylon membrane. The membrane was incubated at 42° C. for one hour. Then, the cdtB probes for the *C. hyointestinalis* Ch022 or ATCC strain were heat-denatured and added at 25 ng/ml to the nylon membrane in a hybridization buffer. The nylon membrane was incubated at 42° C. overnight, and then washed twice with 2×SSC containing 0.1% SDS at room temperature for 15 minutes, and twice with 0.1×SSC containing 0.1% SDS at 65° C. for 30 minutes. Then, the nylon membrane was washed for two minutes with washing buffer [0.1 M Tris-HCl (pH 7.5), 0.15 M NaCl, 0.3% Tween 20], and then equilibrated with blocking buffer (Buffer 1 [0.1 M Tris-HCl (pH 7.5), 0.15 M NaCl], 1× Blocking stock solution) at room temperature for 30 minutes. An anti DIG-Alkaline Phosphatase conjugate (7,500 U/ml) was diluted 10,000-fold in fresh blocking buffer, and added to the nylon membrane. After 30 minutes of shaking at room temperature, the membrane was washed twice with Buffer 1 for 15 minutes, and equilibrated with AP9.5 buffer [0.1 M Tris-HCl (pH 9.5), 0.1 M NaCl, 50 mM $MgCl_2$] for five minutes. Finally, the chromogenic substrate solution NBT/BCIP diluted with AP9.5 buffer (4.5 μl of NBT, 3.5 μl of BCIP/1 ml of AP9.5 buffer) was added, and the membrane was incubated in the dark for color development at room temperature for 30 minutes.

Figure 11:
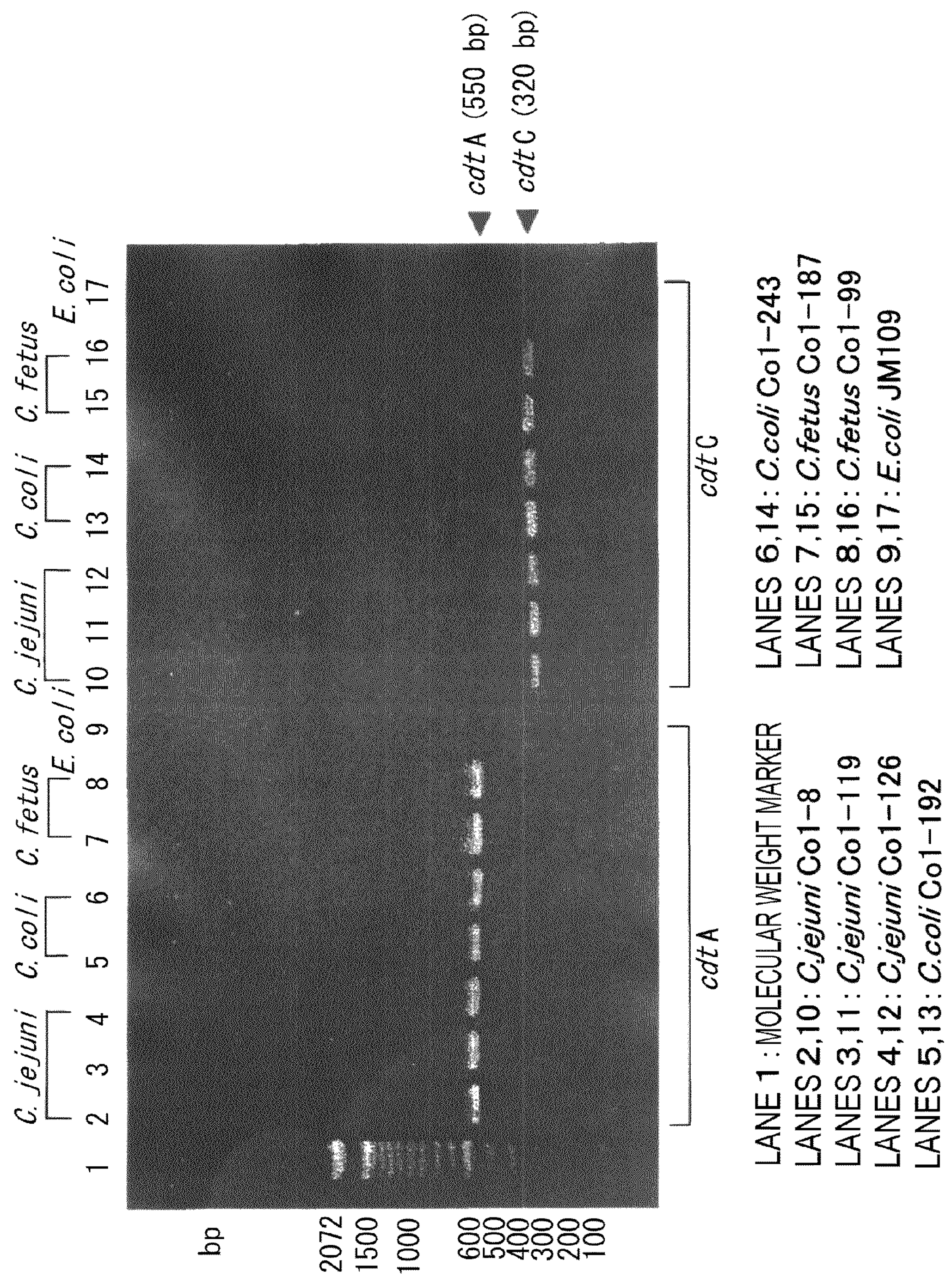
FIG. 11 presents a photograph showing PCR results of using common primers for the cdtB gene.

Results:

The chromosomal genomic DNAs of the *C. hyointestinalis* ATCC and Thai-derived Ch022 strains were digested with EcoRV, and subjected to Southern hybridization using the cdtB probes for the ATCC strain. As a result, the bands at the same position were detected in the two bacterial strains. Furthermore, when the other restriction enzyme (DraI) was used, the bands were also detected at the same position. Thus, it was suggested that the two bacterial strains have an ATCC strain type of cdtB gene homolog (hereinafter, "ATCC type") (FIG. 11). When Southern hybridization was carried out using the cdtB probes for the Thai-derived Ch022 strain, the band was detected only in the Thai-derived *C. hyointestinalis* Ch022 strain. Furthermore, when the DNA was digested with DraI, the position of the band detected with the cdtB probes for the ATCC strain was distinct from that of the band detected with the cdtB probes for the Ch022 strain (FIG. 11). Thus, it was suggested that the Thai-derived *C. hyointestinalis* Ch022 strain has the following two copies of the cdtB gene: an ATCC-type cdtB gene and a cdtB gene homolog of the Thai-derived Ch022 strain (hereinafter referred to as "Thai-type").

Example 11

PCR Using Specific Primers for Detection of the *C. hyointestinalis* ATCC-Type and Thai-Type cdtB Genes The cdtB gene was compared between the *C. hyointestinalis* ATCC and Thai strains. The regions specific to each strain were identified, and specific primers were designed based on the regions. PCR was carried out for several animal-derived *C. hyointestinalis* strains to assess whether they have the ATCC-type and Thai-type cdtB genes.

Primers Specific to the *C. hyointestinalis* Thai-Type cdtB Gene:

Ch022spBUE 5'-TATCAGGCAATAGCGCAG-3' (SEQ ID NO: 20)

Ch022spBR1: 5'-GGTTTGCACCTACATCAAC-3' (SEQ ID NO: 21)

Primers Specific to the *C. hyointestinalis* ATCC-Type cdtB Gene:

ChATspBU2: 5'-CCTAGTAGCGCTACTTAG-3' (SEQ ID NO: 22)

ChATspBR2: 5'-TACAAAGCTTGGGCGAAG-3' (SEQ ID NO: 23)

Bacterial Strains:

*C. hyointestinalis* Ch1-1, Ch87-4, Ch2037, Ch2039, Ch2973, Ch3839, Ch3857, ATCC35217, Ch022

*E. coli* C600

PCR:

1 μl of PCR template prepared from each bacterial strain by the boil method was mixed with the specific primers (final concentration: 0.5 μM), TaKaRa Ex taq (0.25 U), dNTPs (200 μM each), and 10× Ex Tag Buffer. PCR was carried out at a total volume of 40 μl. The PCR conditions were as follows: 94° C. for three minutes, and 30 cycles of 94° C. for 30 seconds, 55° C. for 30 seconds, and 72° C. for 30 seconds, followed by 72° C. for five minutes. The resulting PCR products were electrophoresed on a 2% agarose gel. The gel was stained with ethidium bromide and then destained.

Figure 13:
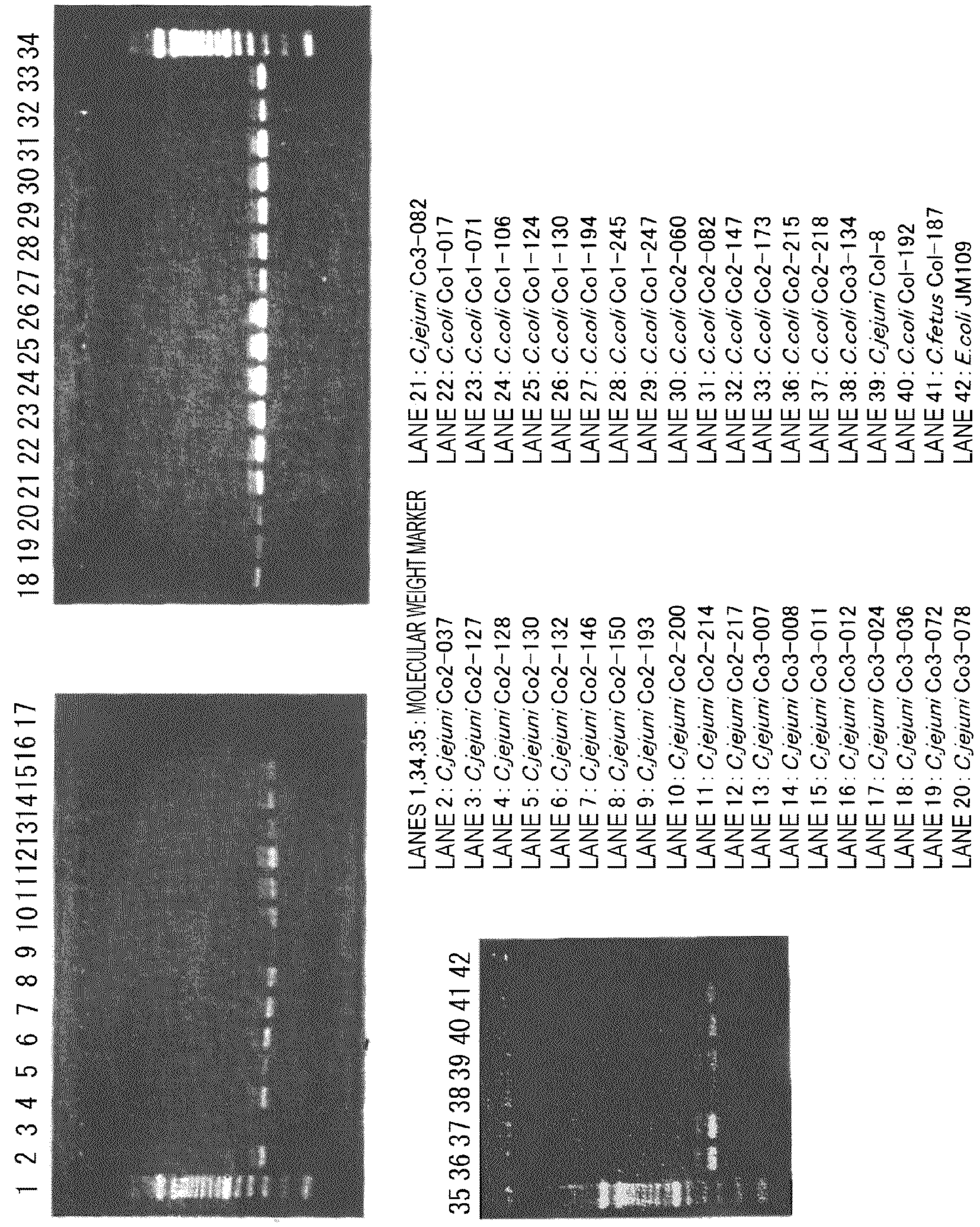
FIG. 13 presents a photograph showing PCR results of using specific primers for detection of the *C. hyointestinalis* ATCC-type cdtB gene.

Results:

It was demonstrated that all of the seven *C. hyointestinalis* strains tested have both the Thai-type (FIG. 12) and ATCC-type (FIG. 13) cdtB genes. The ATCC strain alone did not have the Thai-type cdtB gene.

Example 12

PCR for the *C. hyointestinalis* ATCC-Type and Thai-Type cdtB Genes Using Common Primers The *C. hyointestinalis* ATCC-type and Thai-type cdtB genes were compared to each other. Common regions of the genes were identified, and common primers were designed based on these regions. The size of amplified product was designed to be compatible with the previously reported multiplex PCR which can detect *C. jejuni, C. coli*, and *C. fetus*. PCR was carried out for several animal-derived *C. hyointestinalis* strains to assess the primers.

Common Primers for Detection of the *C. hyointestinalis* ATCC-Type and Thai-Type cdtB Genes:

ChspBU7: 5'-GTTCAAGAAGCAGGAAGC-3'(SEQ ID NO: 24)

ChspBR7: 5'-AATACCWAKAATWGGTCTTG-3'(SEQ ID NO: 25)

(W: A or T; K: G or T)

Bacterial Strains:

*C. hyointestinalis* Ch1-1, Ch87-4, Ch2037, Ch2039, Ch2973, Ch3839, Ch3857, ATCC35217, Ch022

*E. coli* C600

PCR:

1 μl of PCR template prepared from each bacterial strain by the boil method was mixed with the specific primers (final concentration: 0.5 μM), TaKaRa Ex taq (0.25 U), dNTPs (200 μM each), and 10× Ex Tag Buffer. PCR was carried out at a total volume of 40 μl. The PCR conditions were as follows: 94° C. for three minutes, and 30 cycles of 94° C. for 30 seconds, 55° C. for 30 seconds, and 72° C. for 30 seconds, followed by 72° C. for five minutes. The resulting PCR products were electrophoresed on a 2% agarose gel. The gel was stained with ethidium bromide and then destained.

Figure 14:
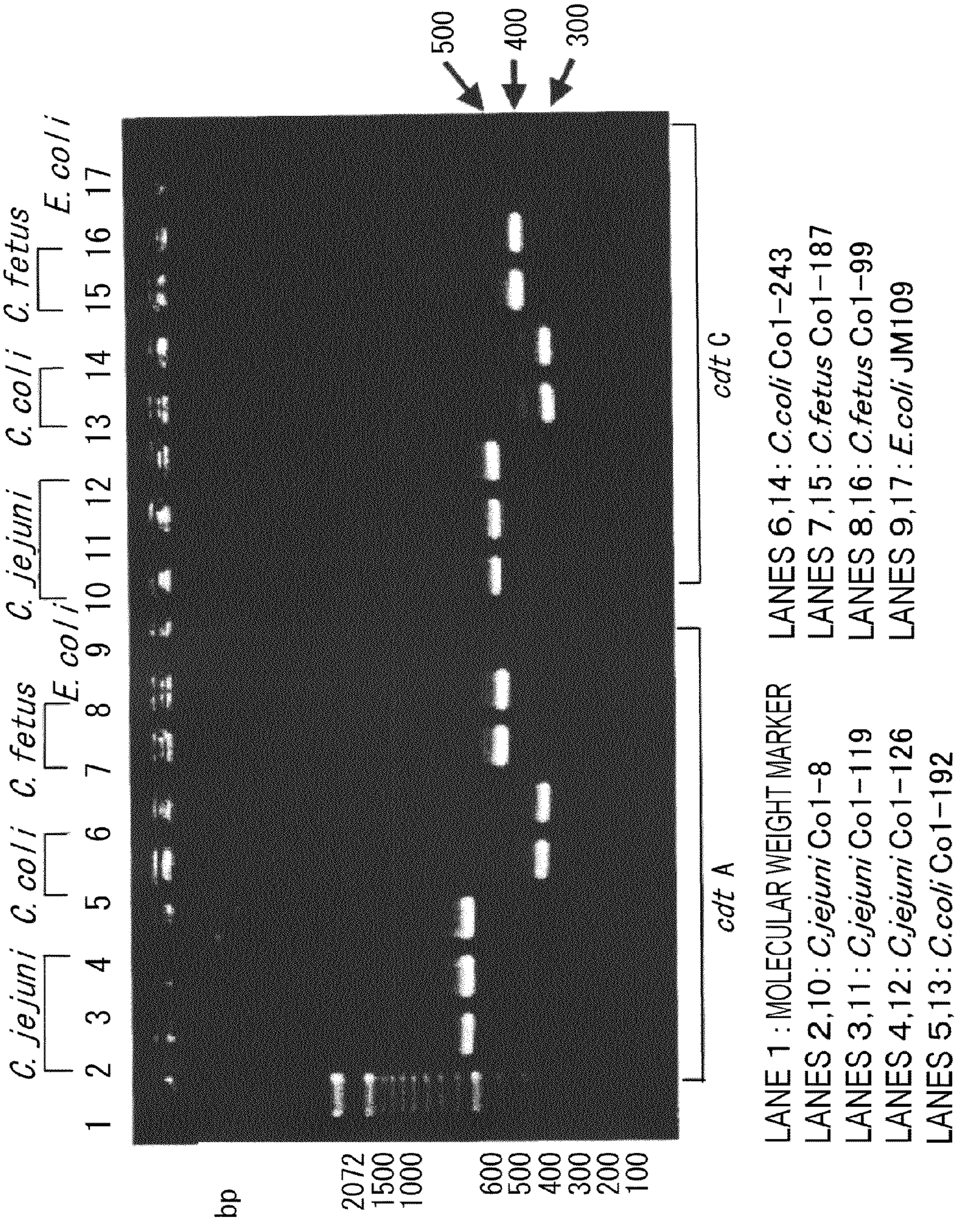
FIG. 14 presents a photograph showing PCR results of using common primers for detection of the *C. hyointestinalis* ATCC-type and Thai-type cdtB genes.

Results:

The *C. hyointestinalis* cdtB gene was successfully amplified for all of the seven *C. hyointestinalis* strains tested (FIG. 14).

Example 13

Development of CdtB Gene-Based Multiplex PCR for Detecting *C. jejuni, C. Coli, C. Fetus*, and *C. hyointestinalis*

Since primers that can efficiently amplify both the *C. hyointestinalis* ATCC-type and Thai-type cdtB genes were already developed, the primers were integrated into conventional multiplex PCR to develop multiplex PCR that can detect a broader range of *Campylobacter* bacteria.

Bacterial Strains:

*C. jejuni* 81-176 strain
*C. coli* Col-243 strain
*C. fetus* Col-187 strain
*C. lari* ATCC43675 strain
*C. upsaliensis* ATCC43954 strain
*C. hyointestinalis* Ch022 strain
*C. helveticus* ATCC51209 strain
*C. concisus* ATCC33237 strain
*E. coli* C600 strain Primers:

Cj-CdtBU5: 5'-ATCTTTTAACCTTGCTTTTGC-3' (final concentration: 0.25 μM) (SEQ ID NO: 26)

Cj-CdtBR6: 5'-GCAAGCATTAAAATCGCAGC-3' (final concentration: 0.25 μM) (SEQ ID NO: 27)

Cc-CdtBU5: 5'-TTTAATGTATTATTTGCCGC-3' (final concentration: 0.5 μM) (SEQ ID NO: 28)

Cc-CdtBR5: 5'-TCATTGCCTATGCGTATG-3' (final concentration: 0.5 μM) (SEQ ID NO: 29)

Cf-CdtBU6: 5'-GGCTTTGCAAAACCAGAAG-3' (final concentration: 0.5 μM) (SEQ ID NO: 30)

Cf-CdtBR3: 5'-CAAGAGTTCCTCTTAAACTC-3' (final concentration: 0.5 μM) (SEQ ID NO: 31)

ChspBU7: 5'-GTTCAAGAAGCAGGAAGC-3' (final concentration: 0.5 μM) (SEQ ID NO: 24)

ChspBR7: 5'-AATACCWAKAATWGGTCTTG-3' (final concentration: 0.5 μM) (SEQ ID NO: 25)

(W: A or T; K: G or T)

PCR:

1 μl of PCR template prepared from each bacterial strain by the boil method was mixed with the specific primers, 0.2 μl of Multiplex PCR Mix 1 (Takara Bio), and 20 μl of 2× Multiplex PCR Mix 2 (Takara Bio). PCR was carried out at a total volume of 40 μl. The PCR conditions were as follows: 94° C. for one minute, and 30 cycles of 94° C. for 30 seconds, 56° C. for 90 seconds, and 72° C. for 90 seconds, followed by 72° C. for five minutes. The resulting PCR products were electrophoresed on a 2% agarose gel. The gel was stained with ethidium bromide and then destained.

Results:

The multiplex PCR that targets the four bacterial species was able to efficiently detect the cdtB gene when any one of *C. jejuni, C. coli, C. fetus*, and *C. hyointestinalis* was present. Moreover, bacterial species-specific amplification of the gene was observed even in the presence of multiple bacterial species (FIG. 15).

Example 14

Novel Multiplex PCR that Targets Almost all Pathogenic *Campylobacter* Bacteria Of *Campylobacter* bacteria, *C. jejuni, C. coli, C. fetus*, and *C. hyointestinalis* have catalase activity and grow at 42° C. These bacterial species are called "thermophilic *Campylobacters*", and most of the bacterial species that are responsible for food poisoning belong to this group. The present inventors developed multiplex PCR that can simultaneously detect the six *Campylobacter* bacterial species including *C. fetus* which is pathogenic for human and animals such as domestic animals, in addition to the five bacterial species belonging to the thermophilic *Campylobacters.*

Bacterial Strains:

*C. jejuni* 81-176 strain
*C. coli* Col-243 strain
*C. fetus* Col-187 strain
*C. lari* ATCC43675 strain
*C. upsaliensis* ATCC43954 strain
*C. hyointestinalis* Ch022 strain Primers:

Cj-CdtBU5: 5'-ATCTTTTAACCTTGCTTTTGC-3' (final concentration: 0.25 μM) (SEQ ID NO: 26)

Cj-CdtBR6: 5'-GCAAGCATTAAAATCGCAGC-3' (final concentration: 0.25 μM) (SEQ ID NO: 27)

Cc-CdtBU5: 5'-TTTAATGTATTATTTGCCGC-3' (final concentration: 0.375 μM) (SEQ ID NO: 28)

Cc-CdtBR5: 5'-TCATTGCCTATGCGTATG-3' (final concentration: 0.375 μM) (SEQ ID NO: 29)

Cf-CdtBU6: 5'-GGCTTTGCAAAACCAGAAG-3' (final concentration: 0.375 μM) (SEQ ID NO: 30)

Cf-CdtBR3: 5'-CAAGAGTTCCTCTTAAACTC-3' (final concentration: 0.375 μM) (SEQ ID NO: 31)

ChspBU7: 5'-GTTCAAGAAGCAGGAAGC-3' (final concentration: 0.375 μM) (SEQ ID NO: 24)

ChspBR7: 5'-AATACCWAKAATWGGTCTTG-3' (final concentration: 0.375 μM) (SEQ ID NO: 25)

CupspBU3: 5'-CATAGTTAGTCGCGTCCA-3' (final concentration: 0.375 μM) (SEQ ID NO: 32)

CupspBR4: 5'-CCAGTTAATCTCAGGACG-3' (final concentration: 0.375 μM) (SEQ ID NO: 33)

ClaspBU4: 5'-GTATCCATGCTTTATCAAGA-3' (final concentration: 0.375 μM) (SEQ ID NO: 34)

ClaspBR4: 5'-GTAGGCCTATAAGAGAACC-3' (final concentration: 0.375 μM) (SEQ ID NO: 35)

(W: A or T; K: G or T)

PCR:

0.5 μl of PCR template prepared from each bacterial strain by the boil method was mixed at the indicated final concentration with 0.2 μl of Multiplex PCR Mix 1 (Takara Bio), and 20 μl of 2× Multiplex PCR Mix 2 (Takara Bio). PCR was carried out at a total volume of 40 μl. The PCR conditions were as follows: 94° C. for one minute, and 30 cycles of 94° C. for 30 seconds, 56° C. for 90 seconds, and 72° C. for 90 seconds, followed by 72° C. for five minutes. The resulting PCR products were electrophoresed on a 2% agarose gel. The gel was stained with ethidium bromide and then destained.

Results:

The multiplex PCR that targets the six bacterial species was able to efficiently detect the cdtB gene when any one of the *Campylobacter* species was present. Moreover, bacterial species-specific amplification of the gene was observed even in the presence of all six bacterial species (FIG. 16).

INDUSTRIAL APPLICABILITY

The present invention provides cdt genes which are useful for detection of *C. hyointestinalis*. Toxin production by the cdt genes was demonstrated.

As described above, *C. hyointestinalis* is an important bacterium from the viewpoint of public hygiene since it causes food poisoning. However, it was difficult to detect *C. hyointestinalis*, since the conventional culture and test methods target only *C. jejuni* and *C. coli*. Furthermore, it was difficult to identify the *C. hyointestinalis* cdt genes of the present invention by using known gene probes for bacteria belonging to the same genus, since homology of the *C. hyointestinalis* cdt genes to the *C. jejuni, C. coli*, and *C. fetus* cdt genes is not very high (approximately 60%).

The present invention enables rapid and accurate determination of bacteria that cause food poisoning or the like, since specific detection of *C. hyointestinalis* is possible. The methods of the present invention are very useful not only clinically but also in the process management of food production or such, factory hygiene management, etc.

The present invention also provides methods for detection of the six *Campylobacter* bacterial species including *C. hyointestinalis*. The *Campylobacter* bacteria targeted by the detection methods of the present invention excluding *C. fetus* are bacterial species that can grow at 42° C. under microaerophilic conditions, and thus are called "thermophilic *Campylobacters*". Almost all *Campylobacter* bacteria that are responsible for food poisoning are considered to belong to the thermophilic *Campylobacters*. The present invention enables simple and rapid identification of food poisoning bacteria.

The invention claimed is:

1. A method for detecting a *Campylobacter* bacterium in a test sample using a quantitative PCR method or quantitative real-time PCR method, which comprises the step of nucleic acid amplification reaction in a test sample using one or more of:

(a) a primer pair comprising the sequences of SEQ ID NOs: 37 and 38 which is capable of amplifying a genomic DNA region of cdtC of *Campylobacter jejuni* and a probe comprising SEQ ID NO: 39 for detecting amplified nucleic acid fragments;

(b) a primer pair comprising the sequences of SEQ ID NOs: 40 and 41 which is capable of amplifying a genomic DNA region of cdtC of *Campylobacter coli* and a probe comprising SEQ ID NO: 42 for detecting amplified nucleic acid fragments; and (c) a primer pair comprising the sequences of SEQ ID NOs: 43 and 44 which is capable of amplifying a genomic DNA region of cdtC of *Campylobacter fetus* and a probe comprising SEQ ID NO: 45 for detecting amplified nucleic acid fragments.

2. The method of claim 1, comprising simultaneously amplifying nucleic acids using the primer pairs and probes of (a) to (c) in the same reaction.

3. A kit for use in the method of claim 1, which comprises a manual and at least one of:

(a) a primer pair comprising the sequences of SEQ ID NOs: 37 and 38 which is capable of amplifying a genomic DNA region of cdt of *Campylobacter jejuni* and a labeled probe comprising SEQ ID NO: 39 for detecting amplified nucleic acid fragments;

(b) a primer pair comprising the sequences of SEQ ID NOs: 40 and 41 which is capable of amplifying a genomic DNA region of cdt of *Campylobacter coli* and a labeled probe comprising SEQ ID NO: 42 for detecting amplified nucleic acid fragments; and (c) a primer pair comprising the sequences of SEQ ID NOs: 43 and 44 which is capable of amplifying a genomic DNA region of cdt of *Campylobacter fetus* and a labeled probe comprising SEQ ID NO: 45 for detecting amplified nucleic acid fragments.

4. The kit of claim 3, comprising the primer pairs and probes of (a) to (c).

* * * * *

SEQUENCE LISTING

```
<160> NUMBER OF SEQ ID NOS: 61

<210> SEQ ID NO 1
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 1

atcttttaac cttgcttttg c                                              21


<210> SEQ ID NO 2
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 2

gcaagcatta aaatcgcagc                                                20


<210> SEQ ID NO 3
<211> LENGTH: 19
<212> TYPE: DNA
<213> ORGANISM: Artificial
<220> FEATURE:
<223> OTHER INFORMATION: An artificially synthesized primer sequence

<400> SEQUENCE: 3

ggctttgcaa aaccagaag                                                 19


<210> SEQ ID NO 4
<211> LENGTH: 20
<212> TYPE: DNA
<213> ORGANISM: Artificial
<220> FEATURE:
```

-continued

<223> OTHER INFORMATION: An artificially synthesized primer sequence

<400> SEQUENCE: 4
caagagttcc tcttaaactc 20

<210> SEQ ID NO 5
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 5
tttaatgtat tatttgccgc 20

<210> SEQ ID NO 6
<211> LENGTH: 18
<212> TYPE: DNA
<213> ORGANISM: Artificial
<220> FEATURE:
<223> OTHER INFORMATION: An artificially synthesized primer sequence

<400> SEQUENCE: 6
tcattgccta tgcgtatg 18

<210> SEQ ID NO 7
<211> LENGTH: 18
<212> TYPE: DNA
<213> ORGANISM: Artificial
<220> FEATURE:
<223> OTHER INFORMATION: An artificially synthesized primer sequence

<400> SEQUENCE: 7
acttggaatt tgcaaggc 18

<210> SEQ ID NO 8
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 8
tctaaaattt achggaaaat g 21

<210> SEQ ID NO 9
<211> LENGTH: 20
<212> TYPE: DNA
<213> ORGANISM: Artificial
<220> FEATURE:
<223> OTHER INFORMATION: An artificially synthesized primer sequence
<220> FEATURE:
<221> NAME/KEY: misc_feature
<222> LOCATION: (6)..(6)
<223> OTHER INFORMATION: "n" = c or t

<400> SEQUENCE: 9
gataangatc ctttaaaact 20

<210> SEQ ID NO 10
<211> LENGTH: 21
<212> TYPE: DNA
<213> ORGANISM: Artificial
<220> FEATURE:
<223> OTHER INFORMATION: An artificially synthesized primer sequence
<220> FEATURE:
<221> NAME/KEY: misc_feature -continued
<222> LOCATION: (1)..(1)
<223> OTHER INFORMATION: "n" = a or t
<220> FEATURE:
<221> NAME/KEY: misc_feature
<222> LOCATION: (2)..(2)
<223> OTHER INFORMATION: "n" = a or t
<220> FEATURE:
<221> NAME/KEY: misc_feature
<222> LOCATION: (11)..(11)
<223> OTHER INFORMATION: "n" = a or t
<220> FEATURE:
<221> NAME/KEY: misc_feature
<222> LOCATION: (16)..(16)
<223> OTHER INFORMATION: "n" = c or g

<400> SEQUENCE: 10
nnccaaagcg nttttntatg g 21

<210> SEQ ID NO 11
<211> LENGTH: 18
<212> TYPE: DNA
<213> ORGANISM: Artificial
<220> FEATURE:
<223> OTHER INFORMATION: An artificially synthesized primer sequence

<400> SEQUENCE: 11
ccacagaaag caaatgga 18

<210> SEQ ID NO 12
<211> LENGTH: 26
<212> TYPE: DNA
<213> ORGANISM: Artificial
<220> FEATURE:
<223> OTHER INFORMATION: An artificially synthesized primer sequence

<400> SEQUENCE: 12
ctaatcgtgt aaatttagct atagtt 26

<210> SEQ ID NO 13
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 13
tttttcaata tccatgcttt agc 23

<210> SEQ ID NO 14
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 14
tggatgatag caggggattt taa 23

<210> SEQ ID NO 15
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 15
rahgatmmdg atmgatccwy caaa 24

-continued

<210> SEQ ID NO 16
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 16
rwaayaggyg yttgyawrca 20

<210> SEQ ID NO 17
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 17
vakyywrwwk aycaaaaytg g 21

<210> SEQ ID NO 18
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 18
vctadwccwa mkckwtytts 20

<210> SEQ ID NO 19
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 19
attgccaagg ctaaaatctc 20

<210> SEQ ID NO 20
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 20
gataaagtct ccaaaactgc 20

<210> SEQ ID NO 21
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 21
aggacttgaa cctacttttc 20

<210> SEQ ID NO 22
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 22
aggtggagta gttaaaaacc 20

<210> SEQ ID NO 23
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 23
aacgacaaat gtaagcactc 20

<210> SEQ ID NO 24
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 24
tatttatgca agtcgtgcga 20

<210> SEQ ID NO 25
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 25
tagggatatg cacgcaaaag 20

<210> SEQ ID NO 26
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 26
gcttaataca gttacgatag 20

<210> SEQ ID NO 27
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 27
tttagccttt gcaactccta 20

<210> SEQ ID NO 28
<211> LENGTH: 19
<212> TYPE: DNA
<213> ORGANISM: Artificial
<220> FEATURE:
<223> OTHER INFORMATION: An artificially synthesized primer sequence

<400> SEQUENCE: 28
aaggggtagc agctgttaa 19

<210> SEQ ID NO 29

<211> LENGTH: 20
<212> TYPE: DNA
<213> ORGANISM: Artificial
<220> FEATURE:
<223> OTHER INFORMATION: An artificially synthesized primer sequence

<400> SEQUENCE: 29
aagcataagt tttgcaaacg 20

<210> SEQ ID NO 30
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 30
gtttggattt tcaaatgttc c 21

<210> SEQ ID NO 31
<211> LENGTH: 2600
<212> TYPE: DNA
<213> ORGANISM: Campylobacter jejuni

<400> SEQUENCE: 31
tgctaaaata taagtgttta agatacatat aaattctacc tttaaaaaca acaaaataaa 60
acatttttaa aaagcggaaa attataatga aatttatgtt attattttct taaaaattta 120
aatacatatc aaggttttta atgcaaaaaa ttatagtttt tattttatgt tgttttatga 180 cttttttct ttatgcatgt tcttctaaat ttgaaaatgt aaatcctttg gggcgttcat 240
ttggagaatt tgaagatact gatcctttaa aactaggact tgaacctact tttcctacca 300
atcaagaaat tccaagttta attagcggtg ctgatttagt acctattact cctattaccc 360
cacctttaac tagaacaagc aatagtgcca acaataatgc agcaaatggg atcaatcctc 420
gctttaaaga cgaagctttt aatgatgttt taatttttga aaatcgccct gcggtttctg 480
attttttaac cattttaggc cctagcggag cagctttaac ggtttgggct ttagcacaag 540
gaaattggat ttggggctat actttaatcg atagcaaagg atttggcgat gctagagttt 600
ggcaactttt gctttatcct aatgattttg caatgattaa aaatgccaaa accaatactt 660
gtcttaatgc ttatggtaat ggaattgtcc attatccttg tgatgcaagc aatcacgcac 720
aaatgtggaa acttatccct atgagcaata cagcggttca aattaaaaat ttaggaaatg 780
gaaaatgcat acaagcacct attacaaatc tttatggtga ttttcacaag gtttttaaaa 840
tttttaccgt agagtgtgca aaaaaagata attttgatca acaatggttt ttaactactc 900
caccttttac cgcaaaacct ttatatcgcc aaggagaggt acgatgaaaa aaattatatg 960
tttattttta tcttttaacc ttgcttttgc aaatttagaa aattttaatg ttggcacttg 1020
gaatttgcaa ggctcatccg cagccacaga aagcaaatgg agtgttagtg taagacaact 1080
tgtaagtgga gcaaacccct tagatatctt aatgatacaa gaagcaggaa ctttaccaag 1140
aacagccact ccaacaggac gccatgtgca acaaggtgga acacctattg atgaatatga 1200
gtggaattta ggaactcttt caaggcctga tagggttttt atttattatt ctcgcgttga 1260
tgtaggagct aatcgtgtaa atttagctat agtttcaaga atgcaagctg aagaagtgat 1320
tgttttacct ccacctacta cagtttcaag acccattata ggaattcgca atggaaatga 1380 tgctttttc aatatccatg ctttagctaa tggaggaaca gatgtaggag caattatcac 1440
agctgtagat gcacattttg caaatatgcc tcaagttaac tggatgatag caggggattt 1500
taaccgtgat ccttctacta taacaagtac agtggataga gaattagcaa atagaattag 1560
agtggttttt ccaactagcg caactcaagc aagcggaggg actcttgatt atgcaattac 1620
aggaaattca aatagacaac aaacctatac tccaccgctt ttagctgcga ttttaatgct 1680
tgcaagttta agatctcata tagtttcaga tcattttcca gtaaatttta gaaaatttta 1740
ggacatttaa tatgaaaaaa attattactt tgttttttat gtttataact ttagcctttg 1800
caactcctac tggagatttg aaagatttta ccgaaatggt ttctataaga agcttagaaa 1860
cgggaatttt tttaagcgcc tttagggata cctcaaaaga tcctattgat caaaattgga 1920
atattaaaga aattgtttta agcgatgagt taaaacaaaa agataaatta gctgatgaac 1980
ttccttttgg ttatgtgcaa tttacaaatc caaaagaaag cgatctttgt ttagccatct 2040
tagaagatgg aacctttgga gcaaaatctt gtcaagatga tctaaaagat ggtaaattag 2100
aaactgtatt ttctataatg ccaacaacaa cttcagctgt gcaaattcgt tctttagttt 2160
tggaatctga tgaatgtata gtaacttttt ttaatccaaa tattcctata caaaaacgct 2220
ttggaatagc cccttgcacc ctagatccta ttttttttgc tgaagtaaat gaactaatga 2280
ttataacccc acctttaaca gctgctaccc ctttagaata agatttttat cttgttctat 2340
ttttatattt atttaatatt tatgatatta ctaaaataca caaaataatt aataataata 2400
caatgtaatt taccttgctc tataattttt ttattttaat gtaatttttt gttacaataa 2460
atttatacat aataattatc ttggaggaaa aattggaaca aattttaaca tggcaacaaa 2520
tttatgaccc tttttcaaat atttggctaa gtgctttagt ggcattttta cctatactat 2580 gtttttagt ttgtttggtt 2600

<210> SEQ ID NO 32
<211> LENGTH: 4090
<212> TYPE: DNA
<213> ORGANISM: Campylobacter fetus

<400> SEQUENCE: 32
aagcttgagc gcccatgtgt attttgcttt tgtgaagttt agaattccat gcggatttcc 60
accaaatact tttctatcgt ttaaagtctc gttcgagctt ggattataaa ttttttttct 120
attcataata aatctttcaa attttaaagt agcattagca ttttatccaa aaaagtatta 180
aataactttg aatacaaatt tatgaaacta aaataataat gcatgctttt taataattat 240
tgataatata ttaattacat tggtattaga attcaaatta aaaaaaggat taccgatgaa 300
aaaagcattt acgatggtag aattagcatt tgttatagtt attaccggct tattagcaag 360
tgttagtata ccaaaactta caatgtcaag aacggatgcc gaagtggcaa aaatagtagt 420
cgatataaaa aatacatttg ataaaataaa ctctatctat atatcaaata gctcagtcaa 480
taaaaaatta aatgccgata aaaacgaagt tgatagttat ctccatttaa gattattaat 540
aggaaatgac tcgacattat ctgattttga ggcgattaaa cgcggtgcta aagagcaccc 600
ttgggcagtt gaatgcttat tttatagtat tgataatagc acgataaagt ttaaaaccat 660
gtggcagcaa tcatctatct catggaaaaa gacctgcaac gctctttatc ttcaccctac 720
aatgaaagag tggatacaaa acggaattca attaggcgga gatagcatct taaaaaacag 780
ttaaatttat aattggataa tttttatata actgaaatat ataataaata tcggaaaatc 840
aaatttaaat acgaaaagta acgatctgaa taaatcatcc ttgaattata aatattttta 900
ttatgaatat aaatttttca aatttcacaa caacttaaat tttatacaaa taaattttaa 960

-continued

```
tatattatat gacgaaattt tcgactatga agttataatt ttggtatgta tttaaaattt   1020
atttattttt atttattaaa ttttacaaat atcattatag gtaaatttta tgaaaaaact   1080
tttgcggcta ttaaatctac tcagccaaaa tgatatttta aaaattacca aaatcaaaaa   1140
atactaaaaa aggaaattta tgactaaaat tattttcaag catattaaaa atagtcttat   1200
tttactattt tgtatcgctc tttttagtgc ttgctcatca aaaacgacaa atgtaagcac   1260
tcaaaaaata aatccattag gaagcatttt tggcaaaacg gatgatccag atccactaaa   1320
tttaggcgat tttccaactc ttctaacatc aaattttaca aatcctatgc cgactagaac   1380
gccatcgcca cttaaaaaag tggatttgcc tgtaatgaac tcattaacac atggtccgat   1440
gttttcaagt gcttttagta aaccggactt gaatttcaaa caacctacta tcagtctaca   1500
aggtatcccg cctgatctat ttgatagaac aagcgatttt atggtgataa tgggtgcaaa   1560
cggcgttgtg atcactattt ggtacacatc tcctggaaac tggttatggg gctactcgct   1620
ctatgaaagc ggcaatttag gaggatatcg tgtttggcgt ctaattttac taccaaataa   1680
tgaagtcatg atagtaaatt tcaacactcg cacgacttgc ataaatactt ataaaaacgg   1740
agtaattcac tcaccttgca ataaagataa tccttttcag aaatttacgt ttcgtccaat   1800
gacaaacgga gccgtacaaa tttataacaa agctactaat tgcgtgcttg caaacgcctg   1860
ttaataatct attcggtttt gacgtttttg gggcgataaa tcttacgaca aaatgcactg   1920
atactatcga tcaacaatgg tatttgctcc cgccgccgca agttggaaga ctattttatt   1980
aggagtaaaa atgcgaaatg ttattatgat tatatttata gcaactttag gctttgcaaa   2040
accagaagat tataaaattg ctacttggaa tttgcaaggc agttcggcta taaccgaaag   2100
caaatggaat ataagcgtac gtcaaataat tagcggtgaa aatccagcag atatattagc   2160
cgttcaagaa gcaggaaatt tacctcaaac cgctcttcct acaggtagaa gcataaatca   2220
aggcggcacg atcgtaactg agcatttatg gcagctaggc agtatatcta gaccgttcca   2280
agtctatata tattatgctc aaatcgacac aggggcaaat agagtaaatt tagcaatcgt   2340
ttcacgcata aaagctgatg aaatcatcat cttgccgcct cctacggtag cttctcgtcc   2400
gctcataggt ataagaatag gaaacgacgt atttttcaac atacacgctc tagcaaatgg   2460
cggagtcgat gctccggcga taataaattc aatatttgac agatttagaa atatgccaaa   2520
tatcacttgg atgattttag gcgattttaa ccgctcacct gagagtttaa gaggaactct   2580
tggattagaa actcgcgtca gagtaacgtt tttaacacct ccggcgccta ctcaaagaag   2640
cggcggaacg cttgactggg ctatagttgg aaactcagcc ggcgatcttg tccgaactac   2700
gcttgtagca gtattgatgc tagcaaacct gcggactcac ctagtttcgg accattttcc   2760
ggtaaatttt agaaaaattg gagataacta atgaaagctt tagcaataat atttttattt   2820
gtaagcataa gttttgcaaa cgaaaacata accgacgctt ttcaaatacg caatgcaaac   2880
accggaattc ctataaatat aaagcgattt tcagggcagt ttaattacca aaactggttt   2940
ttaaatgatt taggagtaga tcctaagata aaaaaagtag ataaattttc aaattctttt   3000
ccttttggat acgtgcaatt tcaagtagca gccgacgtaa aaatgtgcct tcagatcgct   3060
cctagcggat ttttagcact aaaaaactgc aagcaagact acgatagcgg agagtttgag   3120
actatttttc agatcatccc tacaagtagt ggagctatgc agctacgatc actagttcta   3180
aaaacaaacg agtgcttagg aacatttgaa aatccaaacg tgccgatcga agatagagta   3240
ggactagtac gctgcgtttt agaattttt gtcgacatag agcctaaaca actttttgta   3300
ttttcaccgc cgcttagtga agctaaggta attagataaa acagtcggta aaagctaaaa   3360
```

-continued acggctttta cctagtttta atccaaatca aaaattccta agttctatgt ttaaatttga 3420
ttttatcaac ttcggatcga atttggtttt tggtttttgt aaattcccta aatttaagga 3480
ttcaaaaaaa ttttgcagat agtaagtttt atcataaccg ttttgactta aaacttttac 3540
catatcactg atatcgtttt cgtttagcat atctgcgtgg atagtcgttc tacactcaaa 3600
ttcaactctg ttttttagta aaatttgaag cgtttttata aatttatcat ataaattcga 3660
cgcagttata gcttcaaatt taagcctttg gagctttgaa atcaagtgat ataaaatcga 3720
tcaaactcaa attttcttct acaatctcag gactacttcc attcgtatcg actttggttt 3780
tatatccaag atccttagcc agcttcaaaa catcactaaa atgcaaactt ttagtgcatt 3840
ccccgccact taaaactacc gcacttaaaa ggttttggct gtgaatttaa aaactcgctt 3900
agatagcgca tatcaaactt gccctcaccc aaaactatat ctttgttgta gcaataaacg 3960
cagcgcatat tgcacttcgc aaaccacact atagcagcga gttcatcagg ataatcaaca 4020
acgctaaaag gcgtgatatc gtagataaat ttgtctagca tttagtaggt tctaaaaact 4080
tgatcctctc 4090

<210> SEQ ID NO 33
<211> LENGTH: 3600
<212> TYPE: DNA
<213> ORGANISM: Campylobacter coli

<400> SEQUENCE: 33
aagcttggca gattttaatg aaacacatta gcatatcaat catttttatg ttcctgcttt 60
ttgtgctgtg cttattagcc tttatgtgct ttatgcagtc aaaggaagtc ctaaaaatga 120
aggtttggtt gatattactg aaatcaatga aatgcgaggg attaaaacag aagaaatcaa 180
agctatagaa actccaaatt taagcagttt tgaaattttt tatcattatg tacttaaaaa 240
caaaaatgct tagtatgtgg cttggatgga tacttttgtt tatatggtgc gttttaggct 300
tatttcttgg cttcctattt acttgctaga aacaaaaggc tttaataaag aacaaatggg 360
tattgccttt tggcttttg aataggctgc tataccttct actttacttg caggatatat 420
ttcagataaa atttttaaag gctatagaat gcctcctgct ataggtgcta tagtgattat 480
tttctttatg attattggat attttacttc aaataatctt tatatggtta ttttctttgc 540
agctatggcg gggtgtttag tctatatacc acaattttta gcaaagtgtg caaactatgg 600
gaagtccgtc ctgcttttgc agtaggatct tgtgtaggat ttcgtggctt tatgagttat 660
gtagtcggcg cttcacttgg aacaaaagct ataggctggg ctgtggatta ctatggtagt 720
tggaatgctg gtcttatcat gctccttagt gcttgtatac tttgtatact ttgctctatc 780
ttgtgtcatt ttggtgctaa gaaaaaagag gatatatgca aaaaataaaa ttaagcctaa 840
tgtttttgat tgtaacaatc attttttag cttgttcttc aaaagaacaa caaatcaatc 900
ctttaggaag atcttacggt aaatttaacg ataacgatcc tttaaaactt ggttcaaaac 960
ctacaccccc tgtcaaacaa aaaacaccaa gcttggtaga aggtaaaaaa tttcccgcca 1020
taccacttgt cccacctgta atcactccta atacctttaa aggagataat gccgtcaaag 1080
gcccattgcc aaggctaaaa tctccaaacg aatttgcttc aaatgcttta tacgaaaaca 1140
caggtatggt aagtgatttt gtcactatta tgaatcctaa tggagcatct ttaacaatct 1200
gggctttaaa tcctggcaat tggatatggg gatatagttt atttgctagt agaccttttg 1260
gagatgcaag agcttggcag cttattgaat ttccaaacaa tacagtaatg attaaaaatg 1320
caaaaacatt tacttgctta aacgcctata gaaatggcat cgttcattat ccttgtgatc 1380
aaacaaattt tgcgcagttt tggagacttt atccgatgac taatggagct tatcaaattc 1440
aaaattttgc cacccaacaa tgtatacaaa cacctgtttc aaatgtaatg gaagaattta 1500
atttgagctt ttataatatt tatttaaccg attgtttgaa agaaaaagaa aagaatttgg 1560
atagacagtg gtatataggc gctcctattt aatttttttcg ctatgaaagg aagataatga 1620
aaaaaatagt atttttgatt ttaagtttta atgtattatt tgccgcttta gaaaattaca 1680
acaccggaac ttggaatttg caaggctcat cagctgcaac tgaaagcaaa tggaatgtta 1740
gtataagaca actcataacc ggtgcaaatc ctatggatgt tttagctgtt caagaagcgg 1800
gggttttacc tagtacagct atgatgactc ctagacaggt acaacccgtg ggcgtgggta 1860
ttcctataca tgaatacata tggaatttag gctctgtatc aagacctagc tctgtttata 1920
tatattattc tagagtggat gtaggagcaa atcgtgtgaa tttagctatc gttagcagag 1980
tgcaagcgga tgaagttttt gttttacccc ctccaacagt tgcttcaaga cctattatag 2040
gcatacgcat aggcaatgat gctttttttca atatacacgc tctagcaagt gggggaaatg 2100
acgcaggagc cattgtcgct gctgtggata tgtttttttag aaatagacct gatattaatt 2160
ggatgatttt aggcgatttt aatagagaat caggcgcctt agtaaccttg ctagatcctg 2220
acttaagagc acgcactcgc gtagttgttc cgccttcttc tacgcaaaca agtggaagaa 2280
cgattgatta tgctatcact ggaaattcca acactgcagc tttatacaac ccaccaccga 2340
tagttgcgat tttagcttta gaaggattaa gaaccttttt ggcttcagat cattttcctg 2400
taaattttag aagaccttag gagcttaata tgaaaaaatt ttttatttta ttttttgccc 2460
ttttgagctt tttgaaagca gagcctagct tggatgaatt agcagacttt actcctatgt 2520
ttgctataag atctttagaa acaggaattt ctttaagtcc ttttagaaaa acttcaaaaa 2580
ggttagaaga tcaaaattgg tttttaaaag agattgtagc aaatgatgag ctaaaagcta 2640
gggatatgca cgcaaaagat ttgccttttg gctatgttca gtttataagc cctaggggcg 2700
atgatatatg cctagctgtt ttaagtgaaa aaagttttgg caccaaatct tgcaaacaag 2760
atttgcaaga tggaacaatg cagactattt tttctatcat accaatgaca aatggttcta 2820
tacaaattag atctttaacc aatggtggca atcaatgcat gagcactttt cctgactcta 2880
gtatcgccat agaaaatcgc tttggtttag gagaatgcct tttggatcgt tctatcgtaa 2940
ctgtattaag caaacttttc tttttctccc ctgctataat cgaagcaagc gcaatttact 3000
aacacttttc taacaaaacc aagctttcat ggcttggttt ataacttgat ttaactcaag 3060
gatttaacaa aatcaaactc accgccatta ccgccattcc taaaacaagt ccataaaggc 3120
tatcgtgggc tttatcataa gtctttgccg caggcaataa ctcatcaaaa gagataaaca 3180
ccatgatccc agccactaca gcaaaggtga tggctaaagt aagctcattc atgataggca 3240
agatcaaaaa cgctcccaca atcgctccca taggctccgc tatacccgaa agtgcagagt 3300
aaataaaggc ttttttctta tcctttgtag catgataaat cggtaaagaa actgccttcc 3360
ttcagggata ttgtgtatag ctacagccac agcgatagcc acaccaaagc taagattatc 3420
aaggcttgag ataaaagtcg caaaaccctc aggaaaatta tgtatcgcta tggcaagtgc 3480
agtaaatatc cctgttcttt tcaatgcctt tacattgatc ttttttaaag gttcacctgc 3540
atgaaaagcg ggtgcttttt cattttttttg aggcaagggg caaattttaa gctcacttag 3600

<210> SEQ ID NO 34
<211> LENGTH: 1462

-continued

<212> TYPE: DNA
<213> ORGANISM: Campylobacter jejuni
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (272)..(272)
<223> OTHER INFORMATION: n is a, c, g, or t
<220> FEATURE:
<221> NAME/KEY: misc_feature
<222> LOCATION: (521)..(521)
<223> OTHER INFORMATION: n is a, c, g, or t
<220> FEATURE:
<221> NAME/KEY: misc_feature
<222> LOCATION: (637)..(637)
<223> OTHER INFORMATION: n is a, c, g, or t
<220> FEATURE:
<221> NAME/KEY: misc_feature
<222> LOCATION: (667)..(668)
<223> OTHER INFORMATION: n is a, c, g, or t
<220> FEATURE:
<221> NAME/KEY: misc_feature
<222> LOCATION: (740)..(740)
<223> OTHER INFORMATION: n is a, c, g, or t
<220> FEATURE:
<221> NAME/KEY: misc_feature
<222> LOCATION: (903)..(903)
<223> OTHER INFORMATION: n is a, c, g, or t
<220> FEATURE:
<221> NAME/KEY: misc_feature
<222> LOCATION: (907)..(907)
<223> OTHER INFORMATION: n is a, c, g, or t
<220> FEATURE:
<221> NAME/KEY: misc_feature
<222> LOCATION: (936)..(942)
<223> OTHER INFORMATION: n is a, c, g, or t
<220> FEATURE:
<221> NAME/KEY: misc_feature
<222> LOCATION: (1147)..(1147)
<223> OTHER INFORMATION: n is a, c, g, or t
<220> FEATURE:
<221> NAME/KEY: misc_feature
<222> LOCATION: (1255)..(1255)
<223> OTHER INFORMATION: n is a, c, g, or t
<220> FEATURE:
<221> NAME/KEY: misc_feature
<222> LOCATION: (1381)..(1381)
<223> OTHER INFORMATION: n is a, c, g, or t
<220> FEATURE:
<221> NAME/KEY: misc_feature
<222> LOCATION: (1451)..(1451)
<223> OTHER INFORMATION: n is a, c, g, or t
<220> FEATURE:
<221> NAME/KEY: misc_feature
<222> LOCATION: (1453)..(1454)
<223> OTHER INFORMATION: n is a, c, g, or t
<220> FEATURE:
<221> NAME/KEY: misc_feature
<222> LOCATION: (1457)..(1459)
<223> OTHER INFORMATION: n is a, c, g, or t

<400> SEQUENCE: 34

```
ntttatggag agtttgatcc tggctcagag tgaacgctgg cggcgtgcct aatacatgca      60

agtcgaacga tgaagcttct agcttgctag aagtggatta gtggcgcacg ggtgagtaag     120

gtatagttaa tctgccctac acaagaggac aacagttgga aacgactgct aatactctat     180

actcctgctt aacacaagtt gagtagggaa agtttttcgg tgtaggatga gactatatag     240

tatcagctag ttggtaaggt aatggcttac cnaggctatg acgcttaact ggtctgagag     300

gatgatcagt cacactggaa ctgagacacg gtccagactc ctacgggagg cagcagtagg     360

gaatattgcg caatgggga aaccctgacg cagcaacgcc gcgtggagga tgacactttt     420
```

-continued

```
cggagcgtaa actccttttc ttagggaaga attctgacgg tacctaagga ataagcaccg    480

gctaactccg tgccagcagc cgcggtaata cggagggtgc nagcgttact cggaatcact    540

gggcgtaaag ggcgcgtagg cggattatca agtctcttgt gaaatctaat ggcttaacca    600

ttaaactgct tgggaaactg atagtctaga gtgaggnaga ggcagatgga attggtggtg    660

taggggnnaa atccgtagat atcaccaaga atacccattg cgaaggcgat ctgctggaac    720

tcaactgacg ctaaggcgcn aaagcgtggg gagcaaacag gattagatac cctggtagtc    780

cacgccctaa acgatgtaca ctagttgttg gggtgctagt catctcagta atgcagctaa    840

cgcattaagt gtaccgcctg gggagtacgg tcgcaagatt aaaactcaaa ggaatagacg    900

ggnaccngca caagcggtgg agcatgtggt ttaatnnnnn nntacgcgaa gaaccttacc    960

tgggcttgat atcctaagaa ccttatagag atatgagggt gctagcttgc tagaacttag   1020

agacaggtgc tgcacggctg tcgtcagctc gtgtcgtgag atgttgggtt aagtcccgca   1080

acgagcgcaa cccacgtatt tagttgctaa cggttcggcc gagcactcta aatagactgc   1140

cttcgtnagg aggaggaagg tgtggacgac gtcaagtcat catggccctt atgcccaggg   1200

cgacacacgt gctacaatgg catatacaat gagacgcaat accgcgaggt ggagncaaat   1260

ctataaaata tgtcccagtt cggattgttc tctgcaactc gagagcatga agccggaatc   1320

gctagtaatc gtagatcagc catgctacgg tgaatacgtt cccgggtctt gtactcaccg   1380

nccgtcacac catgggagtt gatttcactc gaagccggaa tactaaacta gttaccgtcc   1440

acagtggaat nanngannng gg                                            1462
```

<210> SEQ ID NO 35
<211> LENGTH: 1467
<212> TYPE: DNA
<213> ORGANISM: Campylobacter coli
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t
<220> FEATURE:
<221> NAME/KEY: misc_feature
<222> LOCATION: (521)..(521)
<223> OTHER INFORMATION: n is a, c, g, or t
<220> FEATURE:
<221> NAME/KEY: misc_feature
<222> LOCATION: (740)..(740)
<223> OTHER INFORMATION: n is a, c, g, or t
<220> FEATURE:
<221> NAME/KEY: misc_feature
<222> LOCATION: (774)..(774)
<223> OTHER INFORMATION: n is a, c, g, or t
<220> FEATURE:
<221> NAME/KEY: misc_feature
<222> LOCATION: (789)..(789)
<223> OTHER INFORMATION: n is a, c, g, or t
<220> FEATURE:
<221> NAME/KEY: misc_feature
<222> LOCATION: (827)..(827)
<223> OTHER INFORMATION: n is a, c, g, or t
<220> FEATURE:
<221> NAME/KEY: misc_feature
<222> LOCATION: (836)..(836)
<223> OTHER INFORMATION: n is a, c, g, or t
<220> FEATURE:
<221> NAME/KEY: misc_feature
<222> LOCATION: (871)..(946)
<223> OTHER INFORMATION: n is a, c, g, or t
<220> FEATURE:
<221> NAME/KEY: misc_feature -continued
<222> LOCATION: (1151)..(1151)
<223> OTHER INFORMATION: n is a, c, g, or t
<220> FEATURE:
<221> NAME/KEY: misc_feature
<222> LOCATION: (1155)..(1155)
<223> OTHER INFORMATION: n is a, c, g, or t
<220> FEATURE:
<221> NAME/KEY: misc_feature
<222> LOCATION: (1259)..(1259)
<223> OTHER INFORMATION: n is a, c, g, or t
<220> FEATURE:
<221> NAME/KEY: misc_feature
<222> LOCATION: (1383)..(1383)
<223> OTHER INFORMATION: n is a, c, g, or t

<400> SEQUENCE: 35
ntttatggag agtttgatcc tggctcagag tgaacgctgg cggcgtgcct aatacatgca 60
agtcgaacga tgaagcttct agcttgctag aagtggatta gtggcgcacg ggtgagtaag 120
gtatagttaa tctgccctac acaagaggac aacagttgga aacgactgct aatactctat 180
actcctgctt aacacaagtt gagtagggaa agtttttcgg tgtaggatga gactatatag 240
tatcagctag ttggtaaggt aatggcttac caaggctatg acgcttaact ggtctgagag 300
gatgatcagt cacactggaa ctgagacacg gtccagactc ntacgggagg cagcagtagg 360
gaatattgcg caatgggga aaccctgacg cagcaacgcc gcgtggagga tgacactttt 420
cggagcgtaa actccttttc ttagggaaga attctgacgg tacctaagga ataagcaccg 480
gctaactccg tgccagcagc cgcggtaata cggagggtgc nagcgttact cggaatcact 540
gggcgtaaag gacgcgtagg cggattatca agtcttttgt gaaatctaat ggcttaacca 600
ttaaactgct tgagaaactg ataatctaga gtgagggaga ggcagatgga attggtggtg 660
taggggtaaa atccgtagag atcaccaaga atacccattg cgaaggcgat ctgctagaac 720
tcaactgacg ctaatgcgtn aaagcgtggg gagcaaacag gattagatac cctngtagtc 780
cacgccctna acgatgtata ctcgttgttg ctctgctagt cagggcngta atgcanctaa 840
cggattaagt ataccgcctg gggagtacgg nnnnnnnnnn nnnnnnnnnn nnnnnnnnnn 900
nnnnnnnnnn nnnnnnnnnn nnnnnnnnnn nnnnnnnnnn nnnnnntacg cgaagaacct 960
tacctgggct tgatatccta agaacctttt agagataaga gggtgctagc ttgctagaac 1020
ttagagacag gtgctgcacg gctgtcgtca gctcgtgtcg tgagatgttg ggttaagtcc 1080
cgcaacgagc gcaacccacg tatttagttg ctaacggttc ggccgagcac tctaaataga 1140
ctgccttcgt naggnggagg aaggtgtgga cgacgtcaag tcatcatggc ccttatgccc 1200
agggcgacac acgtgctaca atggcatata caatgagacg caataccgcg aggtggagnc 1260
aaatctataa aatatgtccc agttcggatt gttctctgca actcgagagc atgaagccgg 1320
aatcgctagt aatcgtagat cagccatgct acggtgaata cgttcccggg tcttgtactc 1380
acngcccgtc acaccatggg agttgatttc actcgaagcc ggaatactaa actagttacc 1440
gtccacagtg gaatcagcga ctggggt 1467

<210> SEQ ID NO 36
<211> LENGTH: 1461
<212> TYPE: DNA
<213> ORGANISM: Campylobacter fetus
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (88)..(88)

<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (214)..(214)
<223> OTHER INFORMATION: n is a, c, g, or t
<220> FEATURE:
<221> NAME/KEY: misc_feature
<222> LOCATION: (278)..(278)
<223> OTHER INFORMATION: n is a, c, g, or t
<220> FEATURE:
<221> NAME/KEY: misc_feature
<222> LOCATION: (436)..(436)
<223> OTHER INFORMATION: n is a, c, g, or t
<220> FEATURE:
<221> NAME/KEY: misc_feature
<222> LOCATION: (521)..(521)
<223> OTHER INFORMATION: n is a, c, g, or t
<220> FEATURE:
<221> NAME/KEY: misc_feature
<222> LOCATION: (923)..(925)
<223> OTHER INFORMATION: n is a, c, g, or t
<220> FEATURE:
<221> NAME/KEY: misc_feature
<222> LOCATION: (940)..(942)
<223> OTHER INFORMATION: n is a, c, g, or t

<400> SEQUENCE: 36

```
ttatggagag tttgatcctg gctcagagtg aacgcnggcg gcgtgcctaa tacatgcaag     60

tcgaacggag tattaagaga gcttgctntn ttaatacnta gtggcgcacg ggtgagtaat    120

gtatagttaa tctgccctac actggaggac aacagttaga aatgactgct aatactccat    180

actccttctt aacataagtt aagtcgggaa agtntttcgg tgtaggatga gactatattg    240

tatcagctag ttggtaaggt aatggcttac caaggctntg acgcataact ggtctgagag    300

gatgatcagt cacactggaa ctgagacacg gtccagactc ctacgggagg cagcagtagg    360

gaatattgct caatggggga aaccctgaag cagcaacgcc gcgtggagga tgacactttt    420

cggagcgtaa actccntttg ttagggaaga accatgacgg tacctaacga ataagcaccg    480

gctaactccg tgccagcagc cgcggtaata cggagggtgc nagcgttact cggaatcact    540

gggcgtaaag gacgcgtagg cggattatca agtcttttgt gaaatctaac agctaaactg    600

ttaaactgct tgagaaactg ataatctaga gtgagggaga ggcagatgga attggtggtg    660

taggggtaaa atccgtagag atcaccagga atacccattg cgaaggcgat ctgctggaac    720

tcaactgacg ctaatgcgtg aaagcgtggg gagcaaacag gattagatac cctggtagtc    780

cacgctctaa acgatgtata ctagttgttg ctgtgctagt cacggcagta atgcacctaa    840

cggattaagt ataccgcctg gggagtacgg tcgcaagatt aaaactcaaa ggaatagacg    900

gggacccgca caagcggtgg agnnngtggt ttaattcgan nntacgcgaa gaaccttacc    960

tgggcttgat atccaactaa tctcttagag ataagagagt gctagcttgc tagaaagttg   1020

agacaggtgc tgcacggctg tcgtcagctc gtgtcgtgag atgttgggtt aagtcccgca   1080

acgagcgcaa cccacgtatt tagttgctaa cagttcggct gagcactcta aatagactgc   1140

cttcgcaagg aggaggaagg tgtggacgac gtcaagtcat catggccctt atgcccaggg   1200

cgacacacgt gctacaatgg catatacaat gagatgcaat atcgcgagat ggagcaaatc   1260

tataaaatat gtcccagttc ggattggagt ctgcaactcg actccatgaa gccggaatcg   1320
```

ctagtaatcg tagatcagcc atgctacggt gaatacgttc ccgggtcttg tactcaccgc 1380
ccgtcacacc atgggagttg atttcactcg aagtcggaat gctaaactag ctaccgccca 1440
cagtggaatc agcgactggg g 1461

<210> SEQ ID NO 37
<211> LENGTH: 28
<212> TYPE: DNA
<213> ORGANISM: Artificial
<220> FEATURE:
<223> OTHER INFORMATION: An artificially synthesized primer sequence

<400> SEQUENCE: 37
gcaaaatctt gtcaagatga tctaaaag 28

<210> SEQ ID NO 38
<211> LENGTH: 25
<212> TYPE: DNA
<213> ORGANISM: Artificial
<220> FEATURE:
<223> OTHER INFORMATION: An artificially synthesized primer sequence

<400> SEQUENCE: 38
tccaaaacta aagaacgaat ttgca 25

<210> SEQ ID NO 39
<211> LENGTH: 36
<212> TYPE: DNA
<213> ORGANISM: Artificial
<220> FEATURE:
<223> OTHER INFORMATION: An artificially synthesized probe sequence

<400> SEQUENCE: 39
aaactgtatt ttctataatg ccaacaacaa cttcag 36

<210> SEQ ID NO 40
<211> LENGTH: 23
<212> TYPE: DNA
<213> ORGANISM: Artificial
<220> FEATURE:
<223> OTHER INFORMATION: An artificially synthesized primer sequence

<400> SEQUENCE: 40
tttaaccaat ggtggcaatc aat 23

<210> SEQ ID NO 41
<211> LENGTH: 25
<212> TYPE: DNA
<213> ORGANISM: Artificial
<220> FEATURE:
<223> OTHER INFORMATION: An artificially synthesized primer sequence

<400> SEQUENCE: 41
attctcctaa accaaagcga ttttc 25

<210> SEQ ID NO 42
<211> LENGTH: 32
<212> TYPE: DNA
<213> ORGANISM: Artificial
<220> FEATURE:
<223> OTHER INFORMATION: An artificially synthesized probe sequence

<400> SEQUENCE: 42
catgagcact tttcctgact ctagtatcgc ca 32

<210> SEQ ID NO 43
<211> LENGTH: 23
<212> TYPE: DNA
<213> ORGANISM: Artificial
<220> FEATURE:
<223> OTHER INFORMATION: An artificially synthesized primer sequence

<400> SEQUENCE: 43
cttttccttt tggatacgtg caa 23

<210> SEQ ID NO 44
<211> LENGTH: 23
<212> TYPE: DNA
<213> ORGANISM: Artificial
<220> FEATURE:
<223> OTHER INFORMATION: An artificially synthesized primer sequence

<400> SEQUENCE: 44
aaaaatccgc taggagcgat ctg 23

<210> SEQ ID NO 45
<211> LENGTH: 29
<212> TYPE: DNA
<213> ORGANISM: Artificial
<220> FEATURE:
<223> OTHER INFORMATION: An artificially synthesized probe sequence

<400> SEQUENCE: 45
caagtagcag ccgacgtaaa aatgtgcct 29

<210> SEQ ID NO 46
<211> LENGTH: 268
<212> TYPE: PRT
<213> ORGANISM: Campylobacter jejuni

<400> SEQUENCE: 46

```
Met Gln Lys Ile Ile Val Phe Ile Leu Cys Cys Phe Met Thr Phe Phe
1               5                   10                  15

Leu Tyr Ala Cys Ser Ser Lys Phe Glu Asn Val Asn Pro Leu Gly Arg
            20                  25                  30

Ser Phe Gly Glu Phe Glu Asp Thr Asp Pro Leu Lys Leu Gly Leu Glu
        35                  40                  45

Pro Thr Phe Pro Thr Asn Gln Glu Ile Pro Ser Leu Ile Ser Gly Ala
    50                  55                  60

Asp Leu Val Pro Ile Thr Pro Ile Thr Pro Pro Leu Thr Arg Thr Ser
65                  70                  75                  80

Asn Ser Ala Asn Asn Asn Ala Ala Asn Gly Ile Asn Pro Arg Phe Lys
                85                  90                  95

Asp Glu Ala Phe Asn Asp Val Leu Ile Phe Glu Asn Arg Pro Ala Val
            100                 105                 110

Ser Asp Phe Leu Thr Ile Leu Gly Pro Ser Gly Ala Ala Leu Thr Val
        115                 120                 125

Trp Ala Leu Ala Gln Gly Asn Trp Ile Trp Gly Tyr Thr Leu Ile Asp
    130                 135                 140

Ser Lys Gly Phe Gly Asp Ala Arg Val Trp Gln Leu Leu Leu Tyr Pro
145                 150                 155                 160

Asn Asp Phe Ala Met Ile Lys Asn Ala Lys Thr Asn Thr Cys Leu Asn
                165                 170                 175

Ala Tyr Gly Asn Gly Ile Val His Tyr Pro Cys Asp Ala Ser Asn His
            180                 185                 190
```

-continued

```
Ala Gln Met Trp Lys Leu Ile Pro Met Ser Asn Thr Ala Val Gln Ile
        195                 200                 205

Lys Asn Leu Gly Asn Gly Lys Cys Ile Gln Ala Pro Ile Thr Asn Leu
    210                 215                 220

Tyr Gly Asp Phe His Lys Val Phe Lys Ile Phe Thr Val Glu Cys Ala
225                 230                 235                 240

Lys Lys Asp Asn Phe Asp Gln Gln Trp Phe Leu Thr Thr Pro Pro Phe
                245                 250                 255

Thr Ala Lys Pro Leu Tyr Arg Gln Gly Glu Val Arg
            260                 265


<210> SEQ ID NO 47
<211> LENGTH: 265
<212> TYPE: PRT
<213> ORGANISM: Campylobacter jejuni

<400> SEQUENCE: 47

Met Lys Lys Ile Ile Cys Leu Phe Leu Ser Phe Asn Leu Ala Phe Ala
1               5                   10                  15

Asn Leu Glu Asn Phe Asn Val Gly Thr Trp Asn Leu Gln Gly Ser Ser
            20                  25                  30

Ala Ala Thr Glu Ser Lys Trp Ser Val Ser Val Arg Gln Leu Val Ser
        35                  40                  45

Gly Ala Asn Pro Leu Asp Ile Leu Met Ile Gln Glu Ala Gly Thr Leu
    50                  55                  60

Pro Arg Thr Ala Thr Pro Thr Gly Arg His Val Gln Gln Gly Gly Thr
65                  70                  75                  80

Pro Ile Asp Glu Tyr Glu Trp Asn Leu Gly Thr Leu Ser Arg Pro Asp
                85                  90                  95

Arg Val Phe Ile Tyr Tyr Ser Arg Val Asp Val Gly Ala Asn Arg Val
            100                 105                 110

Asn Leu Ala Ile Val Ser Arg Met Gln Ala Glu Glu Val Ile Val Leu
        115                 120                 125

Pro Pro Pro Thr Thr Val Ser Arg Pro Ile Ile Gly Ile Arg Asn Gly
    130                 135                 140

Asn Asp Ala Phe Phe Asn Ile His Ala Leu Ala Asn Gly Gly Thr Asp
145                 150                 155                 160

Val Gly Ala Ile Ile Thr Ala Val Asp Ala His Phe Ala Asn Met Pro
                165                 170                 175

Gln Val Asn Trp Met Ile Ala Gly Asp Phe Asn Arg Asp Pro Ser Thr
            180                 185                 190

Ile Thr Ser Thr Val Asp Arg Glu Leu Ala Asn Arg Ile Arg Val Val
        195                 200                 205

Phe Pro Thr Ser Ala Thr Gln Ala Ser Gly Gly Thr Leu Asp Tyr Ala
    210                 215                 220

Ile Thr Gly Asn Ser Asn Arg Gln Gln Thr Tyr Thr Pro Pro Leu Leu
225                 230                 235                 240

Ala Ala Ile Leu Met Leu Ala Ser Leu Arg Ser His Ile Val Ser Asp
                245                 250                 255

His Phe Pro Val Asn Phe Arg Lys Phe
            260                 265


<210> SEQ ID NO 48
<211> LENGTH: 189
<212> TYPE: PRT
```

<213> ORGANISM: Campylobacter jejuni

<400> SEQUENCE: 48

```
Met Lys Lys Ile Ile Thr Leu Phe Phe Met Phe Ile Thr Leu Ala Phe
1               5                   10                  15

Ala Thr Pro Thr Gly Asp Leu Lys Asp Phe Thr Glu Met Val Ser Ile
            20                  25                  30

Arg Ser Leu Glu Thr Gly Ile Phe Leu Ser Ala Phe Arg Asp Thr Ser
        35                  40                  45

Lys Asp Pro Ile Asp Gln Asn Trp Asn Ile Lys Glu Ile Val Leu Ser
    50                  55                  60

Asp Glu Leu Lys Gln Lys Asp Lys Leu Ala Asp Glu Leu Pro Phe Gly
65                  70                  75                  80

Tyr Val Gln Phe Thr Asn Pro Lys Glu Ser Asp Leu Cys Leu Ala Ile
                85                  90                  95

Leu Glu Asp Gly Thr Phe Gly Ala Lys Ser Cys Gln Asp Asp Leu Lys
            100                 105                 110

Asp Gly Lys Leu Glu Thr Val Phe Ser Ile Met Pro Thr Thr Thr Ser
        115                 120                 125

Ala Val Gln Ile Arg Ser Leu Val Leu Glu Ser Asp Glu Cys Ile Val
    130                 135                 140

Thr Phe Phe Asn Pro Asn Ile Pro Ile Gln Lys Arg Phe Gly Ile Ala
145                 150                 155                 160

Pro Cys Thr Leu Asp Pro Ile Phe Phe Ala Glu Val Asn Glu Leu Met
                165                 170                 175

Ile Ile Thr Pro Pro Leu Thr Ala Ala Thr Pro Leu Glu
            180                 185
```

<210> SEQ ID NO 49
<211> LENGTH: 162
<212> TYPE: PRT
<213> ORGANISM: Campylobacter fetus

<400> SEQUENCE: 49

```
Met Lys Lys Ala Phe Thr Met Val Glu Leu Ala Phe Val Ile Val Ile
1               5                   10                  15

Thr Gly Leu Leu Ala Ser Val Ser Ile Pro Lys Leu Thr Met Ser Arg
            20                  25                  30

Thr Asp Ala Glu Val Ala Lys Ile Val Val Asp Ile Lys Asn Thr Phe
        35                  40                  45

Asp Lys Ile Asn Ser Ile Tyr Ile Ser Asn Ser Ser Val Asn Lys Lys
    50                  55                  60

Leu Asn Ala Asp Lys Asn Glu Val Asp Ser Tyr Leu His Leu Arg Leu
65                  70                  75                  80

Leu Ile Gly Asn Asp Ser Thr Leu Ser Asp Phe Glu Ala Ile Lys Arg
                85                  90                  95

Gly Ala Lys Glu His Pro Trp Ala Val Glu Cys Leu Phe Tyr Ser Ile
            100                 105                 110

Asp Asn Ser Thr Ile Lys Phe Lys Thr Met Trp Gln Gln Ser Ser Ile
        115                 120                 125

Ser Trp Lys Lys Thr Cys Asn Ala Leu Tyr Leu His Pro Thr Met Lys
    130                 135                 140

Glu Trp Ile Gln Asn Gly Ile Gln Leu Gly Gly Asp Ser Ile Leu Lys
145                 150                 155                 160

Asn Ser
```

<210> SEQ ID NO 50
<211> LENGTH: 234
<212> TYPE: PRT
<213> ORGANISM: Campylobacter fetus

<400> SEQUENCE: 50

```
Met Thr Lys Ile Ile Phe Lys His Ile Lys Asn Ser Leu Ile Leu Leu
1               5                   10                  15

Phe Cys Ile Ala Leu Phe Ser Ala Cys Ser Ser Lys Thr Thr Asn Val
            20                  25                  30

Ser Thr Gln Lys Ile Asn Pro Leu Gly Ser Ile Phe Gly Lys Thr Asp
        35                  40                  45

Asp Pro Asp Pro Leu Asn Leu Gly Asp Phe Pro Thr Leu Leu Thr Ser
    50                  55                  60

Asn Phe Thr Asn Pro Met Pro Thr Arg Thr Pro Ser Pro Leu Lys Lys
65                  70                  75                  80

Val Asp Leu Pro Val Met Asn Ser Leu Thr His Gly Pro Met Phe Ser
                85                  90                  95

Ser Ala Phe Ser Lys Pro Asp Leu Asn Phe Lys Gln Pro Thr Ile Ser
            100                 105                 110

Leu Gln Gly Ile Pro Pro Asp Leu Phe Asp Arg Thr Ser Asp Phe Met
        115                 120                 125

Val Ile Met Gly Ala Asn Gly Val Val Ile Thr Ile Trp Tyr Thr Ser
    130                 135                 140

Pro Gly Asn Trp Leu Trp Gly Tyr Ser Leu Tyr Glu Ser Gly Asn Leu
145                 150                 155                 160

Gly Gly Tyr Arg Val Trp Arg Leu Ile Leu Leu Pro Asn Asn Glu Val
                165                 170                 175

Met Ile Val Asn Phe Asn Thr Arg Thr Thr Cys Ile Asn Thr Tyr Lys
            180                 185                 190

Asn Gly Val Ile His Ser Pro Cys Asn Lys Asp Asn Pro Phe Gln Lys
        195                 200                 205

Phe Thr Phe Arg Pro Met Thr Asn Gly Ala Val Gln Ile Tyr Asn Lys
    210                 215                 220

Ala Thr Asn Cys Val Leu Ala Asn Ala Cys
225                 230
```

<210> SEQ ID NO 51
<211> LENGTH: 266
<212> TYPE: PRT
<213> ORGANISM: Campylobacter fetus

<400> SEQUENCE: 51

```
Met Arg Asn Val Ile Met Ile Ile Phe Ile Ala Thr Leu Gly Phe Ala
1               5                   10                  15

Lys Pro Glu Asp Tyr Lys Ile Ala Thr Trp Asn Leu Gln Gly Ser Ser
            20                  25                  30

Ala Ile Thr Glu Ser Lys Trp Asn Ile Ser Val Arg Gln Ile Ile Ser
        35                  40                  45

Gly Glu Asn Pro Ala Asp Ile Leu Ala Val Gln Glu Ala Gly Asn Leu
    50                  55                  60

Pro Gln Thr Ala Leu Pro Thr Gly Arg Ser Ile Asn Gln Gly Gly Thr
65                  70                  75                  80

Ile Val Thr Glu His Leu Trp Gln Leu Gly Ser Ile Ser Arg Pro Phe
                85                  90                  95
```

-continued

```
Gln Val Tyr Ile Tyr Tyr Ala Gln Ile Asp Thr Gly Ala Asn Arg Val
            100                 105                 110

Asn Leu Ala Ile Val Ser Arg Ile Lys Ala Asp Glu Ile Ile Ile Leu
        115                 120                 125

Pro Pro Pro Thr Val Ala Ser Arg Pro Leu Ile Gly Ile Arg Ile Gly
    130                 135                 140

Asn Asp Val Phe Phe Asn Ile His Ala Leu Ala Asn Gly Gly Val Asp
145                 150                 155                 160

Ala Pro Ala Ile Ile Asn Ser Ile Phe Asp Arg Phe Arg Asn Met Pro
                165                 170                 175

Asn Ile Thr Trp Met Ile Leu Gly Asp Phe Asn Arg Ser Pro Glu Ser
            180                 185                 190

Leu Arg Gly Thr Leu Gly Leu Glu Thr Arg Val Arg Val Thr Phe Leu
        195                 200                 205

Thr Pro Pro Ala Pro Thr Gln Arg Ser Gly Gly Thr Leu Asp Trp Ala
    210                 215                 220

Ile Val Gly Asn Ser Ala Gly Asp Leu Val Arg Thr Thr Leu Val Ala
225                 230                 235                 240

Val Leu Met Leu Ala Asn Leu Arg Thr His Leu Val Ser Asp His Phe
                245                 250                 255

Pro Val Asn Phe Arg Lys Phe Gly Asp Asn
            260                 265


<210> SEQ ID NO 52
<211> LENGTH: 182
<212> TYPE: PRT
<213> ORGANISM: Campylobacter fetus

<400> SEQUENCE: 52

Met Lys Ala Leu Ala Ile Ile Phe Leu Phe Val Ser Ile Ser Phe Ala
1               5                   10                  15

Asn Glu Asn Ile Thr Asp Ala Phe Gln Ile Arg Asn Ala Asn Thr Gly
            20                  25                  30

Ile Pro Ile Asn Ile Lys Arg Phe Ser Gly Gln Phe Asn Tyr Gln Asn
        35                  40                  45

Trp Phe Leu Asn Asp Leu Gly Val Asp Pro Lys Ile Lys Lys Val Asp
    50                  55                  60

Lys Phe Ser Asn Ser Phe Pro Phe Gly Tyr Val Gln Phe Gln Val Ala
65                  70                  75                  80

Ala Asp Val Lys Met Cys Leu Gln Ile Ala Pro Ser Gly Phe Leu Ala
                85                  90                  95

Leu Lys Asn Cys Lys Gln Asp Tyr Asp Ser Gly Glu Phe Glu Thr Ile
            100                 105                 110

Phe Gln Ile Ile Pro Thr Ser Ser Gly Ala Met Gln Leu Arg Ser Leu
        115                 120                 125

Val Leu Lys Thr Asn Glu Cys Leu Gly Thr Phe Glu Asn Pro Asn Val
    130                 135                 140

Pro Ile Glu Asp Arg Val Gly Leu Val Arg Cys Val Leu Glu Phe Phe
145                 150                 155                 160

Val Asp Ile Glu Pro Lys Gln Leu Phe Val Phe Ser Pro Pro Leu Ser
                165                 170                 175

Glu Ala Lys Val Ile Arg
            180
```

-continued

<210> SEQ ID NO 53
<211> LENGTH: 60
<212> TYPE: PRT
<213> ORGANISM: Campylobacter fetus

<400> SEQUENCE: 53

```
Met Leu Asn Glu Asn Asp Ile Ser Asp Met Val Lys Val Leu Ser Gln
1               5                   10                  15

Asn Gly Tyr Asp Lys Thr Tyr Tyr Leu Gln Asn Phe Phe Glu Ser Leu
            20                  25                  30

Asn Leu Gly Asn Leu Gln Lys Pro Lys Thr Lys Phe Asp Pro Lys Leu
        35                  40                  45

Ile Lys Ser Asn Leu Asn Ile Glu Leu Arg Asn Phe
    50                  55                  60
```

<210> SEQ ID NO 54
<211> LENGTH: 76
<212> TYPE: PRT
<213> ORGANISM: Campylobacter fetus

<400> SEQUENCE: 54

```
Met Leu Asp Lys Phe Ile Tyr Asp Ile Thr Pro Phe Ser Val Val Asp
1               5                   10                  15

Tyr Pro Asp Glu Leu Ala Ala Ile Val Trp Phe Ala Lys Cys Asn Met
            20                  25                  30

Arg Cys Val Tyr Cys Tyr Asn Lys Asp Ile Val Leu Gly Glu Gly Lys
        35                  40                  45

Phe Asp Met Arg Tyr Leu Ser Glu Phe Leu Asn Ser Gln Pro Lys Pro
    50                  55                  60

Phe Lys Cys Gly Ser Phe Lys Trp Arg Gly Met His
65                  70                  75
```

<210> SEQ ID NO 55
<211> LENGTH: 58
<212> TYPE: PRT
<213> ORGANISM: Campylobacter coli

<400> SEQUENCE: 55

```
Met Pro Pro Ala Ile Gly Ala Ile Val Ile Ile Phe Phe Met Ile Ile
1               5                   10                  15

Gly Tyr Phe Thr Ser Asn Asn Leu Tyr Met Val Ile Phe Phe Ala Ala
            20                  25                  30

Met Ala Gly Cys Leu Val Tyr Ile Pro Gln Phe Leu Ala Lys Cys Ala
        35                  40                  45

Asn Tyr Gly Lys Ser Val Leu Leu Leu Gln
    50                  55
```

<210> SEQ ID NO 56
<211> LENGTH: 58
<212> TYPE: PRT
<213> ORGANISM: Campylobacter coli

<400> SEQUENCE: 56

```
Met Ser Tyr Val Val Gly Ala Ser Leu Gly Thr Lys Ala Ile Gly Trp
1               5                   10                  15

Ala Val Asp Tyr Tyr Gly Ser Trp Asn Ala Gly Leu Ile Met Leu Leu
            20                  25                  30

Ser Ala Cys Ile Leu Cys Ile Leu Cys Ser Ile Leu Cys His Phe Gly
        35                  40                  45
```

Ala Lys Lys Lys Glu Asp Ile Cys Lys Lys
    50                  55

<210> SEQ ID NO 57
<211> LENGTH: 258
<212> TYPE: PRT
<213> ORGANISM: Campylobacter coli

<400> SEQUENCE: 57

Met Gln Lys Ile Lys Leu Ser Leu Met Phe Leu Ile Val Thr Ile Ile
1               5                   10                  15

Phe Leu Ala Cys Ser Ser Lys Glu Gln Gln Ile Asn Pro Leu Gly Arg
            20                  25                  30

Ser Tyr Gly Lys Phe Asn Asp Asn Asp Pro Leu Lys Leu Gly Ser Lys
        35                  40                  45

Pro Thr Pro Pro Val Lys Gln Lys Thr Pro Ser Leu Val Glu Gly Lys
    50                  55                  60

Lys Phe Pro Ala Ile Pro Leu Val Pro Pro Val Ile Thr Pro Asn Thr
65                  70                  75                  80

Phe Lys Gly Asp Asn Ala Val Lys Gly Pro Leu Pro Arg Leu Lys Ser
                85                  90                  95

Pro Asn Glu Phe Ala Ser Asn Ala Leu Tyr Glu Asn Thr Gly Met Val
            100                 105                 110

Ser Asp Phe Val Thr Ile Met Asn Pro Asn Gly Ala Ser Leu Thr Ile
        115                 120                 125

Trp Ala Leu Asn Pro Gly Asn Trp Ile Trp Gly Tyr Ser Leu Phe Ala
    130                 135                 140

Ser Arg Pro Phe Gly Asp Ala Arg Ala Trp Gln Leu Ile Glu Phe Pro
145                 150                 155                 160

Asn Asn Thr Val Met Ile Lys Asn Ala Lys Thr Phe Thr Cys Leu Asn
                165                 170                 175

Ala Tyr Arg Asn Gly Ile Val His Tyr Pro Cys Asp Gln Thr Asn Phe
            180                 185                 190

Ala Gln Phe Trp Arg Leu Tyr Pro Met Thr Asn Gly Ala Tyr Gln Ile
        195                 200                 205

Gln Asn Phe Ala Thr Gln Gln Cys Ile Gln Thr Pro Val Ser Asn Val
    210                 215                 220

Met Glu Glu Phe Asn Leu Ser Phe Tyr Asn Ile Tyr Leu Thr Asp Cys
225                 230                 235                 240

Leu Lys Glu Lys Glu Lys Asn Leu Asp Arg Gln Trp Tyr Ile Gly Ala
                245                 250                 255

Pro Ile

<210> SEQ ID NO 58
<211> LENGTH: 267
<212> TYPE: PRT
<213> ORGANISM: Campylobacter coli

<400> SEQUENCE: 58

Met Lys Lys Ile Val Phe Leu Ile Leu Ser Phe Asn Val Leu Phe Ala
1               5                   10                  15

Ala Leu Glu Asn Tyr Asn Thr Gly Thr Trp Asn Leu Gln Gly Ser Ser
            20                  25                  30

Ala Ala Thr Glu Ser Lys Trp Asn Val Ser Ile Arg Gln Leu Ile Thr
        35                  40                  45

Gly Ala Asn Pro Met Asp Val Leu Ala Val Gln Glu Ala Gly Val Leu

-continued 50 55 60

Pro Ser Thr Ala Met Met Thr Pro Arg Gln Val Gln Pro Val Gly Val
65 70 75 80

Gly Ile Pro Ile His Glu Tyr Ile Trp Asn Leu Gly Ser Val Ser Arg
85 90 95

Pro Ser Ser Val Tyr Ile Tyr Tyr Ser Arg Val Asp Val Gly Ala Asn
100 105 110

Arg Val Asn Leu Ala Ile Val Ser Arg Val Gln Ala Asp Glu Val Phe
115 120 125

Val Leu Pro Pro Pro Thr Val Ala Ser Arg Pro Ile Ile Gly Ile Arg
130 135 140

Ile Gly Asn Asp Ala Phe Phe Asn Ile His Ala Leu Ala Ser Gly Gly
145 150 155 160

Asn Asp Ala Gly Ala Ile Val Ala Ala Val Asp Met Phe Phe Arg Asn
165 170 175

Arg Pro Asp Ile Asn Trp Met Ile Leu Gly Asp Phe Asn Arg Glu Ser
180 185 190

Gly Ala Leu Val Thr Leu Leu Asp Pro Asp Leu Arg Ala Arg Thr Arg
195 200 205

Val Val Val Pro Pro Ser Ser Thr Gln Thr Ser Gly Arg Thr Ile Asp
210 215 220

Tyr Ala Ile Thr Gly Asn Ser Asn Thr Ala Ala Leu Tyr Asn Pro Pro
225 230 235 240

Pro Ile Val Ala Ile Leu Ala Leu Glu Gly Leu Arg Thr Phe Leu Ala
245 250 255

Ser Asp His Phe Pro Val Asn Phe Arg Arg Pro
260 265

<210> SEQ ID NO 59
<211> LENGTH: 190
<212> TYPE: PRT
<213> ORGANISM: Campylobacter coli

<400> SEQUENCE: 59

Met Lys Lys Phe Phe Ile Leu Phe Phe Ala Leu Leu Ser Phe Leu Lys
1 5 10 15

Ala Glu Pro Ser Leu Asp Glu Leu Ala Asp Phe Thr Pro Met Phe Ala
20 25 30

Ile Arg Ser Leu Glu Thr Gly Ile Ser Leu Ser Pro Phe Arg Lys Thr
35 40 45

Ser Lys Arg Leu Glu Asp Gln Asn Trp Phe Leu Lys Glu Ile Val Ala
50 55 60

Asn Asp Glu Leu Lys Ala Arg Asp Met His Ala Lys Asp Leu Pro Phe
65 70 75 80

Gly Tyr Val Gln Phe Ile Ser Pro Arg Gly Asp Asp Ile Cys Leu Ala
85 90 95

Val Leu Ser Glu Lys Ser Phe Gly Thr Lys Ser Cys Lys Gln Asp Leu
100 105 110

Gln Asp Gly Thr Met Gln Thr Ile Phe Ser Ile Ile Pro Met Thr Asn
115 120 125

Gly Ser Ile Gln Ile Arg Ser Leu Thr Asn Gly Gly Asn Gln Cys Met
130 135 140

Ser Thr Phe Pro Asp Ser Ser Ile Ala Ile Glu Asn Arg Phe Gly Leu
145 150 155 160

-continued

```
Gly Glu Cys Leu Leu Asp Arg Ser Ile Val Thr Val Leu Ser Lys Leu
                165                 170                 175

Phe Phe Phe Ser Pro Ala Ile Ile Glu Ala Ser Ala Ile Tyr
            180                 185                 190


<210> SEQ ID NO 60
<211> LENGTH: 71
<212> TYPE: PRT
<213> ORGANISM: Campylobacter coli

<400> SEQUENCE: 60

Met Gly Ala Ile Val Gly Ala Phe Leu Ile Leu Pro Ile Met Asn Glu
1               5                   10                  15

Leu Thr Leu Ala Ile Thr Phe Ala Val Val Ala Gly Ile Met Val Phe
            20                  25                  30

Ile Ser Phe Asp Glu Leu Leu Pro Ala Ala Lys Thr Tyr Asp Lys Ala
        35                  40                  45

His Asp Ser Leu Tyr Gly Leu Val Leu Gly Met Ala Val Met Ala Val
    50                  55                  60

Ser Leu Ile Leu Leu Asn Pro
65                  70


<210> SEQ ID NO 61
<211> LENGTH: 106
<212> TYPE: PRT
<213> ORGANISM: Campylobacter coli

<400> SEQUENCE: 61

Leu Ser Glu Leu Lys Ile Cys Pro Leu Pro Gln Lys Asn Glu Lys Ala
1               5                   10                  15

Pro Ala Phe His Ala Gly Glu Pro Leu Lys Lys Ile Asn Val Lys Ala
            20                  25                  30

Leu Lys Arg Thr Gly Ile Phe Thr Ala Leu Ala Ile Ala Ile His Asn
        35                  40                  45

Phe Pro Glu Gly Phe Ala Thr Phe Ile Ser Ser Leu Asp Asn Leu Ser
    50                  55                  60

Phe Gly Val Ala Ile Ala Val Ala Val Ala Ile His Asn Ile Pro Glu
65                  70                  75                  80

Gly Arg Gln Phe Leu Tyr Arg Phe Ile Met Leu Gln Arg Ile Arg Lys
                85                  90                  95

Lys Pro Leu Phe Thr Leu His Phe Arg Val
            100                 105
```